United States Patent
Rana

(10) Patent No.: US 9,957,484 B2
(45) Date of Patent: May 1, 2018

(54) METHODS FOR PROMOTING CELL REPROGRAMMING

(71) Applicant: Sanford-Burnham Medical Research Institute, La Jolla, CA (US)

(72) Inventor: Tariq M. Rana, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 725 days.

(21) Appl. No.: 14/256,668

(22) Filed: Apr. 18, 2014

(65) Prior Publication Data

US 2014/0335590 A1 Nov. 13, 2014

Related U.S. Application Data

(63) Continuation of application No. 13/485,694, filed on May 31, 2012, now abandoned.

(60) Provisional application No. 61/492,185, filed on Jun. 1, 2011, provisional application No. 61/554,382, filed on Nov. 1, 2011.

(51) Int. Cl.
*C12N 5/00* (2006.01)
*C12N 5/074* (2010.01)

(52) U.S. Cl.
CPC ........ *C12N 5/0696* (2013.01); *C12N 2501/02* (2013.01); *C12N 2501/602* (2013.01); *C12N 2501/603* (2013.01); *C12N 2501/604* (2013.01); *C12N 2501/606* (2013.01); *C12N 2501/65* (2013.01); *C12N 2501/727* (2013.01); *C12N 2501/998* (2013.01); *C12N 2501/999* (2013.01); *C12N 2506/1307* (2013.01); *C12N 2510/00* (2013.01)

(58) Field of Classification Search
CPC ........ C12N 2501/602; C12N 2501/603; C12N 2501/604; C12N 2501/606; C12N 2501/65; C12N 2501/727; C12N 5/0696; C12N 2501/999; C12N 2506/1307; C12N 2501/998; C12N 2510/00; C12N 2501/02
See application file for complete search history.

(56) References Cited

U.S. PATENT DOCUMENTS

| | | | |
|---|---|---|---|
| 2007/0042941 A1 | 2/2007 | Hirashima et al. | |
| 2008/0064671 A1 | 3/2008 | Barlow et al. | |
| 2010/0120142 A1 | 5/2010 | Impola et al. | |
| 2010/0267141 A1 | 10/2010 | Shi et al. | |
| 2011/0111030 A1 | 5/2011 | Bhasin | |

FOREIGN PATENT DOCUMENTS

| WO | WO 2010/107392 A1 | 9/2010 |
|---|---|---|
| WO | WO 2011/050470 A1 | 5/2011 |

OTHER PUBLICATIONS

Stadtfeld et al. "Induced Pluripotent Stem Cells Generated Without Viral Integration." Science, 2008, vol. 322, pp. 945-949.*
Gonzalez et al "Generation of mouse-induced pluripotent stem cells by transient expression of a single nonviral polycistronic vector." PNAS, 2009, vol. 106, pp. 8918-8922.*
Okita et al. "Generation of Mouse Induced Pluripotent Stem Cells Without Viral Vectors." Science, 2008, vol. 322, pp. 949-953.*
Yamanaka et al. Induction of pluripotent stem cells from mouse fibroblasts by four transcription factors. Cell Prolif., 2008, vol. 41, pp. 51-56.*
Maherali and Hochedlinger. "Guidelines and techniques for the generation of induced pluripotent stem cells."Cell Stem Cell. Dec. 4, 2008;3(6):595-605.*
Li et al. "Advances in understanding the cell types and approaches used for generating induced pluripotent stem cells."J Hematol Oncol. Jul. 19, 2014;7:50.*
Kang HC. "Disease-specific pluripotent stem cells."Korean J Pediatr. Aug. 2010;53(8):786-9.*
Raab et al. "A Comparative View on Human Somatic Cell Sources for iPSC Generation."Stem Cells Int. 2014;2014:768391.*
Okita et al. "Generation of mouse induced pluripotent stem cells without viral vectors."Science. Nov. 7, 2008;322(5903):949-53.*
Gonzalez et al. "Generation of mouse-induced pluripotent stem cells by transient expression of a single nonviral polycistronic vector."Proc Natl Acad Sci U S A. Jun. 2, 2009;106(22):8918-22.*
Yamanaka S. "Induction of pluripotent stem cells from mouse fibroblasts by four transcription factors."Cell Prolif. Feb. 2008;41 Suppl 1:51-6.*
Mosteiro et al. "Tissue damage and senescence provide critical signals for cellular reprogramming in vivo."Science. Nov. 25, 2016;354(6315).*
Stadtfeld and Hochedlinger."Induced pluripotency: history, mechanisms, and applications."Genes Dev. Oct. 15, 2010;24(20):2239-63.*
Kim et al. "Reprogrammed Pluripotent Stem Cells from Somatic Cells."Int J Stem Cells. Jun. 2011; 4(1): 1-8.*
Stadtfeld et al. "Induced pluripotent stem cells generated without viral integration."Science. Nov. 7, 2008;322(5903):945-9.*
Strelchenko et al. "Morula-derived human embryonic stem cells. "Methods Enzymol. 2006;418:93-108.*
Johnson et al. "Understanding pluripotency—how embryonic stem cells keep their options open."Mol Hum Reprod. Sep. 2008;14(9):513-20.*
Neganova et al. "A critical role for p38MAPK signalling pathway during reprogramming of human fibroblasts to iPSCs."Sci Rep. 2017; 7: 41693.*
Rossello et al. "Mammalian genes induce partially reprogrammed pluripotent stem cells in non-mammalian vertebrate and invertebrate species."Elife. Sep. 3, 2013. pp. 1-24.*
Chen et al.: "*Reversine increases the plasticity of lineage-committed mammalian cells*"; Proc. Natl. Acad. Sci. USA, 104(25):10482-7 (2007).
Li et al.: "*A kinase inhibitor screen identifies small-molecule enhancers of reprogramming and iPS cell generation*"; Nat. Commun., 2012, 3:1085 (pp. 1-11).
International Search Report dated Nov. 6, 2012 regarding PCT/US2012/040286.

\* cited by examiner

*Primary Examiner* — Titilayo Moloye

(74) *Attorney, Agent, or Firm* — DLA Piper LLP (US)

(57) ABSTRACT

The present invention is based on the seminal discovery that several kinases play important roles in barrier pathways in somatic cell reprogramming. The present invention provides that modulating expression or activity of these kinases can significantly promote or enhance cell reprogramming efficiency. Key kinases are identified and key regulation networks involving such kinases are also identified that may be advantageously targeted to significantly increase reprogramming efficiency as well as direct differentiation of induced pluripotent stem (iPS) cells.

9 Claims, 33 Drawing Sheets

I. Amino Acid metabolism, Post Translational Modification, Small Molecule Biochemistry II. Gene Expression, Cellular Development

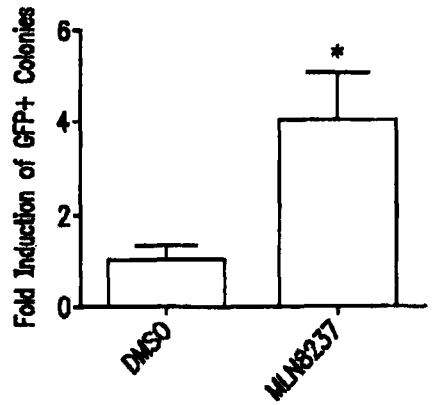
FIG. 13H
| ID | Inhibitor |
|---|---|
| E1 | AGL2043 |
| E2 | Rho Kinase Inhibitor |
| E3 | Reversine |
| E4 | P13-K |
FIG. 14A
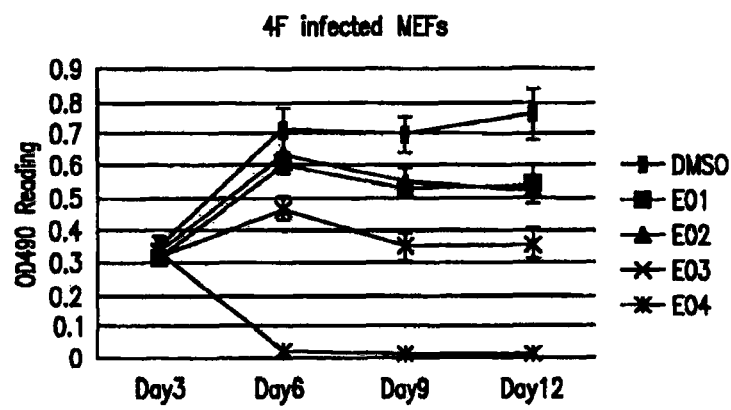
FIG. 14B

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gtattctgca ggcagcagtg                                          20

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gtcttctggc accaaatgc                                           19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
catcaccacc attcccact                                           19

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tcgtaacact ttgcaaatcc a                                        21

<210> SEQ ID NO 5
<211> LENGTH: 21
<212> TYPE: DNA
<213> ORGANISM: Artificial Sequence
<220> FEATURE:
<223> OTHER INFORMATION: Primer -continued

```
<400> SEQUENCE: 5
ggctcccttg acatacaatc a                                              21

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
aagaggtctg accggttc                                                  18

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ccgtcccttt catttctcac                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ttggagaatg ttccgtcgtt                                                20

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gagccctccc ttgacctg                                                  18

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gtatcgaccc cgtccaatc                                                 19

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
aagaactcat ttttgaagag actgc                                          25
```

```
<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
ctctgagccc ttgtcctga                                              19

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
aacaactgca tgaaggcggg aatc                                        24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
cctgtgcagc tggctcaaat caaa                                        24

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
ggaaaatctg catgcttatg act                                         23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16 ccctttttgtc tcagtaactg ctc                                        23

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gagaatttcc ttcacaattc catc                                        24

<210> SEQ ID NO 18
<211> LENGTH: 20
<212> TYPE: DNA
<213> ORGANISM: Artificial Sequence
<220> FEATURE:
<223> OTHER INFORMATION: Primer
```

<400> SEQUENCE: 18
cacttgcatg acgtctctcc                                                      20

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
ggcgggaaac catcagtt                                                        18

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ttcacagagc catcttcctt c                                                    21

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
cacggtcgaa tcccttacc                                                       19

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
tctcaccatg cggtagcc                                                        18

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
ttgcagactt cgggtggt                                                        18

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
tccagggtgc cacacatt                                                        18

```
<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tcctttcaac gttccatgct                                                 20

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
tgggaagtgt atggagaagt acc                                             23

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
cctgaggttc tggcaaagat                                                 20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cactgctgag gtccttctgg                                                 20

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
gaccttctca tagatgagtg gaaga                                           25

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
caggactcca tttcttcttg gt                                              22

<210> SEQ ID NO 31
<211> LENGTH: 18
<212> TYPE: DNA
<213> ORGANISM: Artificial Sequence
<220> FEATURE:
<223> OTHER INFORMATION: Primer
```

```
<400> SEQUENCE: 31
gaaaccagcg aggacgtg                                            18

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
catgacaggc agattgacca                                          20
```

METHODS FOR PROMOTING CELL REPROGRAMMING

CROSS REFERENCE TO RELATED APPLICATIONS

This application is a continuation application of U.S. application Ser. No. 13/485,694, filed May 31, 2012, now pending; which claims the benefit of priority under 35 U.S.C. § 119(e) of U.S. Ser. No. 61/492,185, filed Jun. 1, 2011, and U.S. Ser. No. 61/554,382, filed Nov. 1, 2011, the entire contents of which are incorporated herein by reference in their entireties.

BACKGROUND

Field of the Invention

The present invention relates generally to the field of induced pluripotent stem (iPS) cells and more specifically to methods for promoting cell programming and iPS cell generation, particularly by modulating barrier pathways in somatic cell reprogramming.

Background Information

Generation of induced pluripotent stem cells (iPSCs) by ectopic expression of four transcription factors, Oct4, Sox2, Klf4, and cMyc, has generated enthusiasm in regenerative medicine and developmental biology. In human and mouse somatic cells, other than these four factor combination, iPSCs, which exhibit properties similar to embryonic stem (ES) cells, can be generated with an alternative set of four factors, namely, Oct4, Nanog, Lin28, and Sox2. A number of cell types from different tissues have been successfully reprogrammed. A major roadblock in iPSC derivation and therapeutic use is low reprogramming efficiency, typically from 0.01% to 0.2%. Previous efforts have focused on screening for small molecules to enhance reprogramming efficiency and on developing new methods for iPSC derivation. In addition, synthetic modified RNA- and miRNA-based strategies have been developed to enhance iPSC efficiency and the understanding of the mechanisms of IPSC generation.

Since the discovery of techniques to create cells closely resembling embryonic stem cells, various types of mouse and human somatic cells have been reprogrammed to establish iPSCs. These cells have acquired full capacity to differentiate into different lineages. Resultant differentiated cells reportedly function in vitro and in vivo and serve to correct various diseases in mouse models. Moreover, iPSCs have been generated from tissues of patients with different disease conditions and could be a valuable source to study those pathologies or for drug screening in vitro. Nonetheless, the reprogramming process suffers from extreme low efficiency.

In addition to being a landmark technological advance, the process of inducing pluripotency from differentiated cells also raises fundamental questions about the dynamics of epigenetic stability and its relationship to the potential of pluripotency of a given differentiated state. Several promising approaches have been employed to improve reprogramming efficiency and to address mechanisms of iPSC production. Small molecule-based methods have been employed based on the observation that the treatment of cells with DNA methyltransferase 1 (Dnmt1) inhibitors accelerates reprogramming. TGFβ inhibition also leads to more efficient iPSC induction, as does omission of Sox2 and cMyc. Interestingly, partially reprogrammed iPSCs can be created and then converted to become fully reprogrammed following treatment with factors such as methyl transferase inhibitors.

Genome-wide analysis of promoter binding and induction of gene expression by the four reprogramming factors demonstrates that they bind to similar targets in iPSCs and mouse embryonic stem (mES) cells and likely regulate similar sets of genes, and also shows that targeting of reprogramming factors is altered in partial iPSCs. Several groups reported that p53-mediated tumor suppressor pathways may antagonize iPSC induction. Both p53 and its downstream effector p21 are induced during reprogramming, and lowering the expression of both enhances iPSC colony formation. Since these proteins are up-regulated in most cells expressing the four reprogramming factors, and cMyc reportedly blocks p21 expression, it is unclear how forced expression of these four factors overcomes the cellular responses to oncogenes/transgenes overexpression and why only a very small population of cells becomes fully reprogrammed. By combined dual inhibition (2i) of mitogen-activated protein kinase signaling and glycogen synthase kinase-3 (GSK3) with the self-renewal cytokine leukemia inhibitory factor (LIF), it has been demonstrated that somatic cell state influences the requirements for reprogramming; this raises the intriguing possibility of capturing pre-pluripotent cells that can later advance to ground state pluripotency. Although major advances in the iPSC field including mechanisms and unsolved issues have been recently reviewed, barrier pathways in somatic cell reprogramming are still largely unknown.

Currently, there is a need to both better understand molecular mechanisms underlying reprogramming and develop more efficient methods to generate iPSCs. Elegant approaches have been applied to identify pathways regulating reprogramming. For example, mRNA profiling of somatic cells, iPSCs generated from those cells and intermediate populations that emerge during reprogramming indicates that cells can become "trapped" in a partially reprogrammed state and that treatment with DNA methyl transferase inhibitors enables them to become fully reprogrammed. Genome-wide analysis of promoter binding of specific transcription factors supports the idea that DNA-binding and gene activation are altered in partially reprogrammed iPSCs. Moreover, several groups have shown that p53 pathways, which are activated following overexpression of oncogenic reprogramming factors, act as a major reprogramming barrier. Recent studies show that TGFβ signaling also inhibits reprogramming and perturbs the mesenchymal-to-epithelial transition (MET), a process that enhances reprogramming and is regulated by microRNAs. However, there remains little information about how terminally differentiated cells are reprogrammed to an ES-like state by four transcriptional factors.

Much effort has gone into identifying factors that enhance iPSC derivation. In addition to small molecules that can reportedly replace some reprogramming factors, some compounds are known to enhance overall reprogramming efficiency in the presence of the classic four factors (4F), namely, Tgfbr inhibitors, AZA, vitamin C and VPA. Although some investigators report that VPA treatment dramatically enhances iPSC generation, more recent reports have reexamined the effects of the compound and found them to be modest. Therefore, currently only a limited number of compounds are available to enhance iPSC generation.

Kinases promote phosphorylation of targets by transferring phosphate groups from high-energy donors such as ATP.

Kinases regulate many key processes such as cell cycle events and metabolic switching. However, few kinases have been shown to function in the reprogramming process. Given their critical function in numerous signaling pathways, unidentified kinases may modulate the reprogramming process. Additionally, iPSC generation might be significantly enhanced by manipulating their activity.

SUMMARY

The present invention is based on the seminal discovery that several kinases play important roles in barrier pathways in somatic cell reprogramming. The present invention provides that modulating expression or activity of these kinases can significantly promote or enhance cell reprogramming efficiency. Key kinases are identified and key regulation networks involving such kinases are also identified that may be advantageously targeted to significantly increase reprogramming efficiency as well as direct differentiation of induced pluripotent stem (iPS) cells.

Accordingly, in one embodiment, the present invention provides a method of generating an induced pluripotent stem (iPS) cell. The method includes contacting a somatic cell with a nuclear reprogramming factor; and contacting the cell with an agent which modulates expression or activity of at least one kinase within the cell, thereby generating an iPS cell. In one aspect, the method includes contacting a somatic cell with a nuclear reprogramming factor; and contacting the cell with an agent that inhibits expression or activity of at least one kinase within the cell, thereby generating an iPS cell.

In another aspect, the agent stimulates or inhibits expression or activity of at least one kinase. In another aspect, the agent is a small molecule, a peptide, a nucleic acid, a pluripotency transcription factor or a combination thereof. In an additional aspect, the nucleic acid is an siRNA, shRNA, miRNA, Locked Nucleic Acid (LNA), antisense oligonucleotide, a chemically modified oligonucleotide, or a combination thereof. In one aspect, the kinase phosphorylates cofilin. In another aspect, the agent also disrupts actin polymerization or nucleation.

In one aspect, the kinase is involved in a barrier pathway for somatic cell reprogramming. In another aspect, the kinase is selected from the group of kinases listed in Table 1, Table 3, Table 4, Table 6, Table 7 or Table 8. In another aspect, the kinase is selected from the group consisting of AURKA, P38, IP3K, BUB1B, IRAK3, BMPR2, IRAK2, LIMK2, BMPR1A, TESK1, PRKCA, MAPK1, SRPK1, RAGE, AATK, EPHA5, CDC2L6, DDR1, JAK1, EPHA1, SNF1LK, PIM2, FRAP1, DAPK2, TRIB3, DAPK3, CAMKV, STK25, MAP2K1, PAK7, STK24, CSNK2B, KHK, 6330514A18RIK, NPR2, BMP2K, EIF2AK2, MOS, NEK2, NEK6, PLK1, PLK2, RNASEL, SCYL1, TBK1, TLK2, UHMK1, RPS6KB1, AK3, DGKε, PIK3C2G, GALK2, NME1, GTF2F1, PAX8, PKIG, PIK3R5, GIT2, PIK3AP1, CNKSR3, PKIB, PER2, FASTKD5, and a combination thereof. In another aspect, the kinase is selected from the group consisting of DGKε, PLK2, TESK1, BMP2K, BMPR2, MAPK1, and a combination thereof. In another aspect, the kinase is selected from the group consisting of DGKε, PLK2, TESK1, and a combination thereof.

In another aspect, the agent is selected from the group of compounds listed in Table 5, Table 7, or Table 8. In another aspect, the agent is selected from the group consisting of KN-62, Alsterpaullone, Arcyriaflavin A, IP3K inhibitor, ML-7, PP3, Syk inhibitor III, Aurora kinase inhibitor III, Sphingosine kinase inhibitor, TGF-β RI inhibitor III, p38 MPA kinase inhibitor IV, and a combination thereof. In another aspect, the agent is selected from the group consisting of AGL 2043, Cdk2/9 inhibitor, Cdk/Crk inhibitor, Fascaplysin, Rho kinase inhibitor IV, K-252a Nocardiopsis, UCN-01, PI 3-K inhibitor VIII, Reversine, and a combination thereof. In another aspect, the small molecule is selected from the group consisting of:

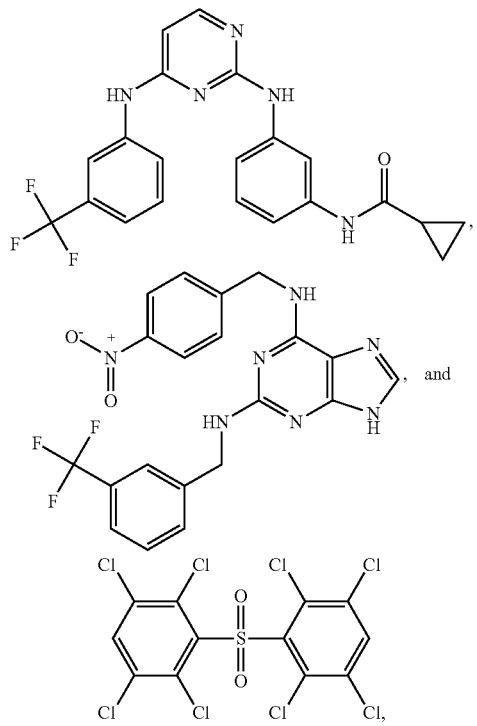

as well as salts and functional analogs thereof.

In one aspect, the method further includes the step of contacting the cell with an inhibitor of microRNA, a microRNA, or a miRNA mimic that enhances reprogramming of an induced pluripotent stem (iPS) cell. In another aspect, the inhibitor of microRNA or miRNA mimic is a small molecule, a peptide, a nucleic acid, or a combination thereof. In another aspect, the nucleic acid is an siRNA, shRNA, Locked Nucleic Acid (LNA), antisense oligonucleotide, a chemically modified oligonucleotide, or a combination thereof.

In one aspect, the method further includes the step of contacting the cell with a second agent that enhances reprogramming of an induced pluripotent stem (iPS) cell. In another aspect, the second agent is a small molecule, a peptide, a nucleic acid, a pluripotency transcription factor or a combination thereof. In another aspect, the nucleic acid is an siRNA, shRNA, or miRNA. In another aspect, the second agent is an microRNA, miRNA mimic, miRNA inhibitor, Locked Nucleic Acid (LNA), antisense oligonucleotide, a chemically modified oligonucleotide, or a combination thereof.

In another aspect, the second agent is an nonsteroidal anti-inflammatory drug (NSAID). In another aspect, the second agent is selected from the group consisting of nabumetone, 4-hydroxytamoxifen (OHTM), corynanthine, moclobemide, nickel sulfate hexahydrate ($NiSO_4$), lectin, and a combination thereof. In another aspect, the second agent is selected from the group consisting of nabumetone, 4-hydroxytamoxifen (OHTM), corynanthine, moclobemide, nickel sulfate hexahydrate (NiSO$_4$), lectin, 2, 3, 7, 8-tetrachlorodibenzo-p-dioxin, inhibitor of TGF-β, Acitretin, Retinoic acid p-hydroxyanilide, Diacerein, Phorbol 12-myristate 13-acetate, Progesterone, Tolazamide, 15-deoxy-Δ$^{12,\ 14}$-prostaglandin J$_2$, (−)-Norepinephrine, β-estradiol, and a combination thereof.

In one aspect, the nuclear reprogramming factor is encoded by a gene contained in a vector. In another aspect, the nuclear reprogramming factor is a SOX family gene, a KLF family gene, a MYC family gene, SALL4, OCT4, NANOG, LIN28, or a combination thereof. In another aspect, the nuclear reprogramming factor is one or more of OCT4, SOX2, KLF4, C-MYC.

In another aspect, the somatic cell is contacted with the reprogramming factor prior to, simultaneously with or following contacting the agent. In another aspect, the somatic cell is a mammalian cell. In another aspect, the somatic cell is a fibroblast.

In another embodiment, the present invention provides an induced pluripotent stem (iPS) cell produced using the method described herein. In another embodiment, the present invention provides an enriched population of induced pluripotent stem (iPS) cells produced by the method described herein. In another embodiment, the present invention provides a differentiated cell derived by inducing differentiation of the pluripotent stem cell produced by the method described herein.

In another embodiment, the present invention provides a method of treating a subject. The method includes generating an induced pluripotent stem (iPS) cell from a somatic cell of the subject by the method described herein; inducing differentiation of the iPS cell, and introducing the cell into the subject, thereby treating the condition. In another embodiment, the present invention provides the use of an agent inhibiting expression or activity of at least one kinase within the cell for increasing efficiency of generating of iPS cells.

In one aspect, the agent is a small molecule, a peptide, a nucleic acid, a pluripotency transcription factor or a combination thereof. In another aspect, the nucleic acid is an siRNA, shRNA, miRNA, Locked Nucleic Acid (LNA), antisense oligonucleotide, a chemically modified oligonucleotide, or a combination thereof. In another aspect, the kinase is involved in a barrier pathway for somatic cell reprogramming. In another aspect, the kinase is selected from the group identified in Table 1, Table 3, Table 4, Table 6, Table 7 or Table 8. In another aspect, the kinase is selected from the group consisting of AURKA, P38, IP3K, BUB1B, IRAK3, BMPR2, IRAK2, LIMK2, BMPR1A, TESK1, PRKCA, MAPK1, SRPK1, RAGE, AATK, EPHA5, CDC2L6, DDR1, JAK1, EPHA1, SNF1LK, PIM2, FRAP1, DAPK2, TRIB3, DAPK3, CAMKV, STK25, MAP2K1, PAK7, STK24, CSNK2B, KHK, 6330514A18RIK, NPR2, BMP2K, EIF2AK2, MOS, NEK2, NEK6, PLK1, PLK2, RNASEL, SCYL1, TBK1, TLK2, UHMK1, RPS6KB1, AK3, DGKε, PIK3C2G, GALK2, NME1, GTF2F1, PAX8, PKIG, PIK3R5, GIT2, PIK3AP1, CNKSR3, PKIB, PER2, FASTKD5, and a combination thereof. In another aspect, the kinase is selected from the group consisting of DGKε, PLK2, TESK1, BMP2K, BMPR2, MAPK1, and a combination thereof. In another aspect, the kinase is selected from the group consisting of DGKε, PLK2, TESK1, and a combination thereof.

In another aspect, the agent is selected from the group of compounds listed in Table 5, Table 7, or Table 8. In another aspect, the agent is selected from the group consisting of KN-62, Alsterpaullone, Arcyriaflavin A, IP3K inhibitor, ML-7, PP3, Syk inhibitor III, Aurora kinase inhibitor III, Sphingosine kinase inhibitor, TGF-β RI inhibitor III, p38 MPA kinase inhibitor IV, and a combination thereof. In another aspect, the agent is selected from the group consisting of AGL 2043, Cdk2/9 inhibitor, Cdk/Crk inhibitor, Fascaplysin, Rho kinase inhibitor IV, K-252a Nocardiopsis, UCN-01, PI 3-K inhibitor VIII, Reversine, and a combination thereof. In another aspect, the small molecule is selected from the group consisting of:

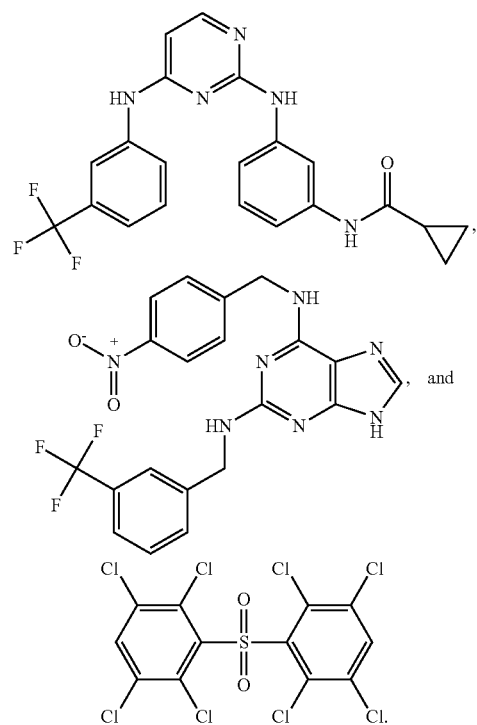

In another embodiment, the present invention provides a method of identifying barrier pathways in somatic cell reprogramming in a subject. The method includes generating a lentiviral shRNA library, wherein the lentiviral shRNA library targets selected genes of the subject; preparing shRNA lentiviruses using cell culture; and contacting the shRNA lentiviruses to a reporter cell line for somatic cell reprogramming, thereby identifying barrier pathways in somatic cell reprogramming.

In one aspect, the lentiviral shRNA library targets kinase genes of an entire kinome of the subject. In another aspect, the subject is a mammalian. In another aspect, the subject is a mouse. In another aspect, the reporter cell line for somatic cell reprogramming is Oct4-GFP mouse embryonic fibroblast (MEF). In another aspect, the cell culture includes 293FT cells.

In another embodiment, the present invention provides a method of generating an induced pluripotent stem (iPS) cell. The method includes contacting a cell with an agonist of microRNA in combination with an agent which modulates expression or activity of at least one kinase within the cell, thereby generating an iPS cell.

In one aspect, the agonist of microRNA includes a microRNA or miRNA mimic that enhances reprogramming of an induced pluripotent stem (iPS) cell. In another aspect, the agonist is a small molecule, a peptide, a nucleic acid, a pluripotency transcription factor or a combination thereof.

In another embodiment, the present invention provides a method of generating an induced pluripotent stem (iPS) cell. The method includes contacting a cell with an microRNA inhibitor in combination with an agent which modulates expression or activity of at least one kinase within the cell, thereby generating an iPS cell.

In one aspect, the microRNA inhibitor is a small molecule, a peptide, a nucleic acid, a pluripotency transcription factor or a combination thereof. In an additional aspect, the nucleic acid is an siRNA, shRNA, Locked Nucleic Acid (LNA), antisense oligonucleotide, a chemically modified oligonucleotide, or a combination thereof. In various aspect, the chemically modified oligonucleotide described herein includes a 2'-deoxyribonucleotide, 2'-O-methyl ribonucleotide, 2'-fluoro ribonucleotide, 2'-amino ribonucleotide, 2'-O-amino ribonucleotide, 2'-C-allyl ribonucleotide, 2'-O-allyl ribonucleotide, 2'-methoxyethyl ribonucleotides, 5'-C-methyl ribonucleotides, or a combination thereof.

In another embodiment, the invention provides a method of screening for a modulator of somatic cell reprogramming. The method includes: a) contacting a cell of a reporter cell line for somatic cell reprogramming with one or more nuclear reprogramming factors; b) contacting the cell of (a) with a test agent; c) detecting a reporter of the cell which is indicative of pluripotency; d) comparing the level of the reporter with that of a corresponding cell not contacted with the test agent, wherein a test agent that increases or decreases the level of the reporter as compared to the level of the reporter in the corresponding cell is identified as a modulator of somatic cell reprogramming. In various aspects, the test agent is a small molecule, a peptide, a nucleic acid, a pluripotency transcription factor or a combination thereof. In one aspect, the reporter cell line for somatic cell reprogramming is a somatic cell line, wherein the cells include a nucleic acid sequence encoding a promoter of an endogenous nuclear reprogramming factor operably linked to a reporter gene. In one aspect, the test agent activates or inhibits the expression or activity of a kinase. In various aspects, the kinase is selected from the group of kinases listed in Table 1, Table 3, Table 4, Table 6, Table 7 or Table 8.

BRIEF DESCRIPTION OF THE DRAWINGS

FIG. 1A shows experimental design for the whole kinome screen with lentiviral shRNA library. Oct4-GFP MEFs are transduced with retrovirus of four pluripotency factors, Oct4, Sox2, Klf4, and c-Myc (OSKM; the four factors—4F), to induce reprogramming. 3,686 lentiviruses are produced in 293FT cells carrying shRNAs targeting the entire kinome. MEFs transduced with 4F are subsequently infected with lentiviruses individually in separate wells. ES medium is changed every other day from Day 4. GFP+ colonies are quantified on Days 16 to 18. Knockdown levels of target kinases are analyzed on Day 4 (see FIG. 5). CTRL shows control lanes containing GFP+ colonies with shRNAs targeting p53.

FIG. 1B shows identification of barrier kinases from primary screen. Dot-plot shows the result of 3,686 shRNAs targeting 734 kinase genes as tested in the primary screen. GFP+ colony counts are shown as fold changes after normalization with that of control pLKO lentiviral-infected cells. A two-fold threshold is used to select barrier kinases as hits. Validation of 157 genes from the primary screen is performed in duplicate in a 12-well format in the secondary screen. Subsequently, 60 genes are further validated in the tertiary screen in a 12-well format in duplicate and repeated five times.

FIGS. 2A and 2B show top ten highly interconnected molecular functions identified with IPKB analysis (see FIG. 14) are shown as four networks: (I) Amino Acid Metabolism, Post-Translational Modification, Small Molecule Biochemistry; (II) Gene Expression and Cellular Development; (III) Cell Cycle, Cell Signaling, Cell Death; (IV) Cellular Growth and Proliferation, Cancer. Interactions are shown by the following arrows: direct interactions (solid lines); indirect interactions (dotted lines); action of kinases pointed by arrowheads; inhibitory action is indicated by a vertical line next to arrowheads (e.g., MTOR). Interactions between the kinases identified in the functional genomics screen are shown.

FIG. 2C shows six of the kinases identified as barriers in iPSC generation are involved in the ILK signaling network. Analysis of this network is performed by IPKB system, and the six selected kinases are labeled in red.

FIG. 4A shows that TESK1 is differently expressed in mESCs/MEFs and can be efficiently knocked down by shRNAs. TESK1 expressions are detected by western blotting in Oct4-GFP MEFs, mES cells, and non-targeting shRNA- and shTESK1-transduced Oct4-GFP MEFs. GAPDH is detected as an internal control. MEFs have poly-nucleation of actin filaments; knockdown of TESK1 disrupts this filamental structure. Actin organizations are detected by rhodamine-labeled phalloidin in MEF and mES cells. MEFs are transfected with siRNA-targeting TESK1 or control for 72 hours. FIG. 4B shows that TESK1 regulates phosphorylation of cofilin in MEFs. Western blotting is used to detect P-cofilin level in MEFs and mES (left) and knockdown of TESK1 in MEFs resulted in decreased P-cofilin (right). Limk2 silencing results in a phenotype, decreased P-cofilin and disruption of actin filaments, very similar to TESK1 (see FIG. 15).

FIG. 4C shows proposed mechanisms of TESK1 and LIMK2 in iPSC generation. TESK1 and LIMK2 phosphorylates cofilin to promote/stabilize cytoskeleton structure in cells. RNAi-mediated silencing of TESK1 and LIMK2 depletes cofilin phosphorylation, which in turn disrupts actin-poly nucleation. Disruption of the actin cytoskeleton promotes the mesenchymal-to-epithelial transition of 4F-infected MEFs and thus enhances reprogramming.

FIG. 5A shows that six identified kinases can be efficiently knocked down by shRNAs. Total RNAs were extracted 4 days after lentiviral transduction and used in RT-qPCR to determine knockdown levels of targeted genes. The gene expression level in the pLKO.1 sample was set as 100%. Results were obtained from three independent experiments. FIG. 5B shows that knockdown of the six kinases enhanced MET transition in 4F-infected MEFs. E-Cadherin expression was used as the marker for the induction of mesenchymal-to-epithelial transition (MET) during initial stage of reprogramming. FIG. 5C shows analysis of genomic integration of shRNAs. Genomic DNA insertion of shRNAs is tested by PCR amplification of genomic DNA against puromycin marker gene in pLKO.1 vector. Genomic DNA is isolated from one clone each of five kinase knockdown iPSCs (BMPR2 clone #2, MAPK1 clone #1, BMP2K clone #1, DGKε clone #6, PLK2 clone #3) and from two clones of TESK1 knockdown cells (clone #2 and #4, which are further characterized for teratoma formation). Water with the primer set is used as a negative control.

FIG. 6C shows that four functional associations described in FIG. 3 are merged to generate a global network.

FIG. 9A is a diagram of the design of the screen. MEFs were transduced with the four mouse reprogramming factors (4F) for two days and reseeded into 96-well plates. Drugs were added at a final concentration of 2 µM on day 3. Medium was changed every other day until day 13, and cells were then harvested for colony counting and AP staining. FIG. 9B is a graphical representation of a representative plate showing quantification of Oct4-GFP+ colonies. GFP+ colonies were counted directly under a fluorescence microscope, and data was compared with DMSO-treated controls. * indicates identified hits. Columns 1 and 12 indicate control (DMSO) wells. Potential candidates were determined by both GFP+ colony number, morphology, and AP-positivity.

FIG. 10A is a table listing candidate hits for secondary screening conducted in 12-well plates of the 11 barrier hits of FIG. 10B. FIG. 10B is a histogram showing compounds B4, B8 and B10 at 2 µM significantly enhanced reprogramming. Drugs were added at day 3 and Oct4-GFP+ colonies were quantified at day 13 after transduction. Data from three independent sets were normalized to DMSO-treated wells. *p<0.01. FIG. 10C is a histogram of results from the same assay as in FIG. 10B with 1 µM drug. Note that at this concentration B6 treatment significantly enhances reprogramming. Data represents two independent experiments with three independent wells. *p<0.01. FIG. 10D is a diagram of the chemical structures of identified inhibitors.

FIGS. 11A-11B are histograms depicting siRNA knockdown of potential target mRNAs. Potential targets of B6, B8 and B10 inhibitors were knocked down by siRNAs in MEFs or mES (ItpkA only). 50 nM siRNAs were transfected and total RNAs was harvested at day 2 for RT-qPCR analysis. Data represents analysis of duplicate wells. FIG. 11C is a histogram showing that knockdown of B6 inhibitor targets enhances reprogramming. Potential targets of B6 were knocked down by siRNAs, and reprogramming efficiency was quantified by counting Oct4-GFP+ colonies. Data from three independent experiments were normalized to siControl-transfected samples. *p<0.01. FIG. 11D is a histogram showing that knockdown of B8 and B10 targets enhances reprogramming. Data from two independent experiments were normalized to siControl-transfected cells.

FIGS. 13A-13h are a series of graphical representations depicting Aurora A kinase inhibition by B6 promoting Akt mediated inactivation of GSK3β. FIG. 13A is a western blot showing B6 treatment increases aurora A kinase protein levels. Both 4F-infected (day 3) and mock MEFs were treated with 1 µM B6 for 2 days and cells were harvested for western blotting of Aurora A kinase. Actin served as loading control.

FIG. 13B is a graph showing Aurora A kinase mRNA levels are significantly increased by 4F expression during reprogramming. MEFs were infected with 4F for 3 days and treated under mock conditions or with DMSO or 1 µM B6 for 2 days prior to RT-qPCR analysis of total RNA. B6 treatment did not alter induction of Aurora A kinase by 4F.

FIG. 13C is a western blot showing inhibition of Aurora A kinase promotes increased phosphorylation of GSK3β kinase. 4F-infected MEFs were treated with different doses of B6 inhibitor starting at day 3 post-infection for 48 hrs before being harvested for western blotting analysis.

FIG. 13D is a western blot showing inhibition of Aurora A kinase by MLN8237 promotes GSK3β phosphorylation dose-dependently. The experiment was the same as FIG. 5C. Actin served as the loading control.

FIG. 13E is a western blot showing expression of a dominant negative form of Aurora A kinase promotes GSK3β phosphorylation. MEFs were infected with 4F and expression vectors for RFP, wild-type (wt) Aurora A kinase or the D274A kinase-dead mutant of human Aurora A kinase. Expression of wt AurkA inhibited GSK3β phosphorylation, while overexpression of the mutant promoted the process. Exposure time was almost doubled for 4F-infected samples.

FIG. 13F is a western blot showing phosphorylation of GSK3β is mediated by Akt. 4F-infected MEFs were treated with 1 μM each of Akt inhibitor (Akt X) and B6. GSK3β phosphorylation was diminished likely due to Akt inhibition.

FIG. 13G is a histogram showing Akt X treatment compromises reprogramming. Akt X inhibitor was added at a final concentration of 1 μM. Error bar represents standard deviation of results derived from triplicate wells. *p<0.05.

FIG. 13H is a histogram showing AurkA inhibition by MLN8237 enhances reprogramming. 4F-infected MEFs at day 3 were treated with 10 nM MLN8237 for 10 days and GFP+ colonies counted to determine reprogramming efficiency. MLN8237 enhanced iPSC generation similarly to effects seen with 1 μM B6. Data is derived from two experiments using triplicate wells. *p<0.05.

FIGS. 14A-14D are a series of tabular and graphical representations depicting essential hits that block the reprogramming process. FIG. 14A is a table listing essential hits that are not Cdk inhibitors. FIG. 14B is a graph showing proliferation of wild-type MEFs is altered by inhibitor treatment. MEFs were treated with drugs at 2 μM and proliferation was assayed by using the Celltiter 96™ aqueous method (Promega). Y-axis represents the absorbance at 490 nm to detect formazan, which is converted from MTS tetrazolium by living cells. A higher reading indicates increased cell number. FIG. 14C is a graph showing proliferation of 4F-transduced MEFs was also altered by drug treatment. FIG. 14D is a histogram showing that reprogramming efficiency was decreased by drug treatment. Oct4-GFP+ colonies were quantified at day 13.

FIG. 15A is a histogram showing inhibitor B8 and B10 enhanced iPSC generation in non-permissive conditions in which 4F expression was too low to reprogram vehicle-treated MEFs. Cells were infected with 4F and drugs were added at days 3 post-infection. GFP+ colonies were counted at day 12-13. Non permissive condition refers to occasions where 4F expression level does not reach to the threshold for successful reprogramming thus no GFP+ colonies could be detected. Data represents experiments using duplicate wells for each treatment. FIG. 15B is a histogram of Oct4-GFP+ colony growth. 4F-transduced MEFs were treated with indicated concentrations of kinase inhibitors B6, B8 or B10 or with DMSO control starting at day 3 post 4F transduction, and Oct4-GFP+ colonies were counted at day 13 after transduction. Data represents three independent wells.

FIG. 16A is a graph plotting relative cell viability. 4F-infected MEFs were seeded in 96-well plates and 0.5 μM of three inhibitors was added at day 3 after transduction (Day 0 in dataset). Proliferation of cells was analyzed every other day using the Celltiter 96™ aqueous method (Promega). FIG. 16B is a graph plotting relative cell viability. Proliferation of uninfected MEFs is not altered by inhibitor treatment. The experimental procedure is the same as in FIG. 16A.

FIG. 23A is a histogram of induction of GFP+ colonies by MLN8237. The number of Oct4-GFP+ colonies was significantly increased upon MLN8237 treatment. Data is derived from analysis of three independent wells. FIG. 23B is a histogram of relative mRNA level. MLN8237 treatment induces mES-specific gene expression in 4F-transduced MEFs. Cells were harvested at day 14 post 4F transduction. Nanog, Tet1 and Eras expression was analyzed in cells treated with DMSO or MLN8237. Shown are data derived from three independent wells.

FIG. 24A is a series of images of DNA analysis by flow cytometry. 4F-infected MEFs were treated with different concentrations of B6 at day 3 post-infection. Cells were harvested after 48 hr of drug treatment, subjected to PI staining and analyzed for DNA content by flow cytometry.

FIG. 24B is a series of images of DNA analysis by flow cytometry. MLN8237 treatment at 10 nM did not alter the cell cycle of 4F-infected MEFs. The experimental procedure was as in FIG. 24A.

DETAILED DESCRIPTION

Figure 1A:
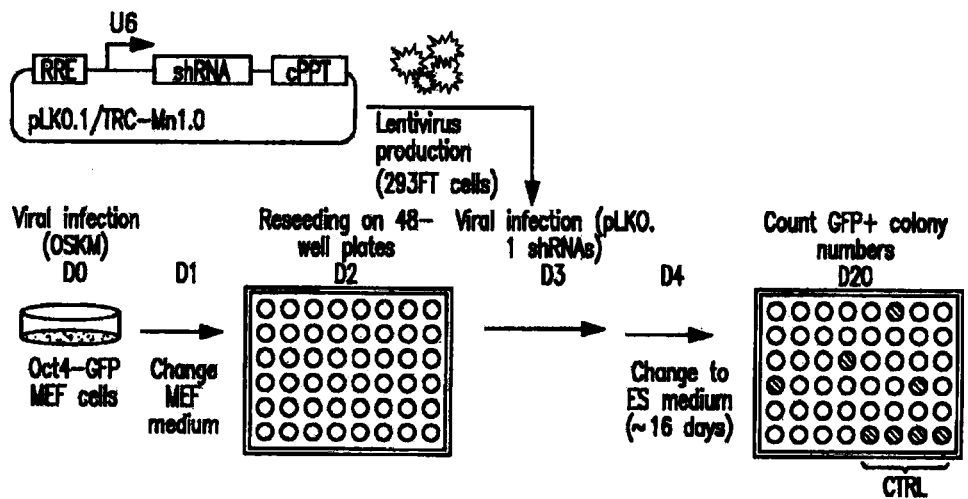
FIGS. 1A-1B show kinome-wide screen for barrier pathways of induced pluripotent stem (iPS) cells generation.

Creation of induced pluripotent stem cells (iPSCs) from somatic cells by ectopic expression of transcription factors has galvanized the fields of regenerative medicine and developmental biology. The present invention provides a whole kinome-wide RNAi screen to identify kinases that regulate somatic cell reprogramming to iPSCs. The present invention provides that at least 3,686 shRNA lentiviruses are used for targeting 734 kinase genes covering the entire mouse kinome and individually screened these viruses in iPSC generation experiments. At least 59 kinases, regulating diverse cellular function, are confirmed as barriers to iPSC generation. At least six kinases are characterized in depth and the present invention provides that TESK1 and LIMK2 knockdown by shRNA can promote mesenchymal to epithelial transition and can result in decreased cofilin phosphorylation and disruption of actin filament structures during reprogramming. Thus, the present invention provides a wealth of kinome networks regulating reprogramming, wherein TESK1 and LIMK2 kinase function uncovers cytoskeleton remodeling as a novel mechanism for modulating somatic cell reprogramming.

Somatic cells can be reprogrammed to reach an ES-like state by overexpression of defined factors. Currently, the reprogramming process suffers from extremely low efficiency, requiring further understanding of underlying mechanisms in order to develop new reprogramming methods and understand the transitions to a pluripotent state. The present invention is based on the discovery of key barrier pathways for iPSC induction. A key aspect being the discovery of kinases which play an important role for the induction of iPSCs. The present invention provides that inhibition of expression or activity of these kinases, which are involved in barrier pathways for iPSC induction, can promote induction of iPSCs (i.e., somatic cell reprogramming).

The present invention further provides an inhibitor screen identifying kinases that enhance or present a barrier to reprogramming. In part, inhibitors of p38, IPTK and aurora kinases were found to enhance iPSCs generation. iPS cells derived from inhibitor-treated samples were capable of reaching a fully reprogrammed state. Knockdown of target kinases by siRNAs confirmed that these genes function as barriers. As discussed herein, Aurora A kinase, which functions in centrosome activity and spindle assembly, is highly induced during reprogramming and inhibits Akt-mediated inactivation of GSK3β, resulting in compromised reprogramming efficiency. Together, the results herein not only identify new compounds that enhance iPSC generation but provide heretofore unreported insight into the function of Aurora A kinase in the reprogramming process.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In various embodiments, one or more nuclear reprogramming factors can be used to induce reprogramming of a differentiated cell without using eggs, embryos, or ES cells. Efficiency of the induction process is enhanced by utilizing an agent that alters microRNA levels or activity within the cell during the induction process. The method may be used to conveniently and highly reproducibly establish an induced pluripotent stem cell having pluripotency and growth ability similar to those of ES cells. For example, the nuclear reprogramming factor may be introduced into a cell by transducing the cell with a recombinant vector comprising a gene encoding the nuclear reprogramming factor along with a recombinant vector comprising a polynucleotide encoding an RNA molecule, such as a microRNA. Accordingly, the cell can express the nuclear reprogramming factor expressed as a product of a gene contained in the recombinant vector, as well as expressing the microRNA expressed as a product of a polynucleotide contained in the recombinant vector thereby inducing reprogramming of a differentiated cell at an increased efficiency rate as compare to use of the nuclear reprogramming factor alone.

As used herein, pluripotent cells include cells that have the potential to divide in vitro for an extended period of time (greater than one year) and have the unique ability to differentiate into cells derived from all three embryonic germ layers, including the endoderm, mesoderm and ectoderm.

Somatic cells for use with the present invention may be primary cells or immortalized cells or cell lines thereof. Such cells may be primary cells (non-immortalized cells), such as those freshly isolated from an animal, or may be derived from a cell line (immortalized cells). In an exemplary aspect, the somatic cells are mammalian cells, such as, for example, human cells or mouse cells. They may be obtained by well-known methods, from different organs, such as, but not limited to skin, lung, pancreas, liver, stomach, intestine, heart, reproductive organs, bladder, kidney, urethra and other urinary organs, or generally from any organ or tissue containing living somatic cells. Mammalian somatic cells useful in the present invention include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Exemplary adult stem cells include hematopoietic stem cells, neural stem cells, and mesenchymal stem cells.

As used herein, reprogramming is intended to refer to a process that alters or reverses the differentiation status of a somatic cell that is either partially or terminally differentiated. Reprogramming of a somatic cell may be a partial or complete reversion of the differentiation status of the somatic cell. In an exemplary aspect, reprogramming is complete wherein a somatic cell is reprogrammed into an induced pluripotent stem cell. However, reprogramming may be partial, such as reversion into any less differentiated state. For example, reverting a terminally differentiated cell into a cell of a less differentiated state, such as a multipotent cell.

In various aspects of the present invention, nuclear reprogramming factors or pluripotency transcription factors are genes that induce pluripotency and utilized to reprogram differentiated or semi-differentiated cells to a phenotype that is more primitive than that of the initial cell, such as the phenotype of a pluripotent stem cell. Such genes and agents are capable of generating a pluripotent stem cell from a somatic cell upon expression of one or more such genes having been integrated into the genome of the somatic cell. As used herein, a gene that induces pluripotency is intended to refer to a gene that is associated with pluripotency and capable of generating a less differentiated cell, such as a pluripotent stem cell from a somatic cell upon integration and expression of the gene. The expression of a pluripotency gene is typically restricted to pluripotent stem cells, and is crucial for the functional identity of pluripotent stem cells.

An agent useful in any of the methods of the invention can be any type of molecule, for example, a polynucleotide, a peptide, a peptidomimetic, peptoids such as vinylogous peptoids, chemical compounds, such as organic molecules or small organic molecules, or the like. Accordingly, in one aspect, an agent for use in the method of the present invention is a polynucleotide, such as an antisense oligonucleotide or RNA molecule. In various aspects, the agent may be a polynucleotide, such as an antisense oligonucleotide or RNA molecule, such as microRNA, dsRNA, siRNA, stRNA, and shRNA.

MicroRNAs (miRNA) are single-stranded RNA molecules, which regulate gene expression. miRNAs are encoded by genes from whose DNA they are transcribed but miRNAs are not translated into protein; instead each primary transcript (a pri-miRNA) is processed into a short stem-loop structure called a pre-miRNA and finally into a functional miRNA. Mature miRNA molecules are either fully or partially complementary to one or more messenger RNA (mRNA) molecules, and their main function is to down-regulate gene expression. MicroRNAs can be encoded by independent genes, but also be processed (via the enzyme Dicer) from a variety of different RNA species, including introns, 3' UTRs of mRNAs, long noncoding RNAs, snoRNAs and transposons. As used herein, microRNAs also include "mimic" microRNAs which are intended to mean a microRNA exogenously introduced into a cell that have the same or substantially the same function as their endogenous counterpart. Thus, while one of skill in the art would understand that an agent may be an exogenously introduced RNA, an agent also includes a compound or the like that increase or decrease expression of microRNA in the cell.

The terms "small interfering RNA" and "siRNA" also are used herein to refer to short interfering RNA or silencing RNA, which are a class of short double-stranded RNA molecules that play a variety of biological roles. Most notably, siRNA is involved in the RNA interference (RNAi) pathway where the siRNA interferes with the expression of a specific gene. In addition to their role in the RNAi pathway, siRNAs also act in RNAi-related pathways (e.g., as an antiviral mechanism or in shaping the chromatin structure of a genome).

Polynucleotides of the present invention, such as antisense oligonucleotides and RNA molecules may be of any suitable length. For example, one of skill in the art would understand what lengths are suitable for antisense oligonucleotides or RNA molecule to be used to regulate gene expression. Such molecules are typically from about 5 to 100, 5 to 50, 5 to 45, 5 to 40, 5 to 35, 5 to 30, 5 to 25, 5 to 20, or 10 to 20 nucleotides in length. For example the molecule may be about 5, 10, 15, 16, 17, 18, 19, 20, 21, 22, 23, 24, 25, 26, 27, 28, 29, 30, 31, 32, 33, 34, 35, 40, 45 or 50 nucleotides in length. Such polynucleotides may include from at least about 15 to more than about 120 nucleotides, including at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides or greater than 120 nucleotides.

The term "polynucleotide" or "nucleotide sequence" or "nucleic acid molecule" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the terms as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR). It should be recognized that the different terms are used only for convenience of discussion so as to distinguish, for example, different components of a composition.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available, as are polynucleotides containing such nucleotide analogs. The covalent bond linking the nucleotides of a polynucleotide generally is a phosphodiester bond. However, depending on the purpose for which the polynucleotide is to be used, the covalent bond also can be any of numerous other bonds, including a thiodiester bond, a phosphorothioate bond, a peptide-like bond or any other bond known to those in the art as useful for linking nucleotides to produce synthetic polynucleotides.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

In various embodiments antisense oligonucleotides or RNA molecules include oligonucleotides containing modifications. A variety of modification are known in the art and contemplated for use in the present invention. For example oligonucleotides containing modified backbones or non-natural internucleoside linkages are contemplated. As used herein, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In various aspects modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In various aspects modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In various aspects, oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. In various aspects, oligonucleotides may include phosphorothioate backbones and oligonucleosides with heteroatom backbones. Modified oligonucleotides may also contain one or more substituted sugar moieties. In some embodiments oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m$ $CH_3$, $O(CH_2)_nOCH_3$, $O(CH_2)_nNH_2$, $O(CH_2)_nCH_3$, $O(CH_2)_n$ $ONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, N3, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy (2'$OCH_2CH_2OCH_3$, also known as 2'-O-(2-methoxyethyl) or 2'-MOE).

In one embodiment, the invention features a chemically modified nucleic acid molecule that includes one or more chemical modifications described herein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5'-C-methyl nucleotides, and terminal glyceryl and/or inverted deoxy abasic residue incorporation. These chemical modifications are shown to preserve activity in cells while at the same time, dramatically increasing the serum stability of these compounds. In one aspect, the chemically modified nucleotide used in the invention includes a 2'-deoxyribonucleotide, 2'-O-methyl ribonucleotide, 2'-fluoro ribonucleotide, 2'-amino ribonucleotide, 2'-O-amino ribonucleotide, 2'-C-allyl ribonucleotide, 2'-O-allyl ribonucleotide, 2'-methoxyethyl ribonucleotide, 5'-C-methyl ribonucleotide, or a combination thereof. In another aspect, the chemically modified oligonucleotide used in the invention includes a 2'-deoxyribonucleotide, 2'-O-methyl ribonucleotide, 2'-fluoro ribonucleotide, 2'-amino ribonucleotide, 2'-O-amino ribonucleotide, 2'-C-allyl ribonucleotide, 2'-O-allyl ribonucleotide, 2'-methoxyethyl ribonucleotide, 5'-C-methyl ribonucleotide, or a combination thereof.

In a non-limiting example, the introduction of chemically modified nucleotides into nucleic acid molecules provides a powerful tool in overcoming potential limitations of in vivo stability and bioavailability inherent to native RNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically modified nucleic acid molecule is reduced as compared to a native nucleic acid molecule, for example, when compared to a native unmodified nucleic acid molecule, the overall activity of the modified nucleic acid molecule can be greater than that of the native molecule due to improved stability and/or delivery of the molecule.

In related aspects, the present invention includes use of Locked Nucleic Acids (LNAs) to generate antisense nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne ($—CH_2—$)$_n$ group bridging the 2' oxygen atom and the 4' carbon atom wherein n is 1 or 2.

Other modifications include 2'-methoxy(2'-O—CH$_3$), 2'-aminopropoxy(2'-OCH$_2$CH$_2$CH$_2$NH$_2$), 2'-allyl (2'-CH—CH—CH$_2$), 2'-O-allyl (2'-O—CH$_2$—CH—CH$_2$), 2'-fluoro (2'-F), 2'-amino, 2'-thio, 2'-Omethyl, 2'-methoxymethyl, 2'-propyl, and the like. The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazi-n-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases are known in the art. Certain of these nucleobases are particularly useful for increasing the binding affinity of the oligomeric compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C and are presently preferred base substitutions, even more particularly when combined with 2'-O-methoxyethyl sugar modifications.

Another modification of the antisense oligonucleotides described herein involves chemically linking to the oligonucleotide one or more moieties or conjugates which enhance the activity, cellular distribution or cellular uptake of the oligonucleotide. The antisense oligonucleotides can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes.

Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., dihexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylaminocarbonyloxycholesterol moiety.

Several genes have been found to be associated with pluripotency and suitable for use with the present invention as reprogramming factors. Such genes are known in the art and include, by way of example, SOX family genes (SOX1, SOX2, SOX3, SOX15, SOX18), KLF family genes (KLF1, KLF2, KLF4, KLF5), MYC family genes (C-MYC, L-MYC, N-MYC), SALL4, OCT4, NANOG, LIN28, STELLA, NOBOX or a STAT family gene. STAT family members may include for example STAT1, STAT2, STAT3, STAT4, STAT5 (STAT5A and STAT5B), and STAT6. While in some instances, use of only one gene to induce pluripotency may be possible, in general, expression of more than one gene is required to induce pluripotency. For example, two, three, four or more genes may be simultaneously integrated into the somatic cell genome as a polycistronic construct to allow simultaneous expression of such genes. In an exemplary aspect, four genes are utilized to induce pluripotency including OCT4, SOX2, KLF4 and C-MYC. Additional genes known as reprogramming factors suitable for use with the present invention are disclosed in U.S. patent application Ser. No. 10/997,146 and U.S. patent application Ser. No. 12/289,873, incorporated herein by reference.

All of these genes commonly exist in mammals, including human, and thus homologues from any mammals may be used in the present invention, such as genes derived from mammals including, but not limited to mouse, rat, bovine, ovine, horse, and ape. Further, in addition to wild-type gene products, mutant gene products including substitution, insertion, and/or deletion of several (e.g., 1 to 10, 1 to 6, 1 to 4, 1 to 3, and 1 or 2) amino acids and having similar function to that of the wild-type gene products can also be used. Furthermore, the combinations of factors are not limited to the use of wild-type genes or gene products. For example, Myc chimeras or other Myc variants can be used instead of wild-type Myc.

The present invention is not limited to any particular combination of nuclear reprogramming factors. As discussed herein a nuclear reprogramming factor may comprise one or more gene products. The nuclear reprogramming factor may also comprise a combination of gene products as discussed herein. Each nuclear reprogramming factor may be used alone or in combination with other nuclear reprogramming factors as disclosed herein. Further, nuclear reprogramming factors of the present invention can be identified by screening methods, for example, as discussed in U.S. patent application Ser. No. 10/997,146, incorporated herein by reference. Additionally, the nuclear reprogramming factor of the present invention may contain one or more factors relating to differentiation, development, proliferation or the like and factors having other physiological activities, as well as other gene products which can function as a nuclear reprogramming factor.

The nuclear reprogramming factor may comprise a protein or peptide. The protein may be produced from a gene as discussed herein, or alternatively, in the form of a fusion gene product of the protein with another protein, peptide or the like. The protein or peptide may be a fluorescent protein and/or a fusion protein. For example, a fusion protein with green fluorescence protein (GFP) or a fusion gene product with a peptide such as a histidine tag can also be used. Further, by preparing and using a fusion protein with the TAT peptide derived from the virus HIV, intracellular uptake of the nuclear reprogramming factor through cell membranes can be promoted, thereby enabling induction of reprogramming only by adding the fusion protein to a medium thus avoiding complicated operations such as gene transduction. Since preparation methods of such fusion gene products are well known to those skilled in the art, skilled artisans can easily design and prepare an appropriate fusion gene product depending on the purpose.

The nucleic acid construct of the present invention, such as recombinant vectors may be introduced into a cell using a variety of well known techniques, such as non-viral based transfection of the cell. In an exemplary aspect the construct is incorporated into a vector and introduced into the cell to allow expression of the construct. Introduction into the cell may be performed by any viral or non-viral based transfection known in the art, such as, but not limited to electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as Lipofectamine™, Dojindo Hilymax™, Fugene™, jetPEI™, Effectene™ and DreamFect™.

In various aspects, reprogramming induction efficiency may be increased by 10, 20, 30, 40, 50, 60, 70, 80, 90, 100, 150, 200, 300, 400 or ever 500 percent as compared with convention methods. For example, induction efficiency may be as high as 1, 2, 3, 4, 5, 6, 7, 8, 9, 10, 15, 20, 25 or 50 percent (e.g., percent of induced cells as compared with total number of starting somatic cells).

In various aspects, the somatic cell is contacted with the reprogramming factor about 1, 2, 3, 4, 5, 7, 8, 9, 10, 11, 12, 13, 14 or more days before the cell is contacted with any other agent or inhibitor. In an exemplary aspect, the somatic cell is contacted with the reprogramming factor about 1, 2, 3, 4 or 5 days before the cell is contacted with any other agent or inhibitor.

Further analysis may be performed to assess the pluripotency characteristics of a reprogrammed cell. The cells may be analyzed for different growth characteristics and embryonic stem cell like morphology. For example, cells may be differentiated in vitro by adding certain growth factors known to drive differentiation into specific cell types. Reprogrammed cells capable of forming only a few cell types of the body are multipotent, while reprogrammed cells capable of forming any cell type of the body are pluripotent.

Expression profiling of reprogrammed somatic cells to assess their pluripotency characteristics may also be conducted. Expression of individual genes associated with pluripotency may also be examined. Additionally, expression of embryonic stem cell surface markers may be analyzed. Detection and analysis of a variety of genes known in the art to be associated with pluripotent stem cells may include analysis of genes such as, but not limited to OCT4, NANOG, SALL4, SSEA-1, SSEA-3, SSEA-4, TRA-1-60, TRA-1-81, or a combination thereof. iPS cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-tubulin III; α-smooth muscle actin (α-SMA); fibroblast growth factor 4 (FGF4), Cripto, Dax1; zinc finger protein 296 (Zfp296); N-acetyltransferase-1 (Nat1); ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sall4; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; as well as other general markers for Pluripotency, for example any genes used during induction to reprogram the cell. IPS cells can also be characterized by the down-regulation of markers characteristic of the differentiated cell from which the iPS cell is induced.

The invention further provides iPS cells produced using the methods described herein, as well as populations of such cells. The reprogrammed cells of the present invention, capable of differentiation into a variety of cell types, have a variety of applications and therapeutic uses. The basic properties of stem cells, the capability to infinitely self-renew and the ability to differentiate into every cell type in the body make them ideal for therapeutic uses.

Accordingly, in one aspect the present invention further provides a method of treatment or prevention of a disorder and/or condition in a subject using induced pluripotent stem cells generated using the methods described herein. The method includes obtaining a somatic cell from a subject and reprogramming the somatic cell into an induced pluripotent stem (iPS) cell using the methods described herein. The cell is then cultured under suitable conditions to differentiate the cell into a desired cell type suitable for treating the condition. The differentiated cell may then be introducing into the subject to treat or prevent the condition.

One advantage of the present invention is that it provides an essentially limitless supply of isogenic or synegenic human cells suitable for transplantation. The iPS cells are tailored specifically to the patient, avoiding immune rejection. Therefore, it will obviate the significant problem associated with current transplantation methods, such as, rejection of the transplanted tissue which may occur because of host versus graft or graft versus host rejection. Several kinds of iPS cells or fully differentiated somatic cells prepared from iPS cells from somatic cells derived from healthy humans can be stored in an iPS cell bank as a library of cells, and one kind or more kinds of the iPS cells in the library can be used for preparation of somatic cells, tissues, or organs that are free of rejection by a patient to be subjected to stem cell therapy.

The iPS cells of the present invention may be differentiated into a number of different cell types to treat a variety of disorders by methods known in the art. For example, iPS cells may be induced to differentiate into hematopoetic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition.

Thus, the methods of the present invention may be used to treat a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, Huntington's disease, amyotrophic lateral sclerosis (ALS), lysosomal storage diseases, multiple sclerosis, spinal cord injuries, genetic disorders, and similar diseases, where an increase or replacement of a particular cell type/tissue or cellular de-differentiation is desirable.

In various embodiments, the method increases the number of cells of the tissue or organ by at least about 5%, 10%, 25%, 50%, 75% or more compared to a corresponding untreated control tissue or organ. In yet another embodiment, the method increases the biological activity of the tissue or organ by at least about 5%, 10%, 25%, 50%, 75% or more compared to a corresponding untreated control tissue or organ. In yet another embodiment, the method increases blood vessel formation in the tissue or organ by at least about 5%, 10%, 25%, 50%, 75% or more compared to a corresponding untreated control tissue or organ. In yet another embodiment, the cell is administered directly to a subject at a site where an increase in cell number is desired.

The present invention further provides a method for evaluating a physiological function or toxicity of an agent, compound, a medicament, a poison or the like by using various cells obtained by the methods described herein.

Oct4-GFP mouse embryonic fibroblasts (MEFs) are derived from mice carrying an IRES-EGFP fusion cassette downstream of the stop codon of pou5f1 (Jackson lab, Stock #008214) at D13.5. These MEFs are cultured in DMEM (Invitrogen, 11995-065) with 10% FBS (Invitrogen) plus glutamine and NEAA. For iPSC induction, only MEFs with passage of 0 to 4 are used.

As discussed above, since the discovery of reprogramming of fibroblasts to iPS cells, much effort has been put into overcoming the extreme low efficiency of the process. A few small molecules have been shown to replace some 4F reprogramming factors in large-scale random screens, while only a handful—most of which are chromatin remodeling reagents—have been shown to enhance iPSC generation in 4F-infected cells. To date, TGFβ receptor inhibitors are the only kinase inhibitors shown to be capable of directly enhancing reprogramming and replacing Sox2 and cMyc by inducing Nanog expression, an observation that led to the discovery that the MET is a key event during early reprogramming stages. Thus, identifying kinases functioning in the course of reprogramming could provide not only targets that could be modulated but also provide novel insight into how reprogramming works.

As such the presently invention further provides a kinase inhibitor library screen aimed at identifying additional kinases important for reprogramming. As described herein, inhibition of P38, IP3K and AurkA significantly enhanced reprogramming efficiency, indicating that these kinases could function as barriers to the process. Modulation of activities of these kinases possibly in combination with other currently available methods could substantially increase reprogramming efficiency. Further, the data provided herein identifies novel functional aspects of AurkA, whose kinase activity may inhibit Akt-mediated phosphorylation of GSK3β, which needs to be inactivated to promote iPSC generation.

Figure 13A:
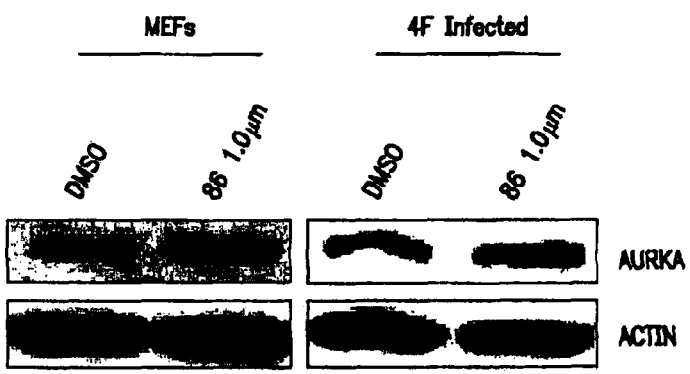
Figure 13B:
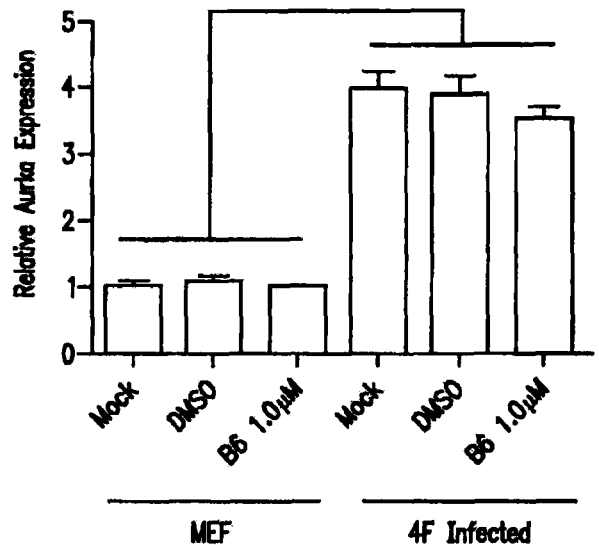
Figure 13C:
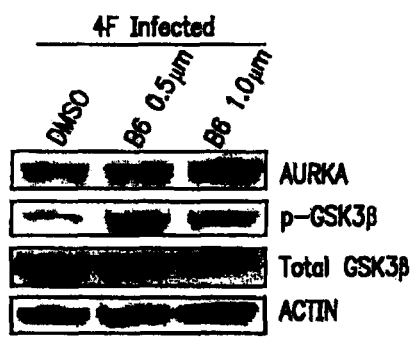
Figure 13D:
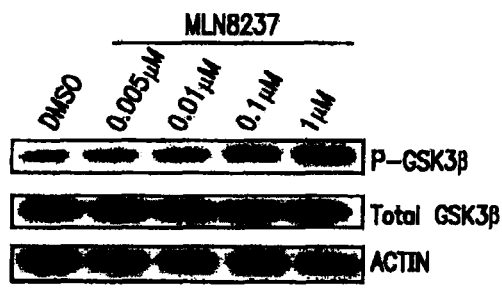
Figure 13E:
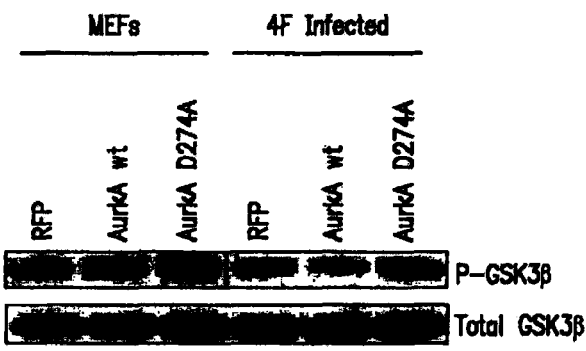

AurkA kinase is well characterized for its role in modulating centrosome function and spindle assembly. Aberrant expression of AurkA, either overexpressed or reduced, also reportedly leads to tumor development. Date presented herein shows that during reprogramming of MEFs to iPS cells, AurkA is highly induced even at an early stage (~day 5 post transduction) (FIG. 13B), an event correlated with reduction of phospho-GSK3β in these cells (FIG. 13E). Modulating AurkA kinase activity could thus affect GSK3β activity and alter reprogramming efficiency. Meanwhile, treatment with AurkA inhibitors could increase levels of AurkA protein. Recent studies indicate that AurkA may have a kinase-independent function, such as stabilizing N-MYC protein by direct binding to block MYC ubiquitination. N-MYC is also specifically expressed in mES or iPS cells, and recent work confirms that levels of endogenous N-MYC increase in reprogramming. Interestingly, N-MYC degradation also requires sequential phosphorylation by cyclin B/Cdk1 and GSK3.

Figure 18:
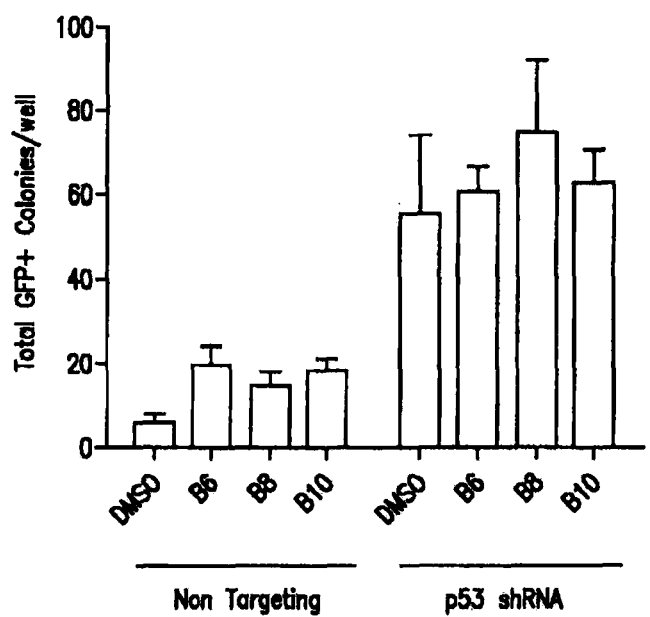
FIG. 18 is a graph plotting total GFP+ colonies. Kinase inhibitors effect on iPSC generation when p53 is silenced by RNAi. MEFs were infected with 4F plus either non-targeting or p53 shRNA. Inhibitor treatments were started at day 3 post-infection. Media were changed every other day, and GFP+ colonies were counted at day 12 post-infection.
Figure 19:
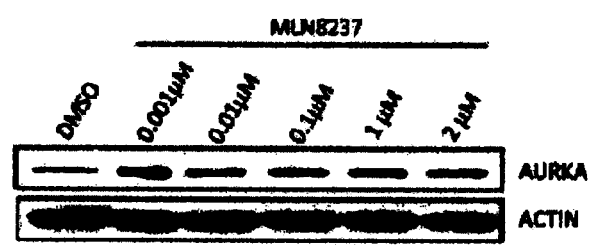
FIG. 19 is a western blot showing MLN8237 increases levels of AurkA protein. 4F-infected MEFs were treated with MLN8237 at various concentrations at day 3 post 4F infection. Cells were harvested 48 hrs after drug treatment for western blotting analysis of AurkA protein. Actin serves as loading control.
Figure 20:
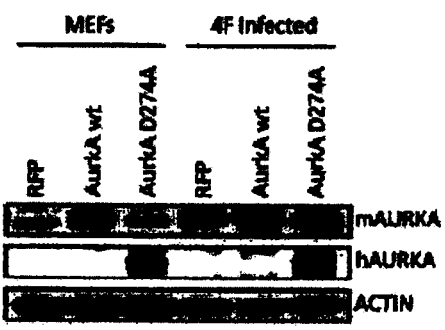
FIG. 20 is a western blot showing overexpression of wt and kinase-dead AurkA in MEFs. MEFs or 4F-infected MEFs were infected with either wild-type (wt) mouse AurkA virus or virus expressing a kinase-dead mutant human AurkA D274A virus at day 0. Cells were harvested at day 5 post-infection for analysis of AurkA proteins. mAURKA refers to wild type mouse AurkA protein and hAURKA refers to kinase-dead mutant of human AurkA protein. Specific antibodies to each protein were used to detect overexpressed proteins.

The screen of the present invention also identified p38 and IP3K as barrier kinases. p38 reportedly regulates diverse processes, including the stress response, chromosome remodeling and the cell cycle. Interestingly, p38 has been shown to have tumor suppressor function, and one target regulated by p38 is p53. This observation could explain why p53 knockdown abolished the enhancing effect of a p38 inhibitor (FIG. 18). Meanwhile, p38 could also negatively regulate cell cycle progression. Although growth effects were detected following inhibitor treatment of 4F-infected cells, the possibility that a small percentage of cells gain a proliferative advantage following inhibition of p38 cannot be ruled out, since very few cells reach a fully reprogrammed state. By contrast, IP3K is the least studied protein identified here as a barrier kinase. Gene expression profiles indicate that MEFs express low levels of IP3K and its expression is induced in partially reprogrammed iPS cells and iPS/mES cells. IP3K functions primarily in calcium-dependent signal transduction and its relationship to reprogramming requires further investigation.

Figure 11A:
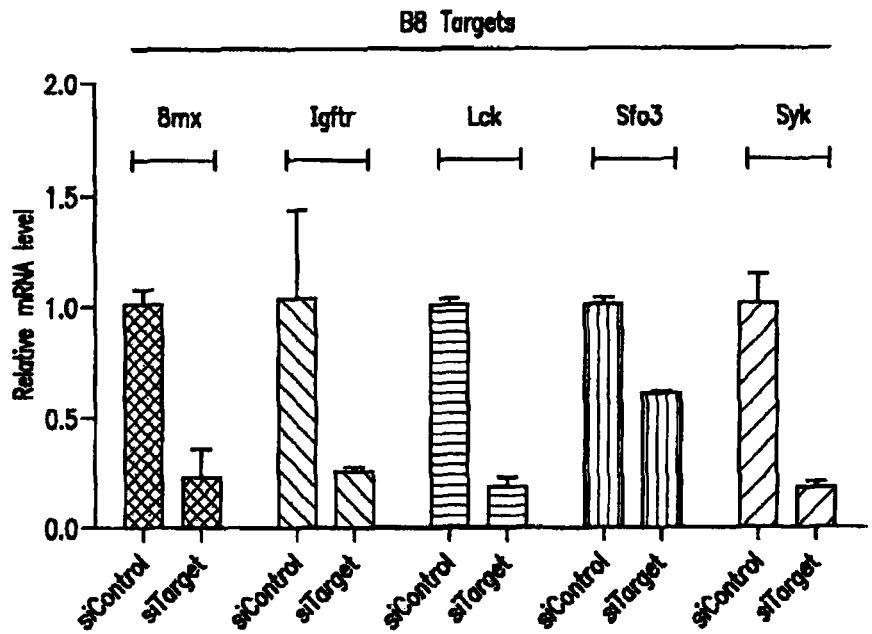
FIGS. 11A-11D are a series of graphical representations depicting inhibitor-targeted kinases confirmed as barrier genes.
Figure 11B:
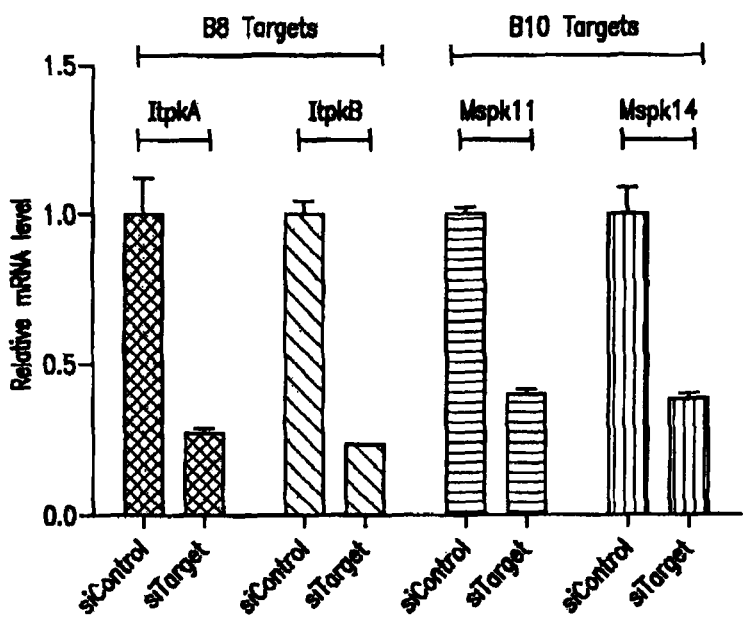
Figure 11C:
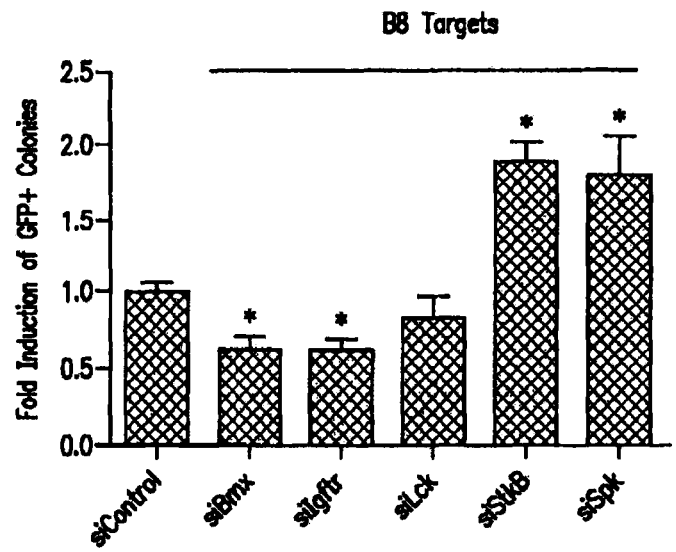

Kinases functioning as potential enhancers of reprogramming were also identified. Specifically, we found that knockdown of the insulin like growth factor (IGF) receptor Igf1r compromised reprogramming (FIG. 11C). Interestingly, IGF signaling reportedly activates the PI3K pathway, which could also activate Akt function. It was also determined that that knockdown of negative regulators of IGF signaling enhances reprogramming (data not shown). These findings suggest an important role for Akt function in iPSC generation. Although we found that the kinase inhibitors could enhance iPSCs generation and the reprogrammed cells reached fully pluripotent state, but the exact nature of cells population to increase iPSCs was not obvious. For example, expression of four factors (OSKM) can lead a cell population to the path of pluripotency but not all of them reach fully iPSC state because a large number of unstable or partially reprogrammed cells never go over the barrier to fully reprogrammed state.

The findings presented herein provide new insights into how somatic cells are reprogrammed into iPS cells and have identified new barrier genes that could serve as targets to design specific chemical inhibitors. For example, barrier genes include those of Table 1 below.

Accordingly, the invention provides a method of screening for a modulator of somatic cell reprogramming. The method includes: a) contacting a cell of a reporter cell line for somatic cell reprogramming with one or more nuclear reprogramming factors; b) contacting the cell of (a) with a test agent; c) detecting a reporter of the cell which is indicative of pluripotency; d) comparing the level of the reporter with that of a corresponding cell not contacted with the test agent, wherein a test agent that increases or decreases the level of the reporter as compared to the level of the reporter in the corresponding cell is identified as a modulator of somatic cell reprogramming. Screening approaches to identify agents that specifically act to modulate, e.g., increase or decrease somatic cell reprogramming efficiency are described herein.

It will be understood that any of the methods described herein may be adapted to a high throughput screening (HTS) method. A "hit" indicates an agent that is capable of modulating, e.g., increasing or decreasing induction efficiency.

As discussed throughout, an agent useful in any of the methods of the invention can be any type of molecule, for example, a polynucleotide, a peptide, a peptidomimetic, peptoids such as vinylogous peptoids, chemical compounds, such as organic molecules or small organic molecules, or the like, and can act in any of various ways to modulate induction of pluripotency. In one aspect, an agent identified by the method of the present invention is a small molecule chemical compound. Compounds of the invention can be modified and derivatized at multiple functional groups to enhance pharmacokinetic, pharmacodynamic, and biochemical properties. Such methods are commonly known to those of skill in the art.

Test agents encompass numerous chemical classes, though typically they are chemical compounds, such as an organic molecule, and often are small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The screening methods of the present invention may employ vectors useful for generating reporter cell lines which include the entire gene of interest of which expression is to be determined, or any portion thereof, such as the promoter. A "promoter" is a nucleic acid sequence that directs the binding of RNA polymerase and thereby promotes RNA synthesis. Promoter sequences include constitutive and inducible promoter sequences which may be endogenous or exogenous to the cell type. In various aspects, exemplary promoter sequences may include endogenous promoters of nuclear reprogramming factors, such as Oct4, c-Myc, Sox2, Nanog and Klf-4 gene promoters. The promoters can be either naturally occurring promoters, hybrid promoters, or synthetic promoters. Hybrid promoters, which combine elements of more than one promoter, are also known in the art, and are useful in the present invention.

The vectors employed in the present invention may include a reporter gene/protein or reporter molecule to facilitate detecting the transcriptional activity of the gene of interest, such as the Oct4 gene. For example, the present invention contemplates construction of promoter/reporter constructs which may be used to generate transgenic reporter cell lines. There are many genes and molecules that may be used in such a fashion, as well as methods of labeling known to those of ordinary skill in the art. Examples of the types of reporters known in the art include genes encoding enzymes, as well as fluorescent and chemiluminescent proteins. The reporter gene can be visibly observable or detectable using conventional detection techniques. In one embodiment promoter/reporter construct includes a promoter operably linked to a reporter gene encoding a protein, such as green fluorescent protein (GFP), or recombinantly produced enhanced GFP (eGFP) operably linked to an Oct4 promoter. Such vectors are useful for generating transgenic reporter cell lines which may be used to quantify efficiency of induction to a pluripotent state.

A nucleic acid is "operably linked" when it is placed into a functional relationship with another nucleic acid sequence. For example, DNA for a promoter or enhancer is operably linked to a coding sequence if it affects the transcription of the sequence. Generally, "operably linked" means that the DNA sequences being linked are contiguous in reading phase.

The screening methods of the present invention may be performed on a number of platforms and utilize a variety of cell types. The method of the present invention may be performed, for example, using a cell based assay. A variety of cells may be used, those known in the art and those commercially available, as well as those isolated from a subject. In an exemplary aspect somatic cells are utilized. Additionally, the method may be performed using cells transfected with a promoter/reporter construct, such as described in the Examples and above. As such, the method is particularly suited to be performed in a high-throughput fashion, (i.e., 96 or 384-well plate analysis; mechanical or robotic processing).

The screening strategy of the present invention may employ a cell line including a nucleic acid encoding a promoter/reporter construct. In various embodiments, the reporter protein is luciferase (LUC), β-lactamase, chloramphenicol acetyltransferase (CAT), adenosine deaminase (ADA), aminoglycoside phosphotransferase (neo, G418), dihydrofolate reductase (DHFR), hygromycin-B-phosphotransferase (HPH), thymidine kinase (TK), β-galactosidase (β-gal), and xanthine guanine phosphoribosyltransferase (XGPRT), or a fluorescent protein. In exemplary embodiments, the reporter protein is GFP or eGFP.

The green fluorescent protein (GFP) is composed of 238 amino acids (26.9 kDa), originally isolated from the jellyfish *Aequorea victoria* that fluoresces green when exposed to blue light. Enhanced green fluorescent protein (eGFP) is a 29 kDa recombinantly produced protein with Ex/Em=488/507 nm derived from GFP including mutations such as, the (F64L) point mutation to enhance fluorescence.

A number of additional fluorescent proteins are known in the art and suitable for use with the present invention, including but not limited to blue fluorescent proteins (e.g., EBFP, EBFP2, Azurite, mKalama1), cyan fluorescent proteins (e.g., ECFP, Cerulean, CyPet) and yellow fluorescent proteins (e.g., YFP, Citrine, Venus, YPet).

In various aspects, screening includes comparing induction efficiency of a sample including cells contacted with a test compound to that of corresponding sample including cells not contacted with the test agent, e.g., a control. This is performed by comparing the level of reporter present in the sample contacted with the test agent (e.g., test sample) to that of the control. For example, the amount of cells detected by fluorescence may be determined in both the control and test sample and compared. In various aspects, a test agent is identified as a modulator of reprogramming when the induction efficiency is increased by 10, 20, 30, 40, 50, 60, 70, 80, 90, 100, 150, 200, 300, 400 or ever 500 percent as compared with the number of somatic cells initially induced, or alternatively the control. For example, induction efficiency may be as high as 1, 2, 3, 4, 5, 6, 7, 8, 9, 10, 15, 20, 25 or 50 percent (e.g., percent of induced cells as compared with total number of starting somatic cells).

The following examples are provided to further illustrate the embodiments of the present invention, but are not intended to limit the scope of the invention. While they are typical of those that might be used, other procedures, methodologies, or techniques known to those skilled in the art may alternatively be used. Representative embodiments are also illustrated in Exhibit A, which is herein incorporated by reference in its entirety.

Example 1

Mouse Embryonic Fibroblast Reprogramming

293FT cell culture and lentiviral infection: 293FT cells cultured in a growth medium (DMEM, 10% FBS, 500 µg/ml G418) are seeded in 96-well (primary screen) or 24-well plates (secondary and tertiary screens) at $2.2 \times 10^4$ cells or $1.32 \times 10^5$ cells per well, respectively, and incubated at 37° C., 5% $CO_2$ for subsequent lentiviral infection. The RNAi Consortium (TRC) mouse kinase activity lentiviral shRNA library is purchased from ThermoScientific (RMM4957). 293FT cells are transfected with pLKO.1 plasmid DNA-expressing shRNAs targeting the mouse kinase gene family using Lipofectamine™ 2000 according to the manufacture's instructions. On the following day (Day 2), the medium is replaced with fresh 293FT medium containing 1.1% BSA, and the cells are incubated at 37° C., 5% $CO_2$ for an additional two days for lentivirus production. On Day 4, 40 µl (96-well) or 200 µl (24-well) of lentivirus-containing medium is transferred to the retrovirus-infected MEF plates (iD-3).

Oct4-GFP mouse embryonic fibroblasts (MEFs): MEFs are isolated from e13.5 embryos from Oct4-GFP mice (Jackson Lab, #008214) {Lengner, 2007 #32} and used (up to passage 4) for induction of pluripotent stem cells. Oct4-GFP MEFs are maintained in a growth medium (DMEM, 10% FBS, L-glutamine, MEM-NEAA). With slight modification, retrovirus production and induction of iPSCs are performed following the Takahashi et al. protocol (Takahashi et al. 2007 *Cell* 131:861). To generate retroviruses carrying four factors (Oct3/4, Sox2, Klf4, or c-Myc), Plat-E cells are cultured in a growth medium (DMEM, 10% FBS) and seeded in 100-mm plates one day prior to transfection. Nine micrograms of pMXs plasmid DNA-expressing Oct3/4, Sox2, Klf4, or c-Myc (Addgene) are used to transfect Plat-E cells using Lipofectamine and Plus reagent (Invitrogen) according to the manufacturer's instructions. On the following day (Day 3), the medium is replaced with fresh Plat-E medium, and the cells are incubated at 37° C., 5% $CO_2$ for an additional day for retrovirus production. In addition, Oct4-GFP MEFs are seeded on 100-mm plates at $1 \times 10^6$ cells for retroviral infection.

TABLE 1

Kinases identified as confirmed hits.

| No. | Gene Symbol | Accession ID | Cluster | No. | Gene Symbol | Accession ID | Cluster |
|---|---|---|---|---|---|---|---|
| 1 | BUB1B | NM_009773 | Mm.29133 | 31 | 6330514 A18RIK | NM_183152 | Mm.17613 |
| 2 | RAK3 | NM_028679 | Mm.146194 | 32 | NPR2 | NM_173788 | Mm.103477 |
| 3 | BMPR2 | NM_007561 | Mm.7106 | 33 | BMP2K | NM_080708 | Mm.281490 |
| 4 | IRAK2 | NM_172161 | Mm.152142 | 34 | EIF2AK2 | NM_011163 | Mm.378990 |
| 5 | LIMK2 | NM_010718 | Mm.124176 | 35 | MOS | NM_020021 | Mm.459300 |
| 6 | BMPR1A | NM_009758 | Mm.237825 | 36 | NEK2 | NM_010892 | Mm.33773 |
| 7 | TESK1 | NM_011571 | Mm.10154 | 37 | NEK6 | NM_021606 | Mm.143818 |
| 8 | PRKCA | NM_011101 | Mm.222178 | 38 | PLK1 | NM_011121 | Mm.16525 |
| 9 | MAPK1 | NM_011949 | Mm.196581 | 39 | PLK2 | NM_152804 | Mm.380 |
| 10 | SRPK1 | NM_016795 | Mm.15252 | 40 | RNASEL | NM_011882 | Mm.259254 |
| 11 | RAGE | NM_011973 | Mm.140948 | 41 | SCYL1 | NM_023912 | Mm.276063 |
| 12 | AATK | NM_007377 | Mm.6826 | 42 | TBK1 | NM_019786 | Mm.34580 |
| 13 | EPHA5 | NM_007937 | Mm.137991 | 43 | TLK2 | NM_011903 | Mm.126976 |
| 14 | CDC2L6 | NM_198164 | Mm.200924 | 44 | UHMK1 | NM_010633 | Mm.389214 |
| 15 | DDR1 | NM_007584 | Mm.5021 | 45 | RPS6KB1 | NM_028259 | Mm.374825 |
| 16 | JAK1 | NM_146145 | Mm.289657 | 46 | AK3 | NM_021299 | Mm.196067 |
| 17 | EPHA1 | NM_023580 | Mm.133330 | 47 | DGKE | NM_019505 | Mm.153695 |
| 18 | SNF1LK | NM_010831 | Mm.290941 | 48 | PIK3C2G | NM_011084 | Mm.391538 |
| 19 | PIM2 | NM_138606 | Mm.347478 | 49 | GALK2 | NM_175154 | Mm.20216 |
| 20 | FRAP1 | NM_020009 | Mm.21158 | 50 | NME1 | NM_008704 | Mm.439702 |
| 21 | DAPK2 | NM_010019 | Mm.335252 | 51 | GTF2F1 | NM_133801 | Mm.24632 |
| 22 | TRIB3 | NM_175093 | Mm.276018 | 52 | PAX8 | NM_011040 | Mm.2533 |
| 23 | DAPK3 | NM_007828 | Mm.10294 | 53 | PKIG | NM_011106 | Mm.10091 |
| 24 | CAMKV | NM_145621 | Mm.274540 | 54 | PIK3R5 | NM_177320 | Mm.244960 |
| 25 | STK25 | NM_021537 | Mm.28761 | 55 | GIT2 | NM_019834 | Mm.195632 |
| 26 | MAP2K1 | NM_008927 | Mm.248907 | 56 | PIK3AP1 | NM_031376 | Mm.222266 |
| 27 | PAK7 | NM_172858 | Mm.131572 | 57 | CNKSR3 | NM_172546 | Mm.37984 |
| 28 | STK24 | NM_145465 | Mm.390756 | 58 | PKIB | NM_008863 | Mm.262135 |

TABLE 1-continued

Kinases identified as confirmed hits.

| Gene No. | Symbol | Accession ID | Cluster | Gene No. | Symbol | Accession ID | Cluster |
|---|---|---|---|---|---|---|---|
| 29 | CSNK2B | NM_009975 | Mm.378901 | 59 | PER2 | NM_011066 | Mm.218141 |
| 30 | KHK | NM_008439 | Mm.22451 | 60 | FASTKD5 | NM_198176 | Mm.27090 |

On Day 4, MEF growth medium is aspirated from the MEF plates, and 20 ml of a mixture of equal parts of the medium containing Oct3/4, Sox2, Klf4, and c-Myc-retroviruses with 4 μg/ml polybrene is used to infect MEFs (infection Day 0, iD-0). After 24 hours (iD-1), the virus-/polybrene-containing medium is replaced with fresh MEF medium, and infected MEFs are incubated at 37° C., 5% $CO_2$. On Day 2 post-infection (iD-2), infected MEFs are re-seeded onto either 48-well plates (primary screen) or 12-well plates (secondary and tertiary screenings) at $1 \times 10^4$ cells or $4 \times 10^4$ cells per well, respectively, and incubated in MEF medium at 37° C., 5% $CO_2$ for subsequent lentiviral infection.

On Day 3 prior to lentivirus infection (iD-3), the MEF medium is replaced with an appropriate volume of fresh MEF medium (160 μl in 48-well plates and 1.8 ml in 12-well plates) containing polybrene at a concentration that brought the final concentration of 4 μg/ml after addition of the lentivirus-containing medium.

TABLE 2

RT-qPCR primer sequences for kinases identified as confirmed hits in the iPSC induction assay during primary screening.

| | | |
|---|---|---|
| mmuDGKE | forward | 5'-gtattctgcaggcagcagtg-3' (SEQ ID NO: 1) |
| | reverse | 5'-gtcttctggcaccaaatgc-3' (SEQ ID NO: 2) |
| mmuPLK2 | forward | 5'-catcaccaccattcccact-3' (SEQ ID NO: 3) |
| | reverse | 5'-tcgtaacactttgcaaatcca-3' (SEQ ID NO: 4) |
| mmuTESK1 | forward | 5'-ggctcccttgacatacaatca-3' (SEQ ID NO: 5) |
| | reverse | 5'-aagaggtctgaccggttc-3' (SEQ ID NO: 6) |
| mmuBMP2K | forward | 5'-ccgtccctttcatttctcac-3' (SEQ ID NO: 7) |
| | reverse | 5'-ttggagaatgttccgtcgtt-3' (SEQ ID NO: 8) |
| mmuBMPR2 | forward | 5'-gagccctcccttgacctg-3' (SEQ ID NO: 9) |
| | reverse | 5'-gtatcgacccccgtccaatc-3' (SEQ ID NO: 10) |
| mmuMAPK1 | forward | 5'-aagaactcattttgaagagactgc-3' (SEQ ID NO: 11) |
| | reverse | 5'-ctctgagcccttgtcctga-3' (SEQ ID NO: 12) |
| mmuE-Cadherin | forward | 5'-aacaactgcatgaaggcgggaatc-3' (SEQ ID NO: 13) |

TABLE 2-continued

RT-qPCR primer sequences for kinases identified as confirmed hits in the iPSC induction assay during primary screening.

| | | |
|---|---|---|
| | reverse | 5'-cctgtgcagctggctcaaatcaaa-3' (SEQ ID NO: 14) |

To determine the roles of mouse kinases in reprogramming, lentivirus-containing media collected from infected 293FT cell cultures are added to the MEF plates (40 μl per well in 48-well plates and 200 μl per well in 12-well plates) on iD-3. On the following day, the media is replaced with fresh MEF medium; from Day 5 onward, the medium is replaced with mES growth medium [DMEM, 15% FBS, LIF, monothioglycerol (MTG), L-glutamine, MEM-NEAA] every other day until GFP+ colony counting and picking (iD14 to 18).

To generate iPS clones after lentiviral shRNA-mediated knockdown of targeted kinases, GFP+ iPS colonies are picked from infected MEF cultures between Days 16 and 18, trypsinized and resuspended in mES medium, and plated on 12-well plates with an irradiated MEF feeder layer (prepared a day prior to picking colonies). After several passages, iPS clones are seeded on 24-well plates with feeder layers for immunostaining.

RT-qPCR: On Day 4 of lentiviral infection, MEF cells undergoing reprogramming are rinsed with 1× phosphate-buffered saline (PBS) and total RNAs are extracted from the cells using Trizol (Invitrogen) following the manufacturer's instructions. RNA is then reverse-transcribed into cDNA using SuperScript™ III (Invitrogen) and random hexamer primers (Promega). One RNA sample of each preparation is processed without SuperScript III™ RT as a negative control in subsequent real-time PCR reactions. Quantitative PCR reactions are performed using SYBR Green mix and Lightcycler 480 II (Roche). DGKε, PLK2, TESK1, BMP2K, BMPR2, MAPK1, and E-Cadherin expression are detected using cDNA amplified with corresponding primer sets. All qPCR reactions are run in duplicate and tested with three independent experiments. Average Ct values are used for quantification of target gene expression levels, and RNA samples extracted from non-targeting shRNA (NT) or pLKO.1 control infections are used to set a relative 100% expression level. Table 2 shows primers used for the RT-qPCR.

Immunoblotting: On Day 4 of lentiviral infection, cells are rinsed with 1×PBS, trypsinized, and harvested by centrifugation at 1,000 rpm for 5 minutes at 4° C. Cell pellets are resuspended in ice-cold M-PER cell lysis buffer (ThermoScientific) with 1× protease-phosphatase inhibitor cocktail (ThermoScientific) and incubated for 15 minutes at 4° C. with gentle agitation. Cell lysates are then centrifuged at 14,000×g for 15 minutes at 4° C., and supernatants are transferred to a cold 1.7 ml tube.

After protein concentrations are determined using Dc Protein assay (Bio-Rad), 80 μg of total cell extracts are resolved on a 4-20% gradient precast SDS-PAGE gel (Lenzo), semi-dry transferred onto a PVDF membrane, and immunoblotted with the following antibodies: anti-TESK1 (Abcam, ab92707), anti-GAPDH (Abcam, ab8245), anti-cofilin (Cell Signaling, #3318), anti-phospho-cofilin (Cell Signaling, #3313S), anti-rabbit IgG-HRP (Cell Signaling, #7074), and goat anti-mouse IgG-HRP (GE Health, NA9310). Following a secondary antibody incubation, proteins are visualized using BM Chemiluminescence Western Blotting Substrate (POD) (Roche, 11500708001). The reproducibility of lentiviral shRNA knockdown is verified multiple times (5×3).

Example 2

Differentiation from iPS Cells

In Vitro Differentiation: To induce spontaneous differentiation of iPSCs, iPS clones that show ES-like proliferation and morphology undergo embryoid body formation using the hang-drop method. CCE ES cells. A mouse embryonic stem cell line (StemCell Technologies), is used as a control. On Day 3, embryoid bodies are transferred to gelatin-coated 6-well plates and cultured with EB medium (DMEM, 15% FBS, MEM-NEAA, L-Glutamine, MTG) for another 11 days. On Day 14, cells are fixed with 4% paraformaldehyde for immunostaining with the following antibodies: anti-AFP (Abcam, ab7751), anti-Beta III tubulin (R&D systems, MAB1368), and anti-alpha actinin (Sigma, A7811).

Immunostaining: Established iPSC clones are fixed in 4% paraformaldehyde and permeablized by 0.1% Triton-X-100 in PBS. Cells are then blocked in 5% BSA in PBS containing 0.1% Triton X-100 for 1 hour at room temperature. Primary antibody is diluted from 1:100 to 1:400 in 2.5% BSA PBS containing 0.1% Triton X-100, according to the manufacturer's suggestion. Secondary antibody is diluted 1:400 and cells are stained for 45 minutes at room temperature. Antibodies used are: anti-mNanog (Bethyl Lab, IHC00205), and anti-h/mSSEA1 (R&D systems, MAB2156).

MEF cells are plated on 0.1% gelatin-coated 12-well plates and transfected with 50 nM siRNA by Lipofectamine-2000 following manufacturer's protocol. After 72 hours, cells are fixed in 3.75% formaldehyde in PBS for 15 minutes on ice and permeabilized in 0.5% Triton X-100 in PBS. After blocking with 3% milk in PBS for 30 minutes, cells are stained for F-actin with rhodamine-conjugated phalloidin (Bitium Inc., #00027) at 1:40 dilution or Hoechst 33342, trihydrochloride, trihydrate (Invitrogen, H3570) at 1:5,000 dilution.

For following the cytoskeletal re-arrangement during reprogramming, MEF cells are plated in 12 well plates at $4 \times 10^4$ cells/well. One day later, cells are transduced with 4-factor virus (for reprogramming, as described above) followed by lentivirus medium containing shRNAs targeting either mouse TESK1 or LIMK2 kinases or the lentivirus medium containing the empty vector backbone only (pLKO.1). Lentivirus is produced in 293FT cells, as described above. To follow the actin cytoskeleton assembly, cells are fixed either immediately after addition of the lentivirus (Day 0) or at Day 2, 4, or 6, and immunostained with rhodamine-conjugated phalloidin, as stated above. For immunoblot analysis, cell lysates are collected from Days 2, 4, and 6, and blotted for phospho and total cofilin antibodies.

Teratoma formation: iPSCs are trypsinized and resuspended in EB medium at a concentration of $1 \times 10^6$ cells/ml. 150 µl of iPSCs are injected subcutaneously into the dorso-caudal end of nude mice after they are anesthetized with Avertin. Teratomas are visible after 1 week and surgically removed around 3-4 weeks; they are fixed in zinc formalin solution overnight and washed three times with PBS the next day. Samples are further submitted to histology facility for H&E staining.

Example 3

Function of Kinases for Somatic Cell Reprogramming

Figure 1B:
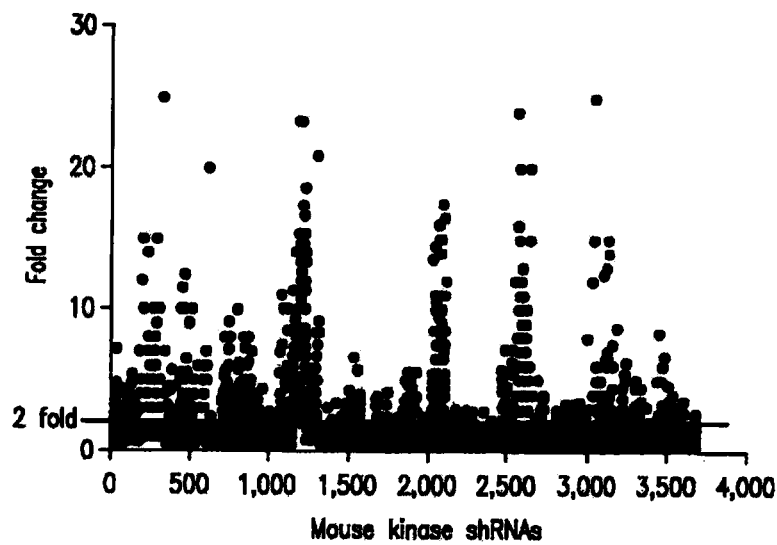
Figure 2A:
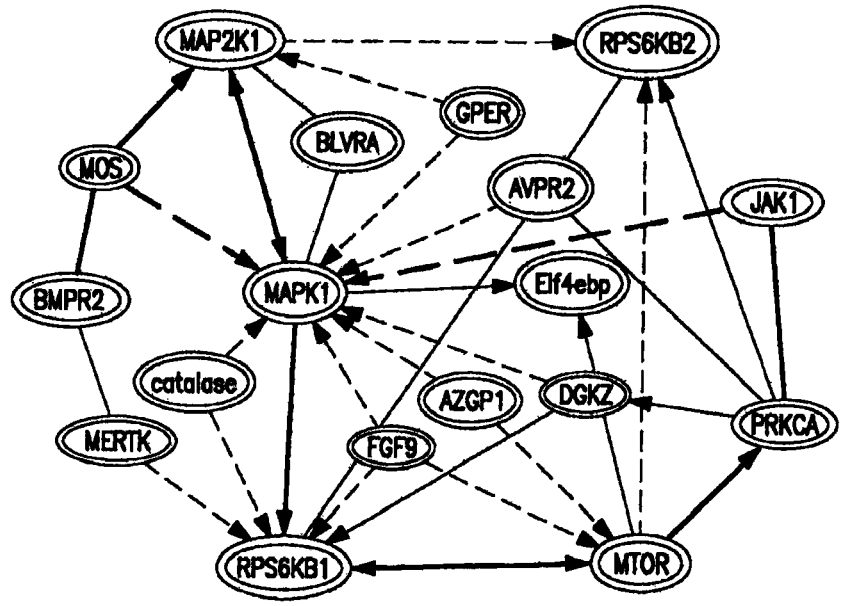
FIGS. 2A-2C show that network analysis reveals four highly interconnected functional associations. The 59 kinase genes, confirmed by tertiary screen and identified as barriers for reprogramming, are evaluated for interactions with various biological functional networks using the Ingenuity Pathways Knowledge Base (IPKB) analysis.
Figure 2A:
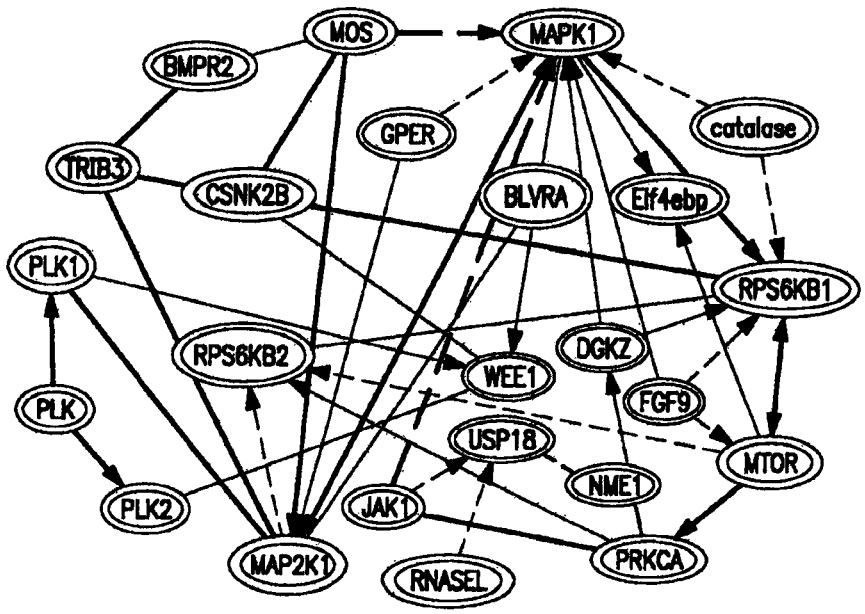
Figure 2B:
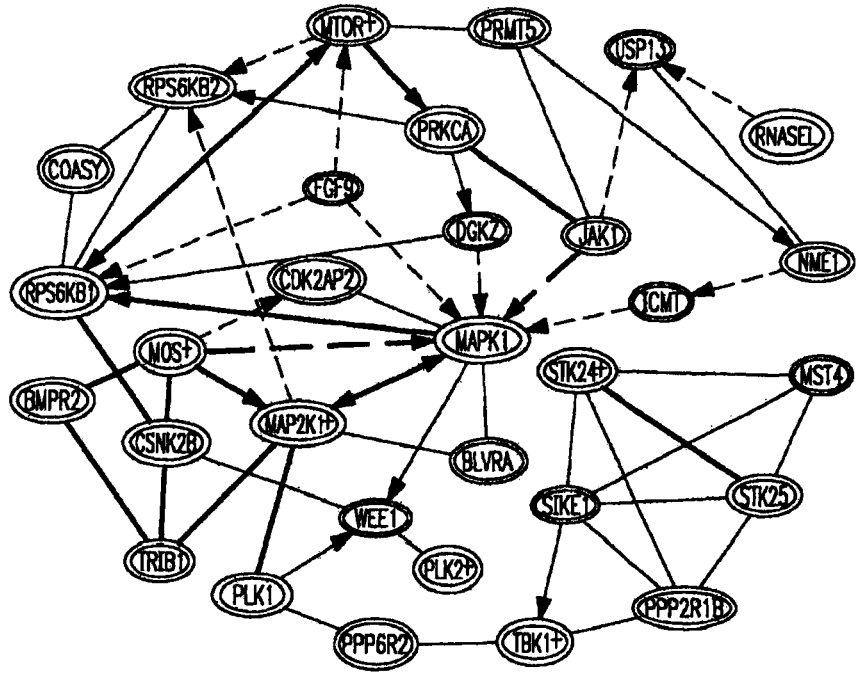
Figure 2B:
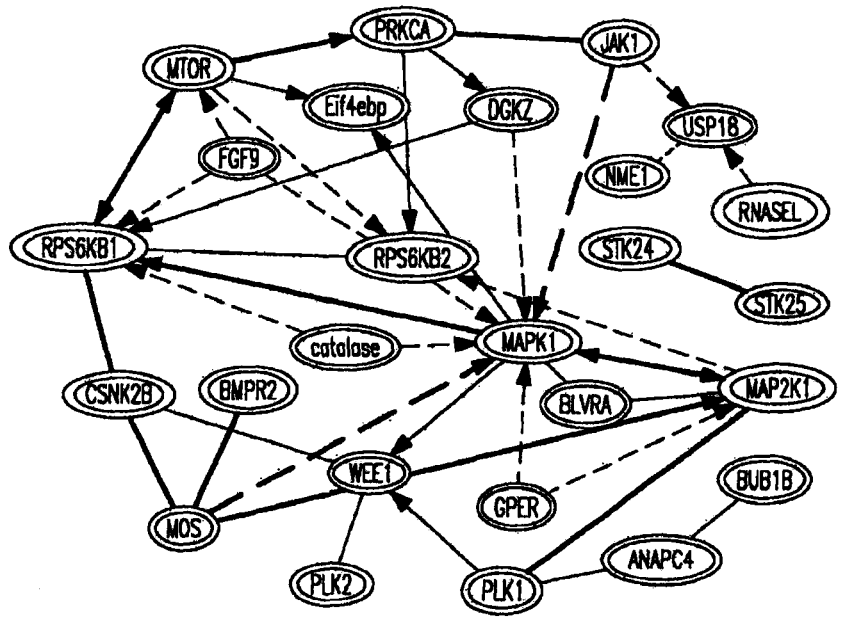
Figure 2C:
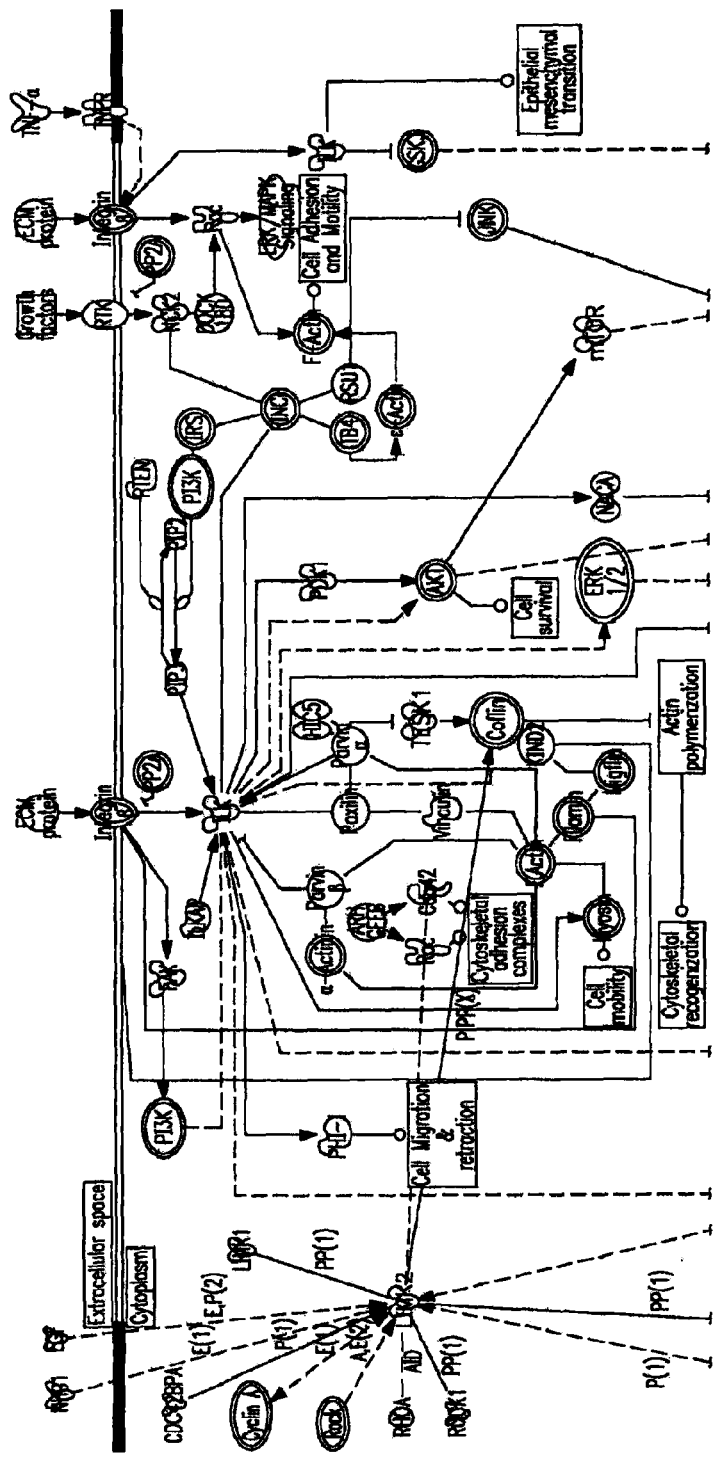
Figure 2C:
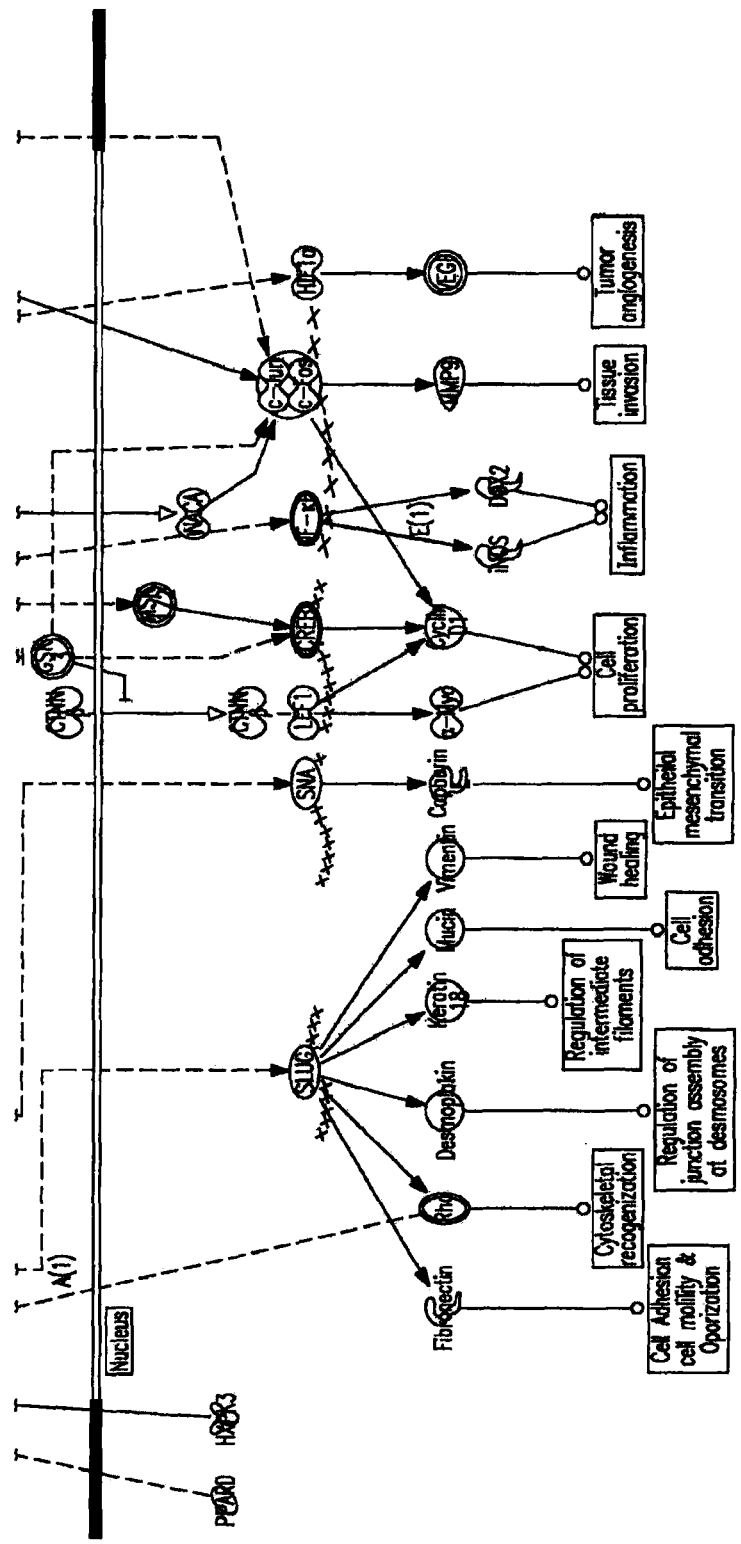

To determine the function of kinases that regulate somatic cell reprogramming to iPSCs, the present invention provides a whole kinome RNAi screen (FIG. 1). Mouse embryonic fibroblast (MEF) stably integrated POU5F1 (OCT4)-driven GFP construct is used as a reporter cell line to quantitatively monitor iPSC generation. Oct4-GFP MEFs are transduced with a retrovirus of four pluripotency factors, Oct4, Sox2, Klf4, and c-Myc (OSKM), and GFP colonies are quantified. Using OCT4-GFP MEFs, a lentiviral shRNA library targeting 734 kinase genes covering the entire mouse kinome is screened. 3,686 shRNA lentiviruses are prepared in 293FT cells and individually screened in iPSC generation assays (FIG. 1). Dot-plot represents the results of the primary screen, where GFP+ colony counts are shown as fold changes after normalization with that of control pLKO lentiviral infected cells.

Figure 7:
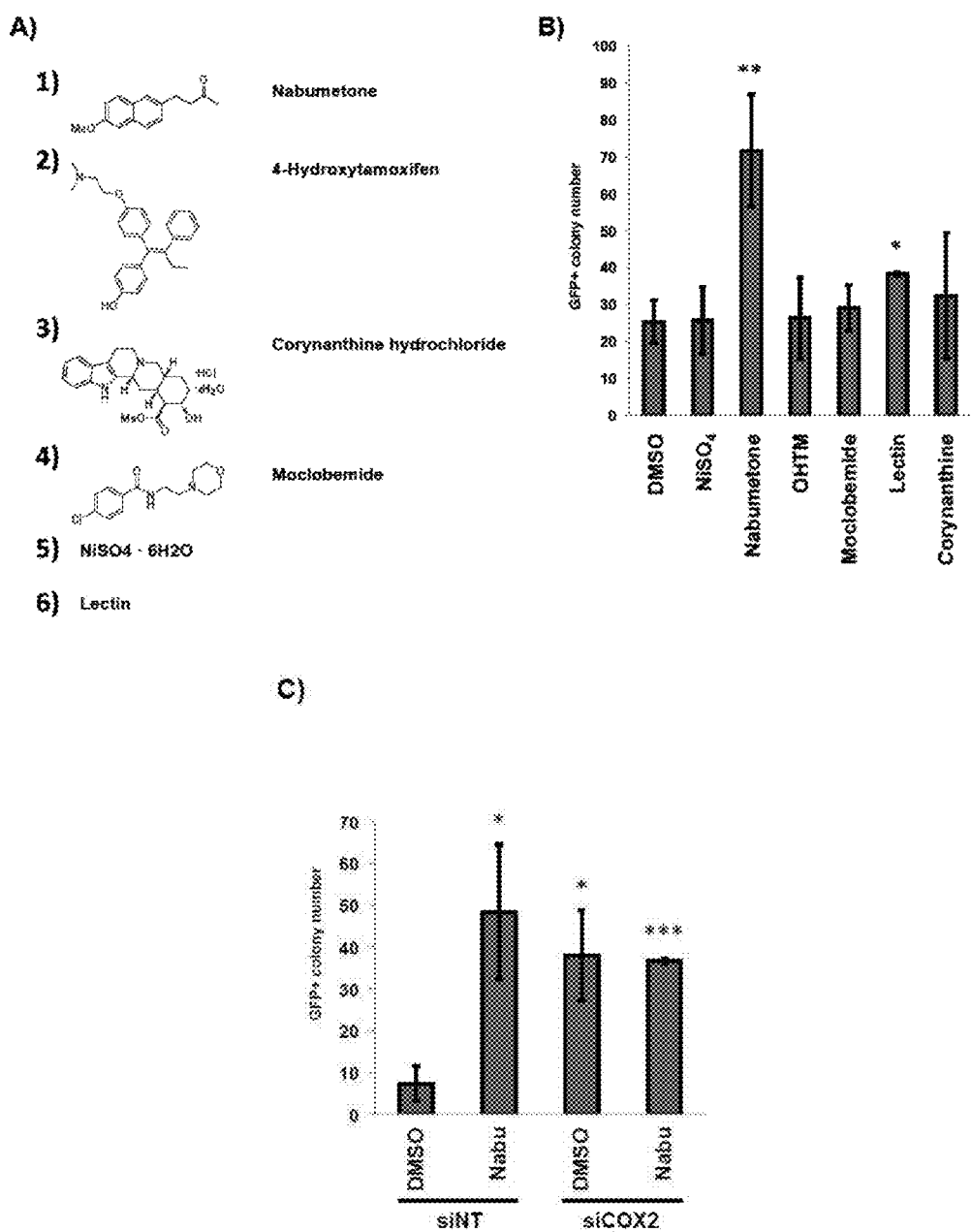
FIG. 7A displays the structures of six small molecules used in iPS cell reprogramming.
FIG. 7B is a plot of GFP+ colony number showing effects on reprogramming efficiency. Error bars represent standard deviations of three independent experiments. *p value<0.05; **p value<0.005.
FIG. 7C is a plot of GFP+ colony number at day 12~14. Error bars represent standard deviations of six independent experiments. *p value<0.05; p value<0.005; *p value<0.0005. siNT serves as control.
Figure 8:
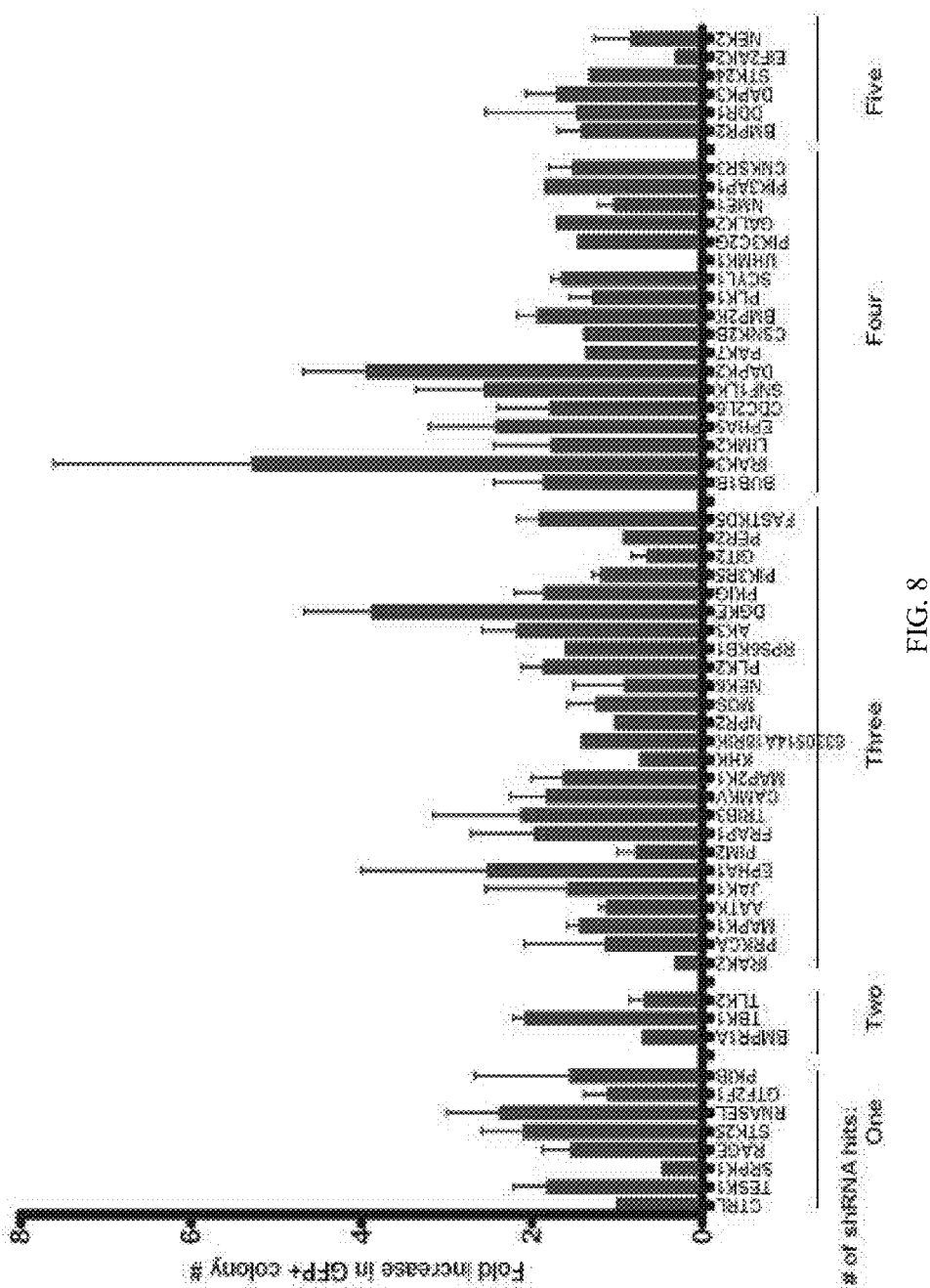
FIG. 8 shows identification of kinases acting as barriers for iPSC generation. Kinase genes identified as hits in primary screen are further confirmed by secondary and tertiary screens. After the primary screen (see FIG. 1), kinase genes are grouped by numbers of shRNA targeting a single gene that led to a 2-fold increase in GFP+ colony numbers. The kinases that are targeted by at least two shRNAs are chosen as candidates for further analysis. For kinases targeted with only a single shRNA, a threshold of 6-fold increase in GFP+ colony number is used. 157 genes (288 shRNAs) are tested in the secondary screen, and 60 genes (77 shRNAs) followed in the tertiary screen. Several kinases, including BMP2K, BMPR2, and MAPK1, which are previously shown to have regulatory roles in pluripotency and reprogramming, are identified.

A 2-fold enhancement in iPSC generation by a kinase knockdown is designated as a hit that resulted in the identification of 152 primary hits. Further analysis of the primary screen is performed as follows: 2-5 constructs of shRNAs targeting a single kinase that resulted in at least a 2-fold increase in GFP+ are considered to be hits as barrier kinases. The barrier kinase identification threshold is increased to a 6-fold increase in GFP+ colonies when a single shRNA targeted a kinase gene. Next, a secondary validation screen of 152 genes is performed in duplicate in a 12-well format and 59 hits are obtained (Tables 1 and 3). Then, 59 genes are further validated in a tertiary screen in 12-well format in duplicate and repeated five times (FIG. 7). A number of previously known kinases are identified such as BMP2K, BMPR2, and MAPK1 that regulate pluripotency and the reprogramming process.

TABLE 3

Kinases identified as primary hits.

| no | Gene Symbol | Accession ID | Cluster | no | Gene Symbol | Accession ID | Cluster |
|---|---|---|---|---|---|---|---|
| 1 | MAP3K14 | NM_016896 | Mm.158981 | 81 | BRD2 | NM_010238 | Mm.3444 |
| 2 | BUB1 | NM_009772 | Mm.2185 | 82 | HUNK | NM_015755 | Mm.125874 |
| 3 | BUB1B | NM_009773 | Mm.29133 | 83 | PHKG1 | NM_011079 | Mm.3159 |
| 4 | TGFBR1 | NM_009370 | Mm.197552 | 84 | STK25 | NM_021537 | Mm.28761 |
| 5 | ACVRL1 | NM_009612 | Mm.279542 | 85 | MAP3K1 | NM_011945 | Mm.15918 |

TABLE 3-continued

Kinases identified as primary hits.

| no | Gene Symbol | Accession ID | Cluster | no | Gene Symbol | Accession ID | Cluster |
|---|---|---|---|---|---|---|---|
| 6 | ACVR1 | NM_007394 | Mm.689 | 86 | MAP4K4 | NM_008696 | Mm.19073 |
| 7 | RIPK3 | NM_019955 | Mm.46612 | 87 | MAP4K5 | NM_024275 | Mm.291936 |
| 8 | IRAK3 | NM_028679 | Mm.146194 | 88 | MAP2K1 | NM_008927 | Mm.248907 |
| 9 | RIPK1 | NM_009068 | Mm.374799 | 89 | PAK7 | NM_172858 | Mm.131572 |
| 10 | TESK2 | NM_146151 | Mm.425201 | 90 | STK24 | NM_145465 | Mm.390756 |
| 11 | RIPK2 | NM_138952 | Mm.112765 | 91 | MAP3K6 | NM_016693 | Mm.36640 |
| 12 | BMPR2 | NM_007561 | Mm.7106 | 92 | CSNK2B | NM_009975 | Mm.378901 |
| 13 | IRAK2 | NM_172161 | Mm.152142 | 93 | PRPF4B | NM_013830 | Mm.10027 |
| 14 | IRAK4 | NM_029926 | Mm.422858 | 94 | KHK | NM_008439 | Mm.22451 |
| 15 | LIMK2 | NM_010718 | Mm.124176 | 95 | NPR2 | NM_173788 | Mm.103477 |
| 16 | B230120H23RIK | NM_023057 | Mm.314618 | 96 | 4930444A02RIK | NM_029037 | Mm.17631 |
| 17 | BC021891 | NM_145608 | Mm.216458 | 97 | 6330514A18R1K | NM_183152 | Mm.17613 |
| 18 | BMPR1A | NM_009758 | Mm.237825 | 98 | TTK | NM_009445 | Mm.1904 |
| 19 | TESK1 | NM_011571 | Mm.10154 | 99 | BMP2K | NM_080708 | Mm.281490 |
| 20 | MAP3K12 | NM_009582 | Mm.172897 | 100 | CAMKK1 | NM_018883 | Mm.9998 |
| 21 | MAP3K9 | NM_177395 | Mm.436861 | 101 | EIF2AK2 | NM_011163 | Mm.378990 |
| 22 | PRKCA | NM_011101 | Mm.222178 | 102 | GSG2 | NM_010353 | Mm.42045 |
| 23 | SGK2 | NM_013731 | Mm.26462 | 103 | MOS | NM_020021 | Mm.459300 |
| 24 | CDKL3 | NM_153785 | Mm.280557 | 104 | NEK2 | NM_010892 | Mm.33773 |
| 25 | ANKK1 | NM_172922 | Mm.119994 | 105 | NEK6 | NM_021606 | Mm.143818 |
| 26 | CDK3 | NM_027165 | Mm.33677 | 106 | NEK8 | NM_080849 | Mm.23788 |
| 27 | MAPK1 | NM_011949 | Mm.196581 | 107 | NEK9 | NM_145138 | Mm.29071 |
| 28 | CLK1 | NM_009905 | Mm.1761 | 108 | PDIK1L | NM_146156 | Mm.22778 |
| 29 | SRPK1 | NM_016795 | Mm.15252 | 109 | PLK1 | NM_011121 | Mm.16525 |
| 30 | RAGE | NM_011973 | Mm.140948 | 110 | PLK2 | NM_152804 | Mm.380 |
| 31 | AATK | NM_007377 | Mm.6826 | 111 | PLK3 | NM_013807 | Mm.259022 |
| 32 | EPHA5 | NM_007937 | Mm.137991 | 112 | RNASEL | NM_011882 | Mm.259254 |
| 33 | CDC2L6 | NM_198164 | Mm.200924 | 113 | SCYL1 | NM_023912 | Mm.276063 |
| 34 | ITK | NM_010583 | Mm.339927 | 114 | TBK1 | NM_019786 | Mm.34580 |
| 35 | LTK | NM_206941 | Mm.1740 | 115 | TLK2 | NM_011903 | Mm.126976 |
| 36 | DDR1 | NM_007584 | Mm.5021 | 116 | TRP53RK | NM_023815 | Mm.330796 |
| 37 | JAK1 | NM_146145 | Mm.289657 | 117 | UHMK1 | NM_010633 | Mm.389214 |
| 38 | EPHB2 | NM_010142 | Mm.250981 | 118 | WNK1 | NM_198703 | Mm.333349 |
| 39 | NTRK1 | XM_283871 | Mm.80682 | 119 | ROCK2 | NM_009072 | Mm.276024 |
| 40 | FRK | NM_010237 | Mm.332432 | 120 | RPS6KB1 | NM_028259 | Mm.374825 |
| 41 | FGFR1 | NM_010206 | Mm.265716 | 121 | STK38L | NM_172734 | Mm.322121 |
| 42 | ABL1 | NM_009594 | Mm.1318 | 122 | CDC2L1 | NM_007661 | Mm.267410 |
| 43 | BLK | NM_007549 | Mm.3962 | 123 | SPHK2 | NM_020011 | Mm.24222 |
| 44 | MET | NM_008591 | Mm.86844 | 124 | AK3 | NM_021299 | Mm.196067 |
| 45 | EGFR | NM_007912 | Mm.8534 | 125 | DGKE | NM_019505 | Mm.153695 |
| 46 | ROS1 | NM_011282 | Mm.236163 | 126 | ADK | NM_134079 | Mm.188734 |
| 47 | BMX | NM_009759 | Mm.504 | 127 | PIK3C2G | NM_011084 | Mm.391538 |
| 48 | EPHB1 | NM_173447 | Mm.22897 | 128 | GALK2 | NM_175154 | Mm.20216 |
| 49 | EPHA1 | NM_023580 | Mm.133330 | 129 | NME1 | NM_008704 | Mm.439702 |
| 50 | ZAP70 | NM_009539 | Mm.8038 | 130 | TK1 | NM_009387 | Mm.2661 |
| 51 | EPHA8 | NM_007939 | Mm.1390 | 131 | PCK1 | NM_011044 | Mm.266867 |
| 52 | ROR2 | NM_013846 | Mm.342774 | 132 | STK10 | NM_009288 | Mm.8235 |
| 53 | EPHA10 | NM_177671 | Mm.171490 | 133 | CDKN1A | NM_007669 | Mm.195663 |
| 54 | NTRK3 | NM_008746 | Mm.33496 | 134 | CCND3 | NM_007632 | Mm.246520 |
| 55 | PTK2 | NM_007982 | Mm.254494 | 135 | HUS1 | NM_008316 | Mm.42201 |
| 56 | MATK | NM_010768 | Mm.2918 | 136 | BRSK2 | NM_029426 | Mm.274868 |
| 57 | FGFR2 | NM_010207 | Mm.16340 | 137 | CDKN2D | NM_009878 | Mm.29020 |
| 58 | CSNK1G3 | NM_152809 | Mm.368668 | 138 | DBF4 | NM_013726 | Mm.292470 |
| 59 | FLT4 | NM_008029 | Mm.3291 | 139 | GTF2F1 | NM_133801 | Mm.24632 |
| 60 | TTBK2 | NM_080788 | Mm.275698 | 140 | PAX8 | NM_011040 | Mm.2533 |
| 61 | RYK | NM_013649 | Mm.335391 | 141 | CCNB1 | NM_172301 | Mm.260114 |
| 62 | CSNK1D | NM_027874 | Mm.216227 | 142 | AKAP3 | NM_009650 | Mm.87748 |
| 63 | ADCK4 | NM_133770 | Mm.124728 | 143 | AKAP10 | NM_019921 | Mm.274404 |
| 64 | TSSK2 | NM_009436 | Mm.310201 | 144 | PRKCDBP | NM_028444 | Mm.3124 |
| 65 | STK40 | NM_028800 | Mm.440269 | 145 | PKIG | NM_011106 | Mm.10091 |
| 66 | STK33 | XM_358897 | Mm.389950 | 146 | PIK3R5 | NM_177320 | Mm.244960 |
| 67 | SNF1LK | NM_010831 | Mm.290941 | 147 | GIT2 | NM_019834 | Mm.195632 |
| 68 | PRKCM | NM_008858 | Mm.133719 | 148 | PICK1 | NM_008837 | Mm.259464 |
| 69 | PIM3 | NM_145478 | Mm.400129 | 149 | PIK3AP1 | NM_031376 | Mm.2 |
| 70 | PIM2 | NM_138606 | Mm.347478 | 150 | CNKSR3 | NM_172546 | Mm.37984 |
| 71 | PDK4 | NM_013743 | Mm.235547 | 151 | AKAP8L | NM_017476 | Mm.281005 |
| 72 | PASK | NM_080850 | Mm.379454 | 152 | PER2 | NM_011066 | Mm.218141 |
| 73 | MYLK | NM_139300 | Mm.33360 | 153 | FASTKD5 | NM_198176 | Mm.27090 |
| 74 | MKNK2 | NM_021462 | Mm.42126 | | | | |
| 75 | MELK | NM_010790 | Mm.268668 | | | | |
| 76 | MARK3 | NM_022801 | Mm.425769 | | | | |
| 77 | FRAP1 | NM_020009 | Mm.21158 | | | | |
| 78 | DCLK1 | NM_019978 | Mm.458341 | | | | |

TABLE 3-continued

Kinases identified as primary hits.

| Gene no | Gene Symbol | Accession ID | Cluster | Gene no | Gene Symbol | Accession ID | Cluster |
|---|---|---|---|---|---|---|---|
| 79 | DAPK2 | NM_010019 | Mm.335252 | | | | |
| 80 | CAMKID | NM_177343 | Mm.191949 | | | | |

Figure 5A:
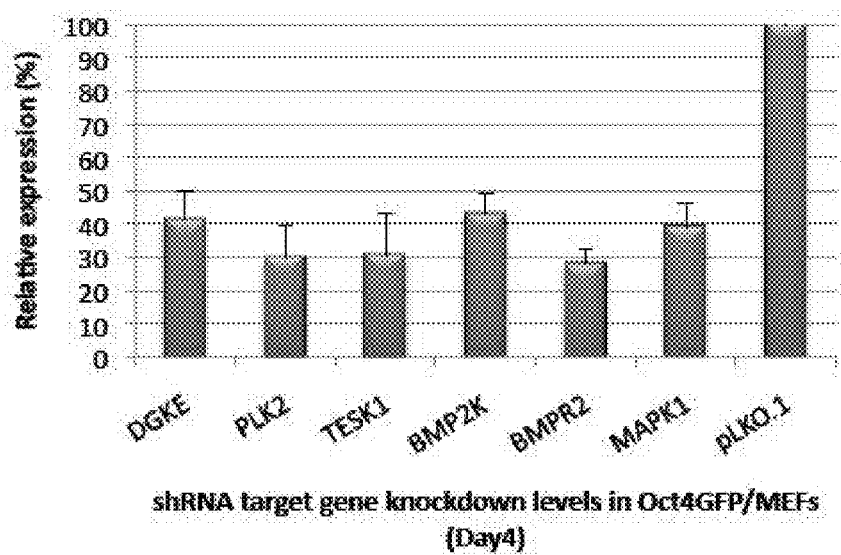
FIGS. 5A-5C show that silencing of six kinases (DGKε, PLK2, TESK1, BMP2K, BMPR2, MAPK1) enhances iPSC generation by promoting mesenchymal-to-epithelial transition (MET) step during reprogramming.
Figure 5B:
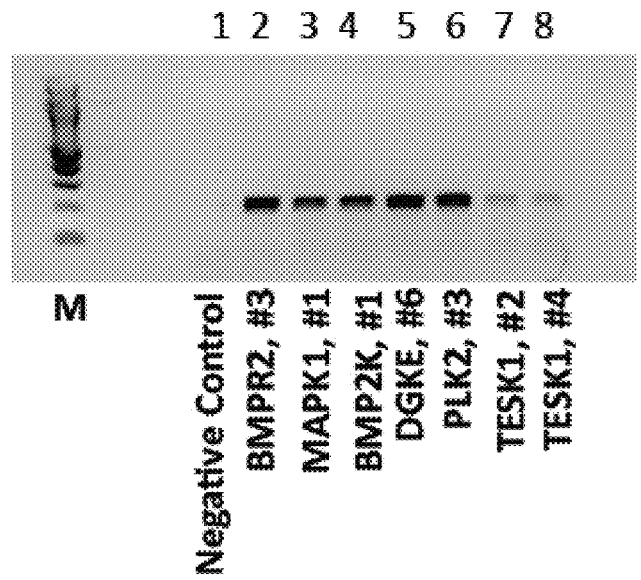
Figure 5C:
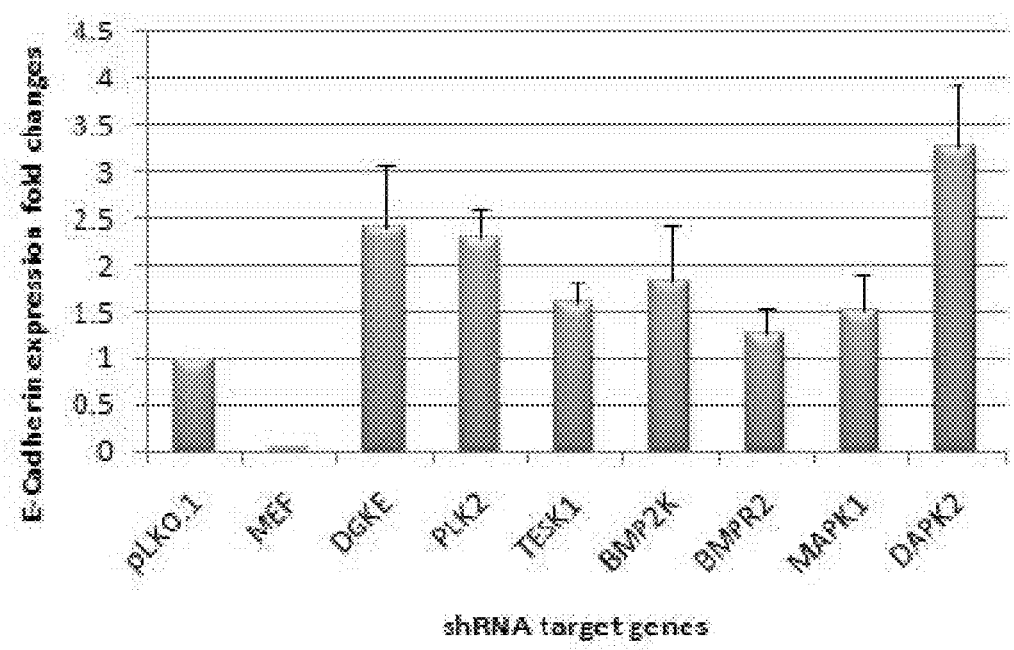
Figure 6A:
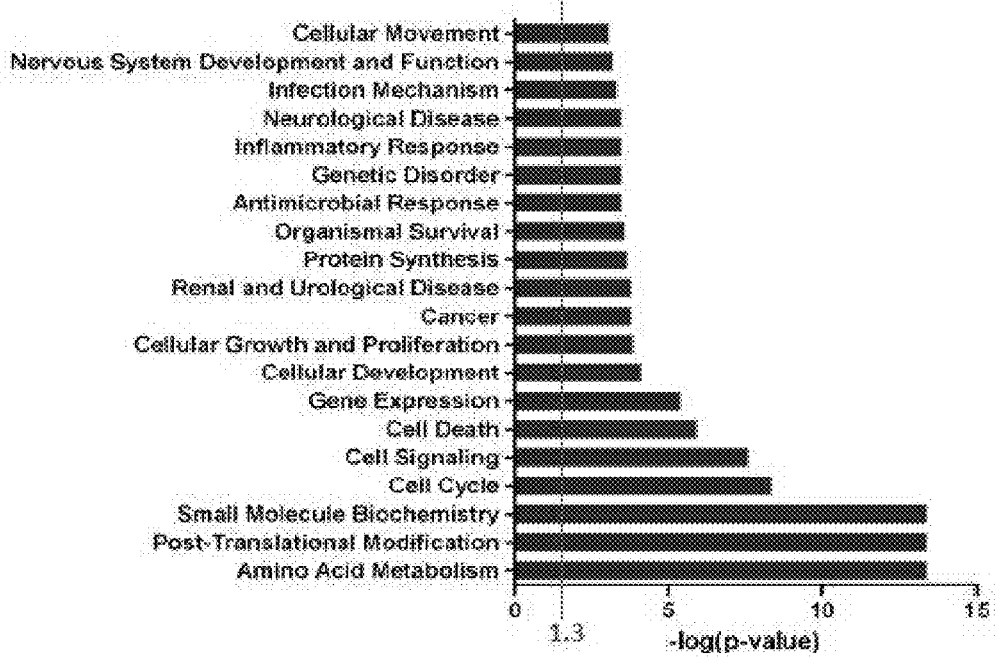
FIGS. 6A-6C show global Molecular Network analysis of 60 kinase genes. Molecular functions (FIG. 6A) and canonical pathways (FIG. 6B) that are statistically significant and overrepresented among 60 genes are determined using IPA (Ingenuity System version 8.7). P-values are calculated using the right-tailed Fisher's exact test, and a p-value of <0.05 is used to set a threshold 1.3 (red line). Top 20 functions and pathways are shown here.
Figure 6B:
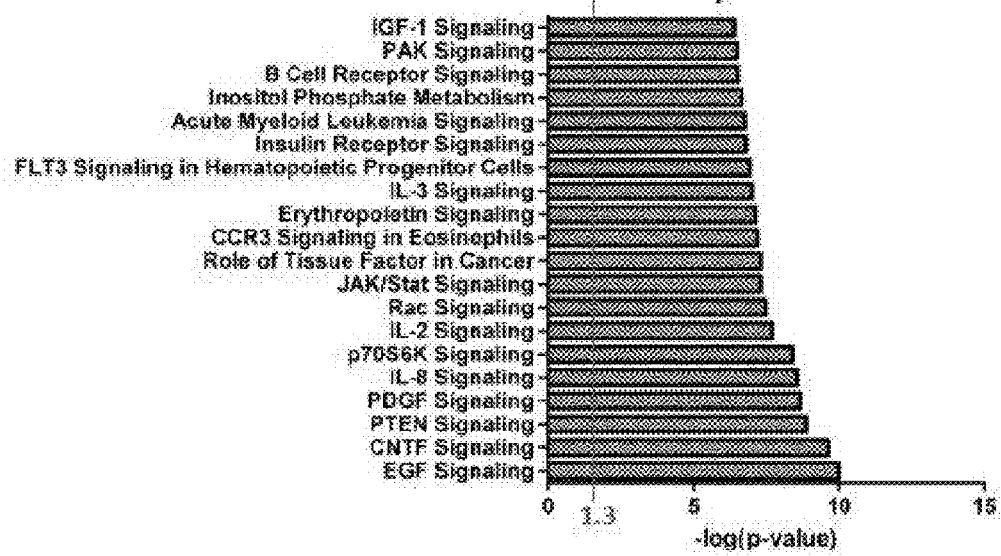
Figure 6C:
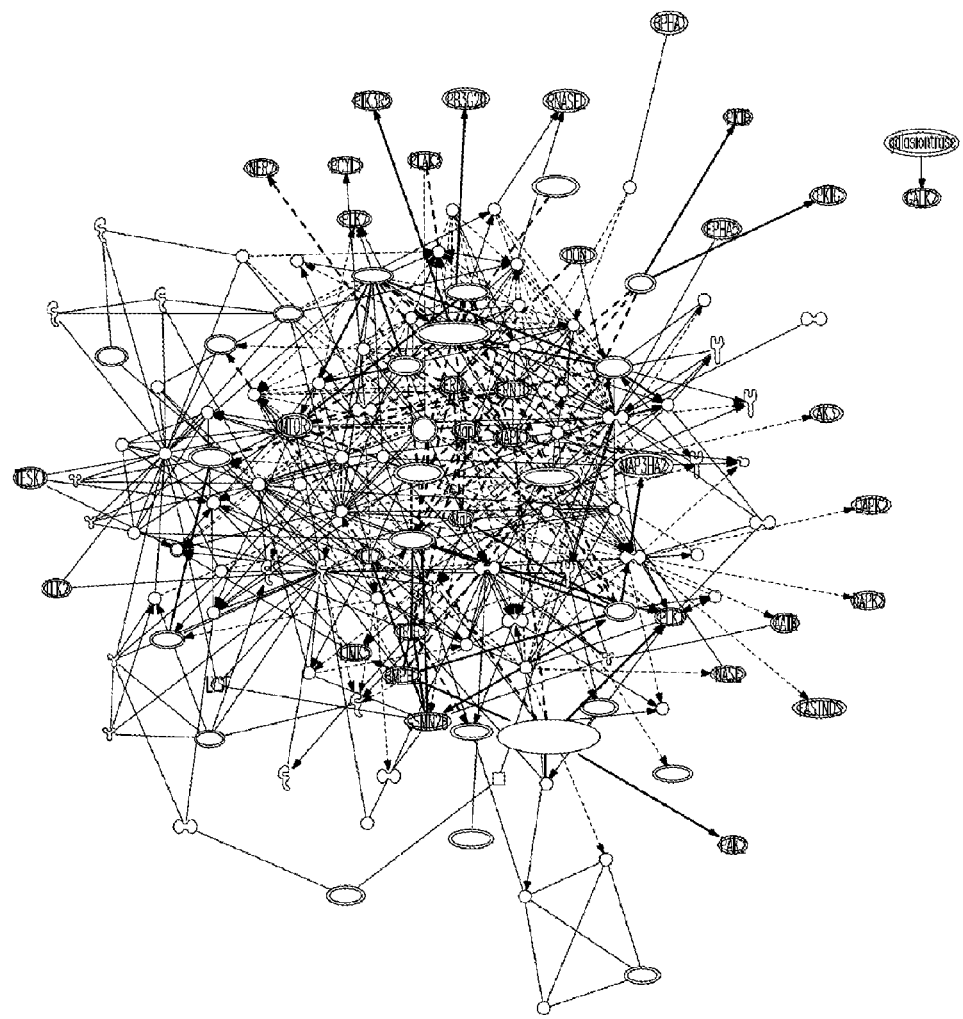

Molecular functions and canonical pathways that are statistically significant and overrepresented among the 59 kinase genes are determined using IPA (Ingenuity System version 8.7) (FIG. 5). P-values are calculated using the right-tailed Fisher's exact test, and a p-value of <0.05 is used to set a threshold 1.3. The top 20 molecular functions and pathways are presented in FIG. 5. Next, network analysis of these 59 kinase genes is carried out for interactions with various biological functional networks using the Ingenuity Pathways Knowledge Base (IPKB) system that reveals four highly interconnected functional associations (FIG. 2).

Using the top ten highly interconnected molecular functions identified with IPKB analysis (FIG. 5), four networks are identified: (I) Amino Acid Metabolism, Post-Translational Modification, Small Molecule Biochemistry; (II) Gene Expression and Cellular Development; (III) Cell Cycle, Cell Signaling, Cell Death; (IV) Cellular Growth and Proliferation, Cancer. Various modes of interactions and function in the networks are highlighted in FIG. 2. To obtain a composite picture of sixty kinases, the four functional associations described in FIG. 2 are merged to generate a global network (FIG. 5). Thus, the present invention provides that the screen has identified the functions of kinases involved in diverse sets of cellular functions playing important roles in iPSC generation.

Example 4

Barrier Kinases Regulate Diverse Biological Functions

Six kinases from Example 3 are selected that regulate diverse biological functions (Table 4): DGKε, PLK2, TESK1, BMP2K, BMPR2, and MAPK1. The function of BMP2K, BMPR2, and MAPK1 as barriers to iPSC generation has been shown; therefore, further characterization of these three kinases in iPSCs can serve as positive controls. The specific role of DGKε, PLK2, and TESK1 in regulating stem cell biology or iPSC generation remains unknown.

During the path to pluripotency and the establishment of a successful ES-like colony, integrin-mediated interactions between cells and their extracellular environment can play important roles in facilitating iPSC generation. Integrin-linked kinase (ILK) acts as an adaptor with essential functions during mouse development. ILK forms a ternary complex with PINCH and Parvin in setting an integrin-signaling platform that interconnects the actin cytoskeleton with diverse signaling pathways. The analysis of the ILK signaling network by IPKB system shows that six out of sixty kinases identified as barriers in iPSC generation are involved in the ILK signaling network (FIG. 2). Intriguingly, TESK1 and LIMK2 modulate cytoskeleton reorganization via cofilin phosphorylation and inactivation. In order to study this organization more thoroughly, the mechanism of TESK1 in iPSC generation is investigated in greater detail below.

iPSC clones obtained by silencing six kinases, DGKε, PLK2, TESK1, BMP2K, BMPR2, and MAPK1, are characterized and the transition step for iPSC is determined. First, the shRNA knockdown is confirmed by RT-qPCR and genomic integration of shRNA by PCR. Second, since a mesenchymal-to-epithelial transition (MET) is required during the initial stage of reprogramming, E-Cadherin expression is used as the marker to determine whether shRNAs targeting 6 kinases facilitated this step of iPSC generation. (E-Cadherin has been shown to be one of the most important genes for MET). In doing so, an overall increase of E-Cadherin expression can be detected in all of the six kinase knockdown samples; however, a varying degree of E-Cadherin increase is observed where DGKε, PLK2, and DAPK2 result in an increase of >2 fold. Thus, the present invention provides that knockdown of the selected six kinases promotes reprogramming of MEFs to iPSCs and modulate MET transition in the initiation reprogramming step.

TABLE 4

Functions of six barrier genes in iPS cell generation.

| | | Biological Functions* | microRNAs^ |
|---|---|---|---|
| DGKε | Molecular function | Diacylglycerol kinase activity; ATP binding; Nucleotide and protein binding; Transferase activity. | — |
| | Role in cell | Long-term potentiation; Activation of protein kinase C activity by G-protein coupled receptor protein signaling pathway | |
| PLK2 | Molecular function | Protein serine/threonine kinase activity; Signal transducer activity; ATP binding; Polo kinase activity; Nucleotide and protein binding | miR10a, miR27b, miR30a, miRn339 |
| | Role in cell | Apoptosis; Degradation in survival and growth; S phase; Positive regulation of I-kappaB kinase/NF-kappaB cascade | |
| TESK1 | Molecular function | Protein serine/threonine kinase activity; Protein tyrosine kinase activity; ATP binding; Transferase activity; Metal ion binding; ILK signaling | miR127, miR196a1, miR196a2, miR196b, miRn338 |
| | Role in cell | Formation; Cell spreading; Its protein kinase domain is most closely related to those of the LIM motif-containing protein kinases (LIMKs); Expressed in testicular germ cells; Outgrowth | |
| BMP2K | Molecular function | Protein serine/threonine kinase activity; ATP binding; Transferase activity; Phosphatase regulator activity | — |

TABLE 4-continued

Functions of six barrier genes in iPS cell generation.

| | | Biological Functions* | microRNAs^ |
|---|---|---|---|
| | Role in cell | BMPs play a key role in skeletal development and patterning; Expression is increased during BMP-2 induced differentiation and the gene product contains a nuclear localization signal. | |
| BMPR2 | Molecular function | Receptor activity; Transforming growth factor beta receptor activity; Protein serine/threonine kinase activity; ATP binding; Transferase activity | — |
| | Role in cell | Mesoderm formation; Positive regulation of endothelial cell proliferation; Transmembrane receptor protein serine/threonine kinase activity; Anterior/posterior pattern formation; Positive regulation of pathway-restricted SMAD protein phosphorylation; Negative regulation of cell growth; Positive regulation of BMP signaling | |
| MAPK1 | Molecular function | Phosphotyrosine binding; Protein serine/threonine kinase activity; ATP binding; Transferase activity; DNA binding; MAP kinase activity; MAP kinase 2 activity | miR125a, miR145, miR149, miR202, miR320a |
| | Role in cell | Nuclear translocation of MAPK; Induction of apoptosis; Response to stress; Response to DNA damage stimulus; Cell cycle; Signal transduction; Positive regulation of cell migration; Positive regulation of cell proliferation; Negative regulation of cell differentiation | |

*Biological functions of six kinases are determined using GO annotations: Molecular functions and Role in cell. Six kinases listed are: DGKε (NM_019505), PLK2 (NM_152804), TESK1 (NM_011571), BMP2K (NM_080708), BMPR2 (NM_007561), MAPK1 (NM_011949).
^MicroRNAs predicted to target these genes are listed.

Example 5

IPS Cells Differentiate into Different Cells

Figure 3A:
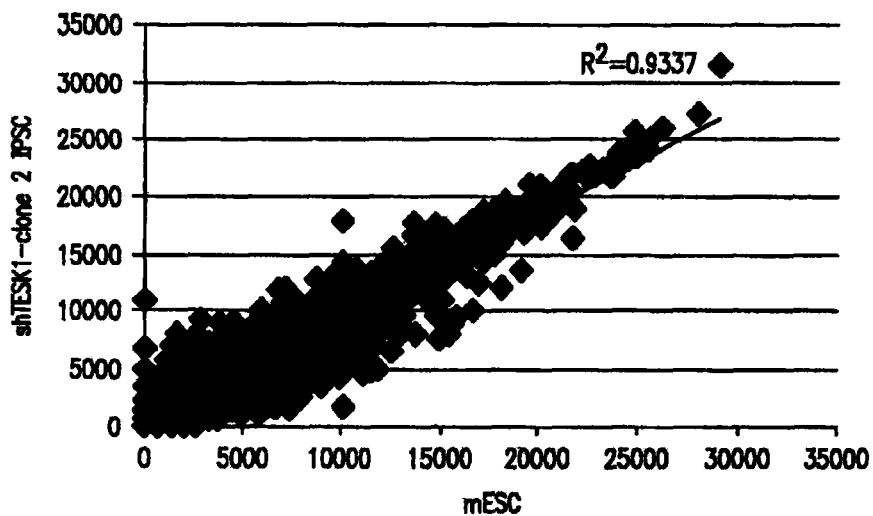
FIGS. 3A-3B show that shTESK1-iPSCs show a similar gene expression profile as mES cells. Genome-wide mRNA expression of shTESK1-iPSCs (FIG. 3A) is compared with mES cells and MEF controls (FIG. 3B).
Figure 3B:
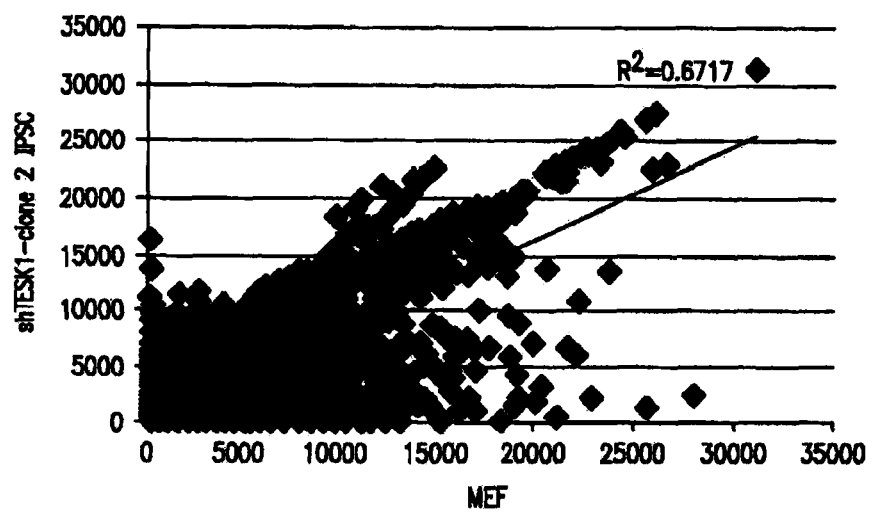

The present invention provides that induced cells can reach a fully pluripotent state. Several iPS clones for each kinase shRNA as well as shRNA controls are derived and analyzed for expression of pluripotency markers. All clones are GFP+, indicative of reactivated Oct4 expression (FIG. 1). Immunostaining confirms that AP, Nanog, and SSEA1 are also activated in all clones. To show that derived clones exhibit the full differentiation capacity of mES cells, embryoid body (EB) formation is evaluated. All derived clones show efficient EB formation, and EBs show positive staining for lineage markers such as β-tubulin III (ectoderm), AFP (endoderm), and α-actinin (mesoderm). When these shRNA-TESK1-iPSCs are injected into athymus nude mice, teratomas are readily derived in 3-4 weeks.

shTESK1-iPSCs exhibit fully pluripotent state: shTESK1-iPSCs have turned on endogenous mES markers. GFP+ shTESK1/iPSCs are collected on iD-16 and cultured with feeder layers to detect the expression of SSEA-1 and Nanog and alkaline phosphatase (AP) staining for determination of pluripotency. shTESK1-iPSCs can differentiate into three germ layers in vitro. Embryoid body formation assay is used to evaluate the differentiation capacity of derived shTESK1-iPSCs. Spontaneously differentiated cells are fixed at Day 14 with 4% paraformaldehyde and immunostained with β-tubulin III (ectoderm), Sarcomeric Actinin (mesoderm), or AFP (endoderm).

shTESK1-iPSCs can differentiate into many lineages in vivo. shTESK1-iPSCs are injected subcutaneously into the dorsocaudal end of nude mice. Teratomas are surgically removed around 3 weeks post-injection, fixed, and sectioned for H&E staining. Whole-genome mRNA expression profiling also indicates that shRNA-TESK1-iPSC-derived clones exhibit a gene expression pattern more similar to mouse ES cells than MEFs (FIG. 3). Thus, the present invention provides that the enhancing effects of kinase knockdown by shRNA on reprogramming do not alter the differentiation capacity of induced pluripotent cells.

TESK1, testicular protein kinase 1, is a Ser/Thr kinase with a functional domain related to LIM-kinases and a unique C-terminal proline-rich domain. TESK1 and Lim kinases specifically phosphorylate cofilin at Ser-3 position in vitro and in vivo, and TESK1 stimulates actin stress fiber formation as well as focal adhesion. Since the analysis of the ILK signaling network by IPKB system suggests that two of the identified kinases, TESK1 and LIMK2, phosphorylate cofilin, the present invention provides that inhibiting TESK1 and LIMK2 function in stabilizing the cytoskeleton can enhance iPSC generation.

Figure 4A:
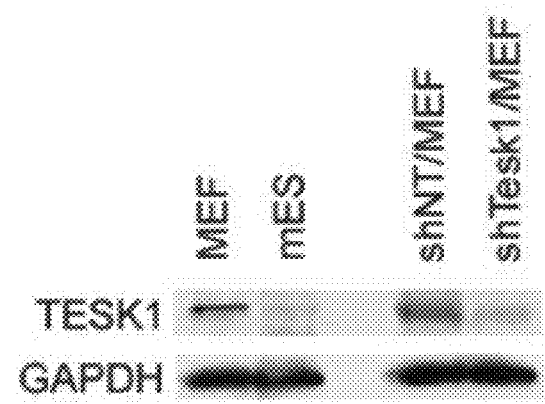
FIGS. 4A-4C show that TESK1 regulates cytoskeleton formation/destabilization during iPSC induction.
Figure 4B:
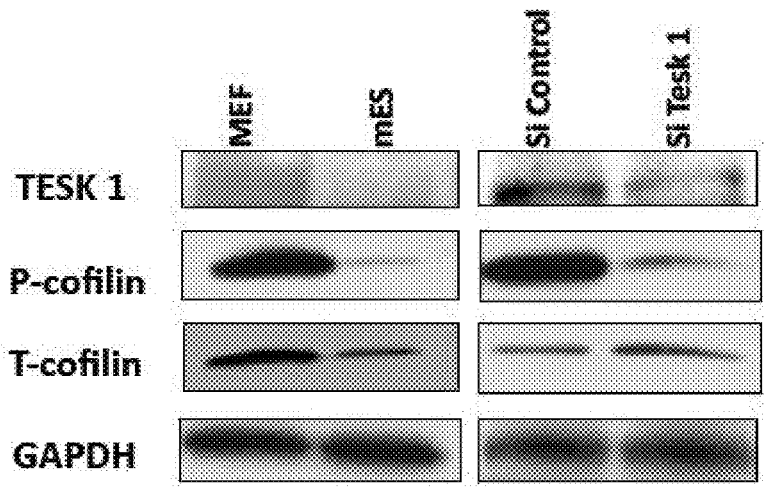
Figure 4C:
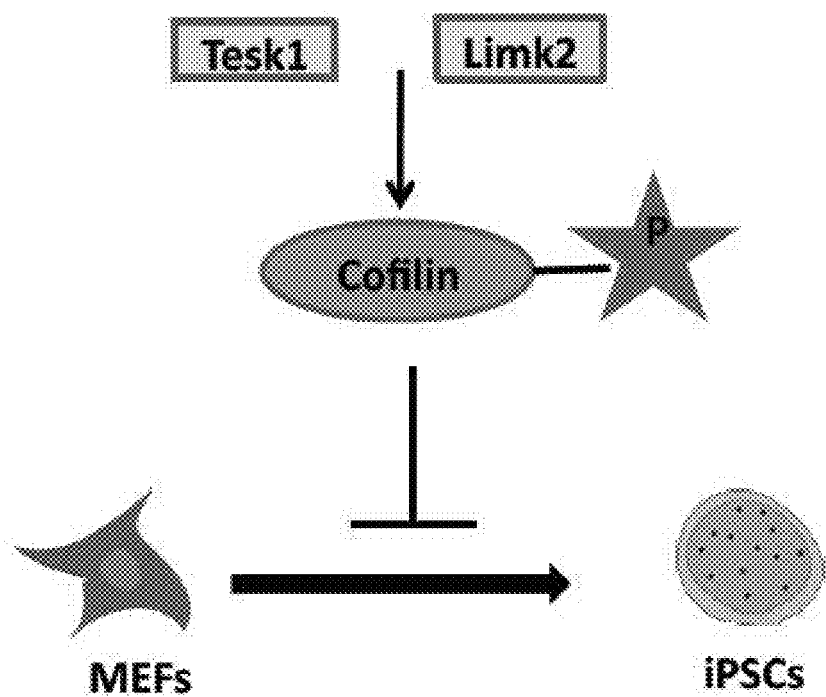

Microarray analysis and western blotting experiments show that TESK1 expression is higher in MEF as compared with mES cells and that the shRNA efficiently silenced TESK1 in MEF (FIG. 4). To determine the role of TESK1 in cytoskeleton stabilization, actin organizations are detected by rhodamine-labeled phalloidin in MEF cells with siRNA targeting TESK1 or control for 72 hours. Actin structures are not as conspicuous in mES cells as seen in MEF. Visualizing actin organization reveals that MEFs have poly-nucleation of actin filaments and that knockdown of TESK1 disrupts this filamental structure (FIG. 4).

Example 6

Phosphorylation Target of Barrier Kinases

The present invention provides that TESK1 regulates phosphorylation of cofilin (P-cofilin) in MEFs. The levels of P-cofilin in MEF and mES are detected by immunoblotting and the knockdown of TESK1 in MEFs results in a decreased level of P-cofilin (FIG. 4). LIMK2 silencing results in a phenotype, decreased P-cofilin, and a disruption of actin filaments very similar to TESK1. Actin cytoskeleton structures are also monitored on OSKM and shTESK1, shLIMK2, or shControl lentiviral transduction in MEF cells at day 2, 4, or 6. The present invention provides that TESK1 and LIMK2 knockdown results in decreased cofilin phosphorylation and disruption of actin filament structures during reprogramming.

iPSCs derived from kinase shRNAs-treated samples are positive for ES stemness markers: GFP+ kinase knockdown iPSCs are derived on iD-16 and cultured with feeder layers to detect expression of SSEA-1 and Nanog and alkaline phosphatase (AP) staining for determination of pluripotency. iPSCs derived from kinase shRNAs treated samples can differentiate into three germ layers in vitro: Embryoid body formation assay is used to evaluate the differentiation capacity of derived shKinase iPSCs.

EBs are formed using a hang-drop method and allowed for spontaneous differentiation. On Day 14, differentiated cells are fixed with 4% paraformaldehyde and immunostained with β-tubulin III (ectoderm), Sarcomeric Actinin (mesoderm), or AFP (endoderm). Silencing of TESK1 and LIMK2 modulates cytoskeleton re-arrangement during reprogramming: Actin cytoskeleton formation can be monitored by rhodamine-phalloidin upon 4-factors and shTESK1 or shLIMK2 lentiviral transduction in MEF cells at Day 2, 4 or 6. MEFs are also transduced with empty vector without shRNA insertion as a control. Nucleus can be stained with Dapi. Phosphorylated and total cofilin levels were detected in MEFs on same days upon same treatment.

The present invention provides a plausible mechanism of TESK1 and LIMK2 function in iPSC generation can be proposed (FIG. 4C), wherein TESK1 or LIMK2 phosphorylates cofilin to promote/stabilize cytoskeleton structure in cells. RNAi-mediated silencing of TESK1 or LIMK2 inhibits cofilin phosphorylation, which in turn disrupts actin-poly nucleation. Disruption of the actin cytoskeleton promotes the mesenchymal-to-epithelial-transition step of reprogramming by OSKM-infected MEFs and thus enhances iPSC generation. Reorganization of the actin cytoskeleton is important in many cellular functions such as movement, adhesion, morphogenesis, and cytokinesis. Actin filaments are connected to the extracellular matrix (ECM) by focal adhesion. Another intriguing possibility is that knockdown of TESK1 mediates the reorganization of actin that alters the ECM structural framework to create an ES cell niche, thus facilitating iPSC generation. The present invention provides the kinase regulators and networks involved in iPSC creation.

Example 7

NSAID for IPS Cell Reprogramming

The NSAID Nabutone enhances iPS cell generation: a genomics database drug discovery strategy was developed to identify small molecules that enhance reprogramming. To shorten the list without extensive shot-gun screening, candidate molecules that potentially either antagonized MEF-specific genes or upregulated MES-specific/reprogramming genes are focused on. To do so, computational screening by utilizing NextBio (nextbio.com) data-mining tools to collect information from public data sources is conducted as in Kupershmidt et al. (PLoS One 5 (2010)). Using highly enriched genes in either MES or MEF as queries, 17 molecules (Table 5) are acquired that either negatively regulated MEF genes or positively affected MES genes from the NextBio meta-analysis.

TABLE 5

Molecules that either negatively regulate
MEF genes or positively affect MES genes.

| ID | Molecules | CAS # | Predicted targets |
|---|---|---|---|
| 1 | Nickel sulfate hexahydrate (NiSO$_4$) | 10101-97-0 | WISP1, PRRX1, LYZS |
| 2 | 2,3,7,8-tetrachlorodibenzo-p-dioxin | 1746-01-6 | TGF-β3 |
| 3 | Nabumetone | 42924-53-8 | COX2 |
| 4 | 4-hydroxytamoxifen (OHTM) | 68047-06-3 | Sox2 |
| 5 | Moclobemide | 71320-77-9 | Nanog |
| 6 | Lectin | | DPPA5 |
| 7 | Corynanthine hydrochloride | 66634-44-4 | TDGF1 |
| 8 | TGF-β | | Oct3/4 |

TABLE 5-continued

Molecules that either negatively regulate
MEF genes or positively affect MES genes.

| ID | Molecules | CAS # | Predicted targets |
|---|---|---|---|
| 9 | Acitretin | 55079-83-9 | Oct3/4 |
| 10 | Retinoic acid p-hydroxyanilide | 65646-68-6 | Oct3/4 |
| 11 | Diacerein | 13739-02-1 | Nanog |
| 12 | Phorbol 12-myristate 13-acetate | 16561-29-8 | Nanog |
| 13 | Progesterone | 57-83-0 | Nanog |
| 14 | Tolazamide | 1156-19-0 | Nanog |
| 15 | 15-deoxy-Δ$^{12, 14}$-prostaglandin J$_2$ | 89886-60-2 | Klf4 |
| 16 | (−)-Norepinephrine | 51-41-2 | c-Myc |
| 17 | β-estradiol | 50-28-2 | c-Myc |

All 17 molecules are tested by examining alkaline phosphatase (AP)+ colony formation during reprogramming while these molecules were applied. Molecules not showing adverse effect on AP+ colony formation are picked for further study. To that end, 6 molecules were picked—Nabumetone, 4-hydroxytamoxifen (OHTM), Corynanthine, Moclobemide, NiSO4, and lectin—for further analysis (FIG. 7A). To evaluate their effect on induction of mature GFP+ iPS cells, OSKM-transduced Oct4-EGFP MEFs are treated four days after transduction with each of these factors separately. Among the six, the NSAID prostaglandin-endoperoxide synthase (PTGS) and the cyclooxygenase (COX) inhibitor Nabumetone greatly increased the number of reprogrammed colonies by at least 2.8-fold (FIG. 7B) compared with DMSO controls, while Lectin shows minor but consistent improvement on iPSC formation.

FIG. 7B shows that Nabumetone significantly boosts OSKM-induced reprogramming while lectin shows minor but consistent increase as well. Oct4-EGFP MEFs are transduced with OSKM and four days later treated with individual small molecules for at least 10 days. GFP+ colonies are identified. Error bars represent standard deviations of three independent experiments. *p value<0.05; **p value<0.005.

FIG. 7C shows that Nabumetone improves reprogramming through blocking COX2. Oct4-EGFP MEFs are transduced with OSKM. Four days later, cells are treated with Nabumetone or DMSO. The next day, cells are transfected with various siRNAs as indicated. GFP+ colonies are identified at day 12~14. Error bars represent standard deviations of six independent experiments. *p value<0.05; p value<0.005; *p value<0.0005. siNT serves as control.

Example 8

Kinase Inhibitors for IPS Cell Reprogramming and Screen Therefor

The following experimental materials and methods were utilized in this Example.

Cell culture, vectors and virus transduction: Oct4-GFP MEFs were derived from mice carrying an IRES-EGFP fusion cassette downstream of the stop codon of pou5f1 (Jackson lab, Stock#008214) at E13.5. MEFs were cultured in DMEM (Invitrogen, 11995-065) with 10% FBS (Invitrogen) plus glutamine and NEAA. Only MEFs at passage of 0 to 4 were used for reprogramming. pMX-Oct4, Sox2, Klf4 and cMyc were purchased from Addgene. Mouse AurkA was cloned into pMX. The human AurkA D274A mutant retroviral vector was purchased from Addgene. To generate retrovirus, PLAT-E™ cells were seeded in 10 cm plates, and 9 ug of each factor were transfected the next day using Lipofectamine™ (Invitrogen, 18324-012) with PLUS™ (Invitrogen, 11514-015). Viruses were harvested and combined 2 days later. For reprogramming, MEFs were seeded in 12-well plates and transduced with 4F virus the next day with 4 ug/ml Polybrene. One day later, the medium was changed to fresh MEF medium, and 3 days later it was changed to mES culture medium supplemented with LIF (Millipore, ESG1107). GFP+ colonies were picked at day 14 post-transduction, and expanded clones were cultured in DMEM with 15% FBS (Hyclone) plus LIF, thioglycerol, glutamine and NEAA. Irradiated CF1 MEFs served as feeder layers to culture mES cells and derived iPS clones.

Kinase library screening: A kinase library of 244 compounds was obtained from the chemical screening facility at the Sanford-Burnham Institute. The library was purchased from Calbiochem (Library 1: 80 compounds. Cat#539744-1EA; Library 2: 80 compounds. Cat#539745-1EA; Library 3: 84 compounds. Cat#539746-1EA). All compounds are well-characterized protein kinase inhibitors. Compounds were diluted to 2 mM in 96-well plates. 4F-transduced cells were seeded into gelatin coated plates (4000 cells/well). Inhibitors were added every other day until day 13. Cells were then fixed with 4% paraformaldehyde for 20 min at room temperature and number of Oct4-GFP+ colonies was directly counted under a microscope. Cells were then stained with Vector red alkaline phosphatase substrate kit I™ (Vector laboratories, SK5100).

siRNA transfection of MEFs: siRNAs were purchased from Dharmacon and diluted in Opti-MEM™ (Invitrogen, 11058-021) to the desired final concentration. Lipofectamine™ 2000 (Invitrogen, 11668-019) was added to the mix at 2 ul/well in 12-well plates, which were incubated 20 min at RT. For 12-well transfections, 80 ul of the siRNA/lipid mixture was added to each well with 320 ul Opti-MEM™. Three hours later, 0.8 ml of the virus mixture (for iPS) or fresh medium was added to each well and the medium was changed to fresh MEF medium the next day. siRNAs were transfected twice during reprogramming (at days 0 and 5 post-4F infection).

Western blotting: Total cell lysates were prepared by incubating cells in MPER buffer (PIERCE, 78503) on ice for 20 min, and then cleared by centrifugation at 13,000 rpm for 10 min. An equal volume of lysates was loaded onto 10% SDS-PAGE gels, and proteins were transferred to PVDF membranes (Bio-Rad, 1620177) using the semi-dry system (Bio-Rad). Membranes were blocked with 5% milk in TBST for at least 1 hr at room temp or overnight at 4° C. Antibodies used include: anti-mNanog (R&D, AF2729), anti-h/mSSEA1 (R&D, MAB2156), anti-Actin (Thermo, MS1295P0), anti-AFP (Abcam, ab7751), anti-Beta III tubulin (R&D systems, MAB1368), and anti-alpha actinin (Sigma, A7811), anti-mAurkA (Bethyl lab, A300-072A), anti-hAurkA (Bethyl lab, A300-071A), total-GSK3β (Cell signaling technology, 9315S), phospho-GSK3β (Cell Signaling Technology, 9323S).

mRNA quantitative PCR: Total RNAs were extracted using Trizol (Invitrogen). After extraction, 1 ug total RNA was used for RT using Superscript II™ (Invitrogen). Quantitative PCR was performed using a Roche LightCycler480™ II and the Sybr green mixture from Abgene (Ab-4166). Gene primers are listed in Table 6. Other primers were previously described (Takahashi et al. 2006 Cell 126: 663-76).

TABLE 6

RT-qPCR primer sequences.

| Gene | | Primer Sequence | Length | Intron |
|---|---|---|---|---|
| Bmx | forward | 5'-ggaaaatctgcatgctta tgact-3' (SEQ ID NO: 15) | 78 bp | 10774 nt |
| | reverse | 5'-ccctttgtctcagtaac tgctc-3' (SEQ ID NO: 16) | | |
| Igf1r | forward | 5'-gagaatttccttcacaat tccatc-3' (SEQ ID NO: 17) | 69 bp | 3194 nt |
| | reverse | 5'-cacttgcatgacgtctct cc-3' (SEQ ID NO: 18) | | |
| IptkB | forward | 5'-ggcgggaaaccatcagt t-3' (SEQ ID NO: 19) | 76 bp | 1897 nt |
| | reverse | 5'-ttcacagagccatcttcc ttc-3' (SEQ ID NO: 20) | | |
| Lck | forward | 5'-cacggtcgaatcccttac c-3' (SEQ ID NO: 21) | 78 bp | 2499 nt |
| | reverse | 5'-tctcaccatgcggtagc c-3' (SEQ ID NO: 22) | | |
| Stk6 | forward | 5'-ttgcagacttcgggtgg t-3' (SEQ ID NO: 23) | 67 bp | 2496 nt |
| | reverse | 5'-tccagggtgccacacat t-3' (SEQ ID NO: 24) | | |
| Syk | forward | 5'-tcctttcaacgttccat gct-3' (SEQ ID NO: 25) | 89 bp | 13.7 kb |
| | reverse | 5'-tgggaagtgtatggaga agtacc-3' (SEQ ID NO: 26) | | |
| Mapk11 | forward | 5'-cctgaggttctggcaaa gat-3' (SEQ ID NO: 27) | 88 bp | 623 nt |
| | reverse | 5'-cactgctgaggtccttc tgg-3' (SEQ ID NO: 28) | | |
| Mapk14 | forward | 5'-gaccttctcatagatga gtggaaga-3' (SEQ ID NO: 29) | 92 bp | 1.1 kb |
| | reverse | 5'-caggactccatttcttc ttggt-3' (SEQ ID NO: 30) | | |
| ItpkA | forward | 5'-gaaaccagcgaggacgt g-3' (SEQ ID NO: 31) | 72 bp | 6.5 kb |
| | reverse | 5'-catgacaggcagattga cca-3' (SEQ ID NO: 32) | | |

Immunostaining: Cells were washed twice with PBS and fixed with 4% paraformaldehyde at room temperature for 20 min. Fixed cells were permeabilized with 0.1% Triton X-100™ for 5 min. Cells were then blocked in 5% BSA in PBS containing 0.1% Triton X-100™ for 1 hr at room temperature. Primary antibodies were diluted from 1:100 to 1:400 in 2.5% BSA PBS containing 0.1% Triton X-100™, according to the manufacturer's suggestion. Cells were stained with primary antibody for 1 hr and then washed three times with PBS. Secondary antibodies were diluted 1:400 and cells were stained for 45 min at room temperature.

EB formation and differentiation assay: iPS cells were trypsinized into a single cell suspension and the hanging drop method was used to generate embryoid bodies (EB). For each drop, 4000 iPS cells in 20 ul EB differentiation medium were used. EBs were cultured in hanging drops for 3 days before being reseeded onto gelatin-coated plates. After reseeding, cells were further cultured until day 14, when beating areas could be identified.

Teratoma formation and chimera generation: iPS cells were trypsinized and resuspended at $1 \times 10^7$ cells/ml. Athymic nude mice were anesthetized with Avertin, and then approximately 150 ul of the cell suspension was injected into each mouse. Mice were checked for tumors every week for 3 to 4 weeks. Tumors were harvested and fixed in zinc formalin solution for 24 hrs at room temp before paraffin embedding and H&E staining. To test the capacity of derived iPSC clones to contribute to chimeras, iPS cells were injected into C57BL/6J-Tyr$^{(C-2J)/J}$ (albino) blastocysts. Generally, each blastocyst received 12-18 iPS cells. ICR recipient females were used for embryo transfer. Donor iPSCs confer agouti or black coat color.

mRNA microarray analysis: Total RNAs from derived iPSCs were harvested and extracted by Trizol method. mRNA microarray analysis was carried out by the microarray facility at the Sanford-Burnham Institute. A scatter plot was used to compare genome wide mRNA expression profiles between iPSCs, MEFs and mES cells.

Cell proliferation assay: 3000 MEFs were seeded in each well in 96-well plates and transduced with 4F virus for three days. Cells were then treated with inhibitors at 0.5 µM and harvested every other day. Cells were incubated with mES medium containing Celltiter 96 Aqueous™ one solution (Promega, G3580) for 1 hr in tissue culture incubator. Absorbance at 490 nm was then measured for each well using a plate reader, and data was used to generate relative proliferation curves using the signal from day 3 post-transduction as a reference.

Cell cycle analysis: MEFs or 4F-infected MEFs were treated with inhibitors for two days and then harvested and trypsinized before fixing in 75% ethanol overnight. Cells were centrifuged at 1000 rpm for 5 min, washed once with PBS, and treated with PI staining solution for at least 30 min at room temperature before flow cytometry analysis. ~20000 events per sample were collected per analysis and cell cycle data was modeled using ModFit™.

Figure 9A:
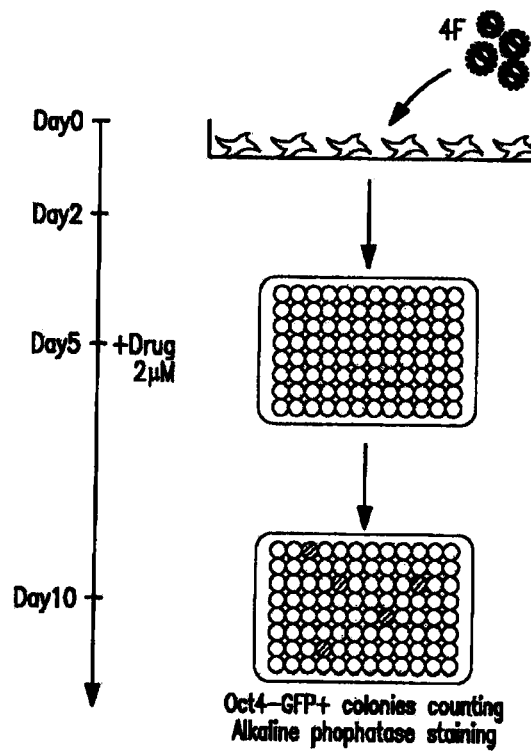
FIGS. 9A-9B are a series of graphical and pictorial representations depicting a kinase inhibitor library screen identifies essential and barrier kinases.

The present invention provides an inhibitor screen to identify both barrier and essential kinases that function in reprogramming. Additionally, the present invention provides a kinase inhibitor library screen that identifies small molecule activators or inhibitors of iPSC generation. To define signaling mechanisms underlying reprogramming, a double-blind screen of 244 well-characterized cell-permeable protein kinase inhibitors was undertook to identify kinases that enhance or inhibit the process. Mouse embryonic fibroblasts from a transgenic line in which GFP expression is driven by the endogenous Oct4 promoter were chosen as the starting material for a reporter cell line of somatic cell reprogramming. Fully reprogrammed cells switch on endogenous Oct4 expression, making resultant iPS colonies GFP-positive and enabling quantification of reprogramming efficiency. To minimize well-to-well variation, MEFs were first transduced with 4F factors in bulk (FIG. 9A) and then reseeded at 3000 cells/well into gelatin-coated 96-well plates before inhibitor treatment. Starting at day 3 post-transduction, inhibitors were added at a final concentration of 2 µM and media were refreshed every other day with mES culture medium plus inhibitor. At day 13 post-transduction, plates were fixed in 4% paraformaldehyde and GFP-positive colonies were directly quantified microscopically.

Figure 9B:
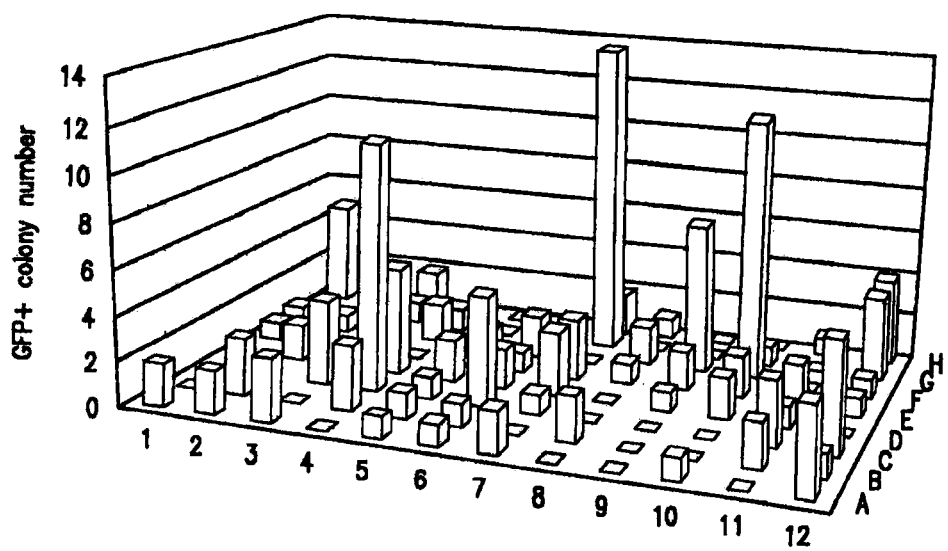

Two columns of wells from each plate (columns 1 and 12) were treated with DMSO (vehicle) only and served as controls. On average, 2-3 GFP positive colonies per well were observed in control samples, which was around 0.07% overall reprogramming efficiency and comparable to known reports. To identify inhibitors that significantly enhance reprogramming efficiency, a minimum of a 2.5-fold increase in GFP-positive colony number as a filter was set. Using these criteria, eleven inhibitors were identified as potential activators of reprogramming or "barrier hits" (FIG. 9B and Table 7).

TABLE 7

Additional compounds and barrier hits.

| Compound ID | Compound Name | Potential Targets |
|---|---|---|
| BIM-0086769 | KN-62 | CaM kinase II (900 nM) |
| BIM-0086727 | Alsterpaullone | GSK-3β (4 nM), Cdk/cyclin B (35 nM) |
| BIM-0207133 | Arcyriaflavin A, synthetic | Cdk4/cyclin D1 (59 nM), CaM kinase II (25 nM), PKA (>2 µM), PKC (>100 µM) |
| BIM-0207164 | IP3K Inhibitor | IP 3-K (10.2 µM) |
| BIM-0050621 | ML-7, hydrochloride | Myosin light chain kinase (300 nM), PKA (21 µM), PKC (42 µM) |
| BIM-0086701 | PP3 | EGFR kinase (2.7 µM) |
| BIM-0086714 | SyK Inhibitor III | Syk kinase (2.5 µM), Src (29.3 µM) |
| BIM-0086660 | Aurora Kinase Inhibitor III | Aurora A (42 nM), Lck (131 nM), Bmx (386 nM), IGF1-R (591 µM), SyK (887 nM) |
| BIM-0086787 | Sphingosine Kinease Inhibitor | Sphingosine kinase (0.5 µM) |
| BIM-0086716 | TGF-β RI Inhibitor III | Activin receeptor-like kinase 4 (129 nM), -5 (47 nM), p38 MAPKα (10.6 µM) |
| BIM-0207174 | P38 MAP Kinase Inhibitor IV | p38α MAPK (130 nM), p38β MAPK (550 nM) |

Representative barrier kinase hits were identified by dramatic increases in Oct4-GFP+ colony numbers following some drug treatments. GFP+ colonies were quantified and images were taken at day 14 post 4F transduction (data not shown).

Based on the information provided, one skilled in the art would be able to design and synthesize compounds (including peptides, nucleic acids, and small molecules) for targeting the same barrier candidates for iPS cell reprogramming as shown in Tables 1, 3, 4, 6, 7 or 8.

Since kinases may also be required for iPSC generation, alkaline phosphatase staining was performed in order to identify potential "essential hits". Since genes encoding targets of essential hits could function at various reprogramming stages, and most cells did not attain a fully reprogrammed state, an extremely stringent criterion was used: only wells devoid of any AP staining and with no obvious decrease in cell number were scored as essential hits. Representative hits of essential kinases were identified by loss of AP staining and lack of signs of cell death (data not shown).

Based on these standards, nine kinase inhibitors were identified as essential hits, and further analysis revealed that among them (Table 8) were four direct inhibitors of cell cycle dependent kinases (Cdks), indicating that cell cycle control is critical for reprogramming. Table 9 lists essential hits and compounds of the present invention.

TABLE 8

Additional compounds and essential hits.

| Compound ID | Compound Name | Potential Targets |
|---|---|---|
| BIM-0086655 | AGL 2043 | PDGFR (800 nM), Flt3 and Kit (1-3 µM) |
| BIM-0207149 | Cdk2/9 Inhibitor | Cdk2/E (2 nM), Cdk9/T1 (4 nM), GSK-3β, Cdk4/D1, Cdk7/H, Cdk1/B, and Abl (20, 53, 70, 80, and 160 nM) |
| BIM-0086744 | Cdk/Crk Inhibitor | Cdks (IC50 = 48 nM, 9 nM, 10 nM, 71 nM, and 9 nM for Cdk1/B, Cdk2/E, Cdk3/E, Cdk5/p35, Cdk7/H/MAT1, and Cdk9, respectively), Cdk4/D1, Cdk6/D3, and GSK-3β (839 nM, 282 nM, and 754 nM) |
| BIM-0086751 | Fascaplysin, synthetic | Cdk4/D1 (0.35 µM), Cdk6/D1 (3.4 µM) |
| BIM-0086708 | Rho Kinase Inhibitor IV | 11.8 nM, >10 µM, >10 µM, 3.26 µM, 2.35 µM, and 2.57 µM for ROCKII, PKA, PCK, PKG, Aurora A, and CAMKII, respectively |
| BIM-0086768 | K-252a, Nocardiopsis sp. | CaM kinase II (1.8 nM), myosin light chain kinase (20 nM), PKA (18 nM), PKC (25 nM), PKG (20 nM), and gp140trk (3 nM) |
| BIM-0207189 | UCN-01 | 9 nM, 34 nM, 30 nM, 590 nM, and 530 nM for PKCα, PKCβ, PKCγ, PKCδ, and PKCε, 7 nM, 27 nM, 50 nM, 50 nM, 150 nM and 1.04 µM for Chk1, Cdc25C-associated protein kinase 1, Cdk1, PAK4, Cdk5/p25 and Chk2, 33 nM, 50 nM, 95 nM, 500 nM, 500 nM and 1.9 µM for PDK1, lck, MAPKAP kinase-2, Akt, GSK-3β and PKA |
| BIM-0207186 | PI 3-K Inhibitor VIII | 0.3, 40, 100, and 850 nM for p110α, p110γ, PI 3-K C2β, and p110β |
| BIM-0207192 | Reversine | MEK1 (8 nM), myosin II heavy chain (10 nM), Aurora kinases A, B and C (IC50 = 400, 500 and 400 nM) |

Figure 14C:
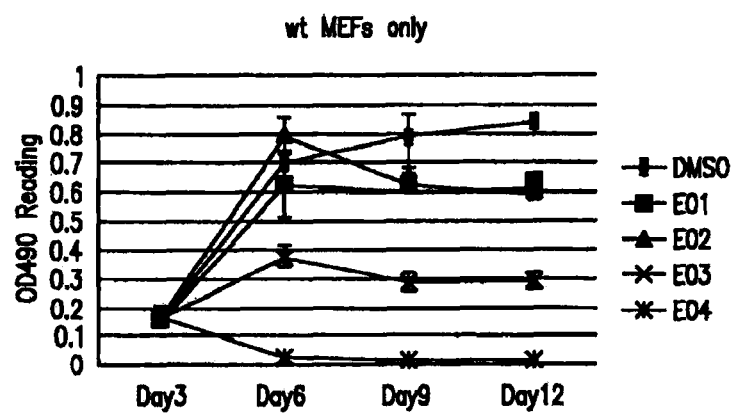
Figure 14D:
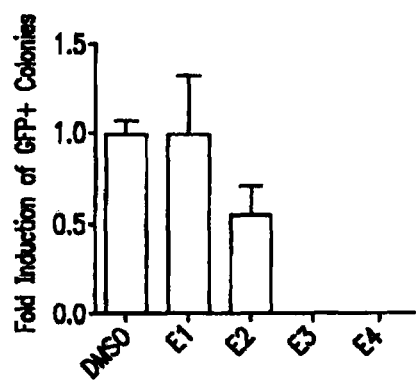

Four of the remaining essential hits was tested (FIG. 14A) and found that three inhibited MEF proliferation to various extents with or without four-factor transduction (FIGS. 14B-14C) and that reprogramming efficiency was positively correlated with the extent of that inhibition (FIG. 14D). Overall, these findings suggest that compromised reprogramming efficiencies seen following inhibition of essential kinases are correlated with inhibition of proliferation.

Figures 10A, 10B:
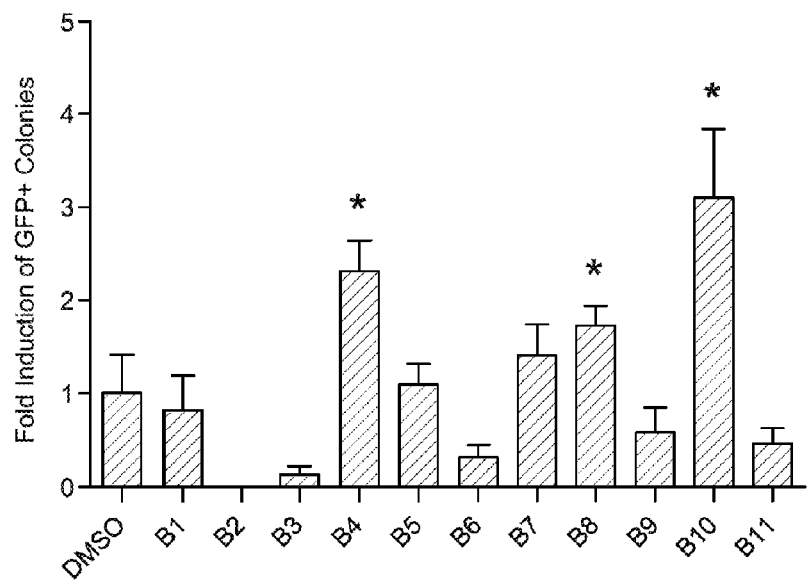
FIGS. 10A-10D are a series of graphical and pictorial representations depicting inhibitors of TGFβ, p38, IP3K and Aurora Kinase enhancing iPSC generation.
Figure 10C:
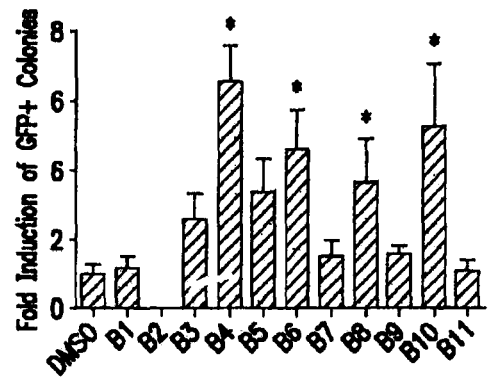
Figure 15A:
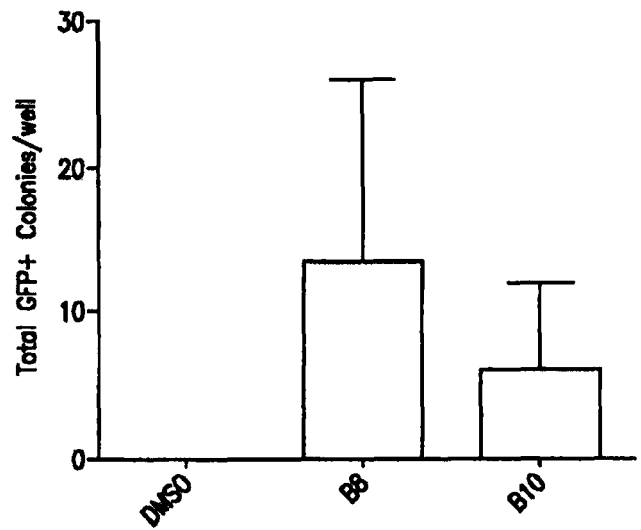
FIGS. 15A-15B are a series of graphic representations of dose/response analysis of kinase inhibitor hits.
Figure 15B:
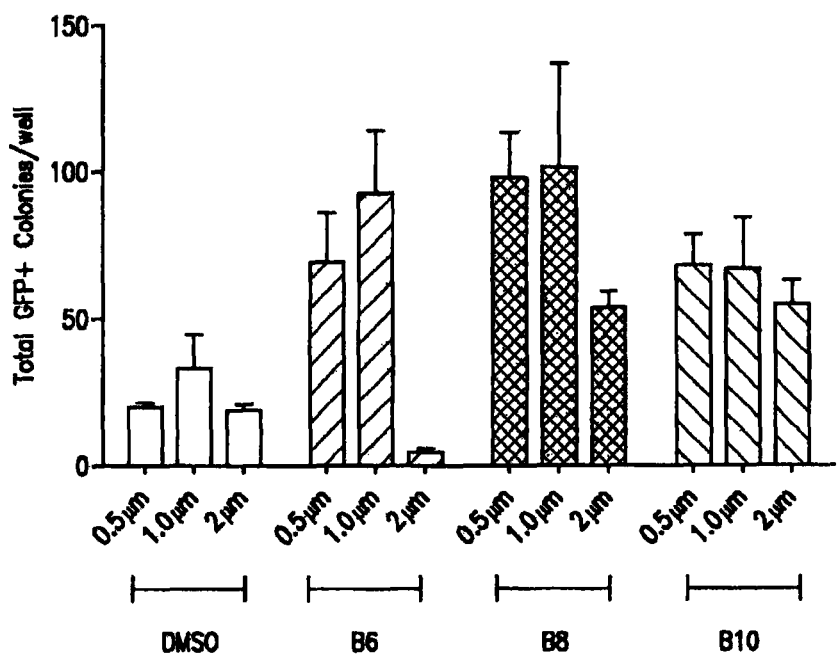
Figure 16A:
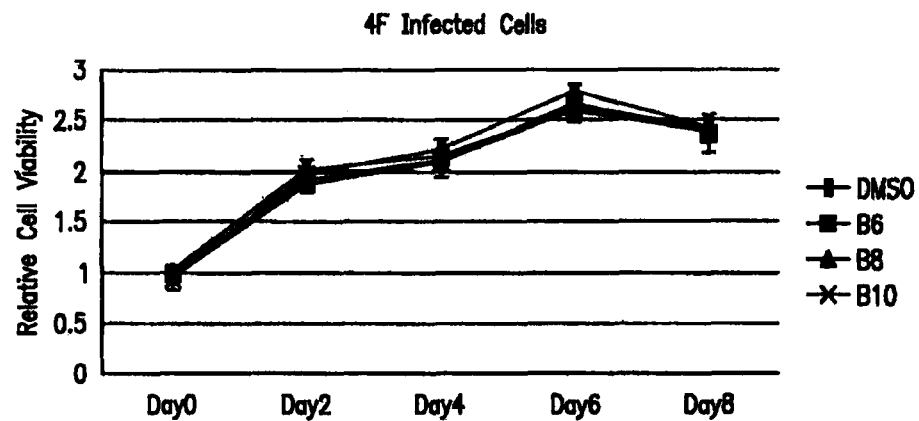
FIGS. 16A-16B is a series of graphical representations depicting identified barrier hits do not alter proliferation of 4F-infected MEFs.
Figure 16B:
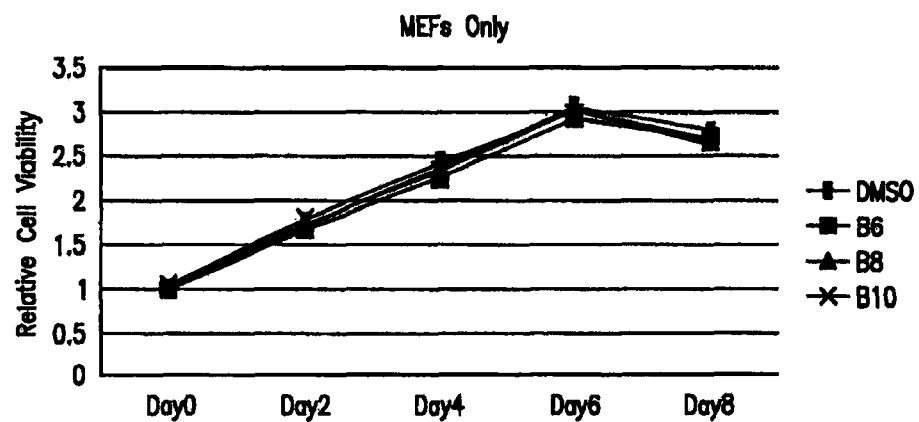
Figure 17:
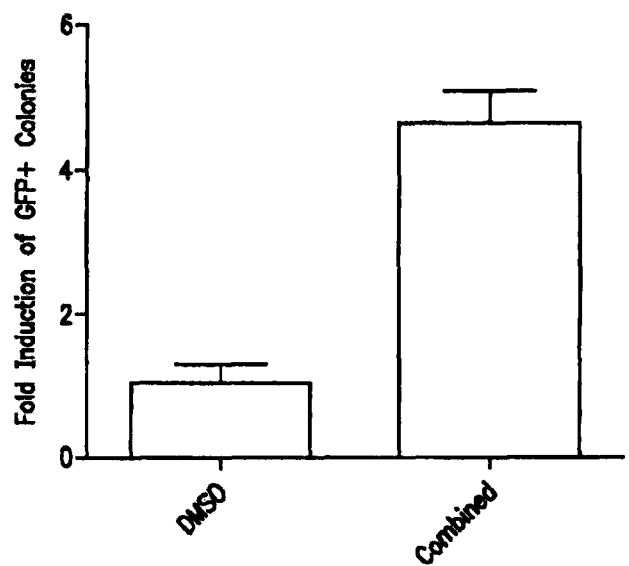
FIG. 17 is a graph plotting induction of GFP+ colonies. A combination of three inhibitors enhances iPSC generation. A combination of B6, B8 and B10 (Combined) enhances reprogramming. The three inhibitors were used at 1 μM each. Data is derived from experiments using triplicate wells.

Inhibitors of TGFβ, IP3K, P38 and Aurora kinase significantly enhance reprogramming. To confirm that the 11 compounds (FIG. 10A, Table 7) identified in the primary screen targeting potential barrier genes enhance iPSC generation, a secondary screen using larger wells and two different drug concentrations (1 µM and 2 µM) was undertook. For the eleven barrier candidates (FIG. 10A), these analyses confirmed that inhibitors B4, B8 and B10 consistently and significantly enhanced reprogramming (FIG. 10B) and were even more potent at the lower 1 µM concentration in a secondary screen (FIG. 10C). Additionally, B8 and B10 enhanced iPSC generation even in non-permissive conditions in which 4F expression was too low to reprogram vehicle-treated MEFs (FIG. 15A). Interestingly, inhibitor B6 enhanced reprogramming more robustly at 1 µM than at 2 µM. Dose/response analyses confirmed that B6, B8 and B10 act as potent enhancers at 0.5 µM (FIG. 15B). Moreover, treatment of both uninfected and 4F-transduced MEFs with these three inhibitors did not significantly promote proliferation (FIG. 16A-16B). Combining B6, B8 and B10 at 1 µM each resulted in a synergistic rather than an additive effect of the three compounds (FIG. 17). Since p53 has been identified as a major barrier to reprogramming, whether B6, B8 or B10 inhibitors enhanced reprogramming when p53 was down-regulated by shRNA was asked. As expected, p53 knockdown in 4F-transduced MEFs greatly enhanced iPSC generation, but that enhancement was equivalent in inhibitor-treated and -untreated conditions (FIG. 18).

Figure 10D:
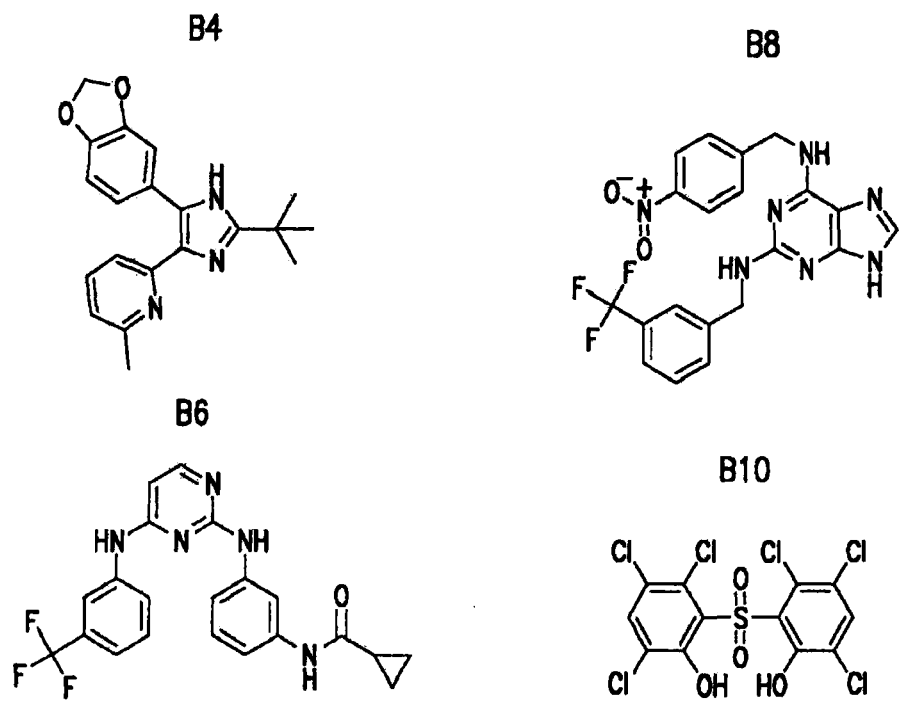
Figure 11D:
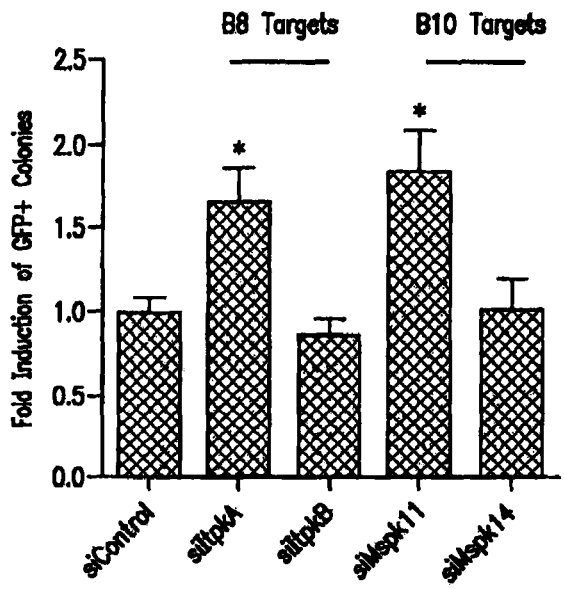

Since B6, B8 and B10 could target multiple kinases at a given concentration, drug specificity was validated by RNAi experiments. To do so, MEFs and mES cells were transfected with siRNAs targeting potential targets of each kinase and knockdown efficiencies were evaluated by RT-qPCR. Indeed, all siRNAs tested efficiently knocked down target genes in MEFs (FIG. 11A-11B) and in mES cells (FIG. 11B and data not shown). Next MEFs were transfected with these siRNAs and then transduced cells with 4F virus 3 hours post transfection. GFP+ colonies were counted at approximately day 12. Indeed, it was observed that Mapk11 (p38β) (a target of inhibitor B10), ItpkA (a target of inhibitor B8), and Stk6 and SyK (targets of inhibitor B6) act as barrier genes: knockdown of any one of these genes during reprogramming resulted in significant increases in iPSC generation (FIG. 11C-11D). Interestingly, knockdown of some B6 targets, such as Bmx, Igf1R and Lck, compromised reprogramming, which may explain in part why B6 both inhibits and enhances reprogramming, depending on concentration. Together, these data confirm that inhibitors B4, B6, B8 and B10 (FIG. 10D) are potent enhancers of iPSC generation and that effects of inhibitor treatment are target-specific.

Inhibitor-treated iPSCs reach a fully reprogrammed state. Although B6, B8 and B10 promote reprogramming, it is possible that treatment with these inhibitors turns on endogenous Oct4 expression but cells do not reach a fully reprogrammed state. To exclude this possibility, iPSCs derived from cells treated with respective inhibitors were analyzed for ES cell marker expression and pluripotency. All GFP+ clones also stained positively with alkaline phosphatase (data not shown). Inhibitor-treated iPS cells can be successfully derived. iPS clones from inhibitor-treated samples were picked and expanded. Cells show endogenous Oct4 expression (data not shown) and alkaline phosphatase positivity (data not shown).

Immunostaining for other mES self-renewal markers confirmed that these cells expressed Nanog and the mES-specific surface protein SSEA1 (data not shown). Inhibitor-treated iPSCs are Nanog- and SSEA1-positive. iPSCs were seeded on irMEF plates and cultured for 3 days, fixed in 4% paraformaldehyde and stained for Nanog and SSEA 1 expression.

Figure 12:
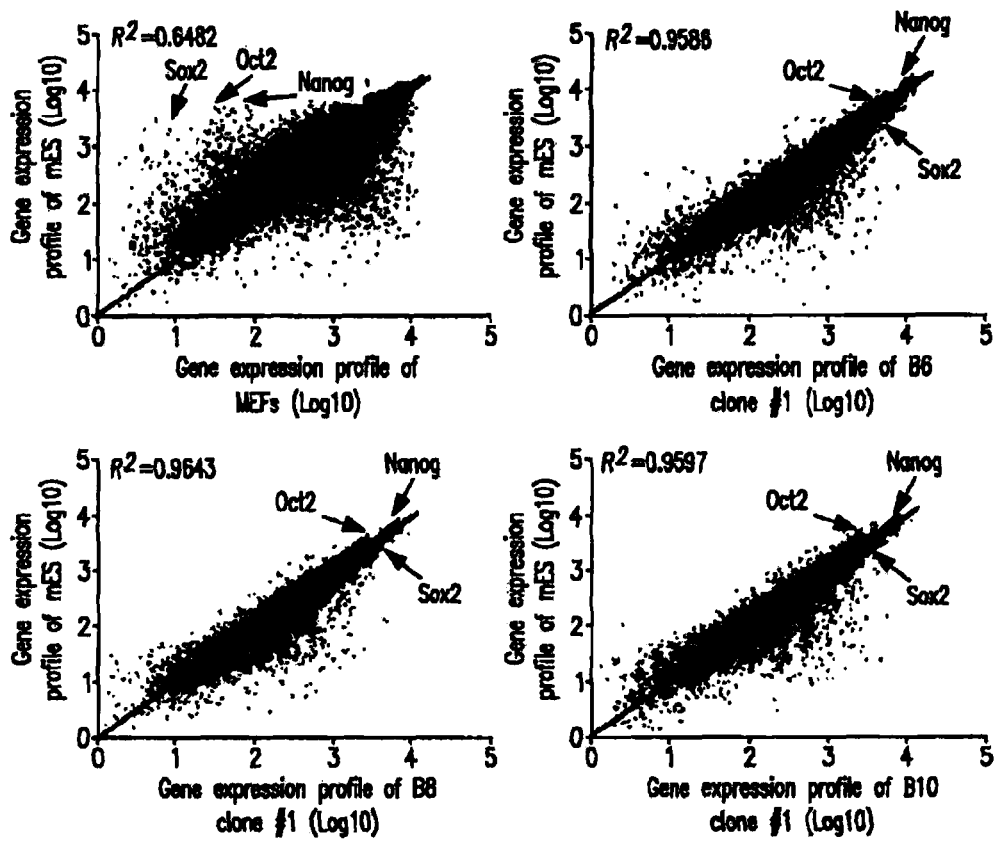
FIG. 12 is a series of graphical representations of genome wide mRNA expression profiles of derived iPSCs. Kinase inhibitor-treated iPS clones show an expression profile resembling that of control mouse ES (CCE) cells ($R^2 > 0.95$).

Moreover, genome-wide mRNA expression profiles verified that these cells showed a gene expression pattern highly similar to mES cells, one that differed significantly from starting MEFs (FIG. 12). To determine whether inhibitor-treated cells acquire the full capacity to differentiate into different lineages, in vitro embryoid body formation assay was used to assess pluripotency. Clones tested readily differentiated into three major lineages, including beating cardiomyocytes, and stained positively for AFP (endoderm), tubulin III (ectoderm) or cardiac actin (mesoderm) (data not shown). Inhibitor-treated iPSCs can differentiate into tissues representing all three germ layers. iPS clones were picked and expanded from inhibitor-treated cells and used for embryoid body (EB) formation. EBs were formed by the hanging drop method with ~2000 cells/20 ul drop. After three days, EBs were transferred to gelatin-coated plates and cultured until day 13, when beating areas were apparent. Cells were fixed with paraformaldehyde and stained with indicated antibodies. AFP, tubulin III and cardiac actin mark endoderm, ectoderm, and mesoderm, respectively. Clones readily differentiated into three major lineages (data not shown).

As a more stringent test of pluripotency, these iPSCs were injected into athymic nude mice and found that all tested clones generated heterogeneous teratomas within 3-4 weeks (data not shown). Inhibitor-treated iPSCs form teratomas in nude mice. iPS clones from each treatment were injected into athymic nude mice and tumors harvested after ~3 weeks.

When iPSCs were injected into the cavity of recipient blastocysts, they successfully integrated with cells of the inner cell mass the next day (data not shown) and contributed to living chimeric mice (data not shown). Inhibitor-treated iPSCs can contribute to chimeric mice.

Cells also contributed to the germline of E13.5 embryos, suggesting that these cells were germline-competent (data not shown). iPSCs contribute to the germline of chimeric embryos. Injected embryos were harvested at E13.5 and genital ridge tissues were dissected and analyzed for GFP-positivity. Together, these data strongly suggest that iPSCs derived from inhibitor-treated cells are fully reprogrammed and can differentiate into all lineages in vitro and in vivo.

AurkA inhibition by B6 enhances Akt-mediated GSK3β inactivation. To identify the mechanism underlying enhanced reprogramming mediated by a kinase inhibitor, the activity of a target of inhibitor B6, Aurora A Kinase (AurkA), was further analyzed due to its known function in cell cycle progression, spindle formation and tumor development. It was first determined whether treatment with inhibitor B6 altered levels of AurkA protein. B6 treatment of both wild type MEFs and 4F-infected MEFs resulted in increased AurkA protein levels relative to untreated cells (FIG. 5a). In addition, a significant increase in AurkA protein levels was seen in untreated 4F-infected cells relative to untreated MEFs. Further experiments suggested that this increase could be due to enhanced transcription, since AurkA mRNAs were induced by 3~4 fold in mock 4F-infected cells relative to mock MEFs (FIG. 13B), and mRNA levels were not significantly altered by B6 treatment (FIG. 13B). These results agree with previous expression profiling studies of MEFs and iPSCs, which showed that AurkA mRNA is highly expressed in mES or iPSCs compared with MEFs. During reprogramming with 4F decreased levels of phosphorylation of GSK3β were also observed (data not shown), indicating that GSK3β is activated.

Interestingly, recent studies indicate that GSK3β inhibition by small molecules enhances iPSC generation from neural stem cells. Therefore, whether AurkA inhibition by B6 altered GSK3β phosphorylation was asked. Indeed, a significant increase in phospho-GSK3β in B6-treated cells was detected (FIG. 13C), while GSK3β total protein levels were unchanged. As a test of specificity, reprogramming in the presence of a different AurkA inhibitor MLN8237 was assessed, which has a potent inhibitory effect and has been tested in myeloma cell lines. AurkA inhibition by MLN8237 promoted a dose-dependent increase of phospho-GSK3β, while total GSK3β levels remained unchanged (FIG. 13D). Increased AurkA protein levels were also detected (FIG. 16). Overall, these results indicate that AurkA inhibition promotes phosphorylation and subsequent inactivation of GSK3β, an effect that likely enhances reprogramming.

Figure 21:
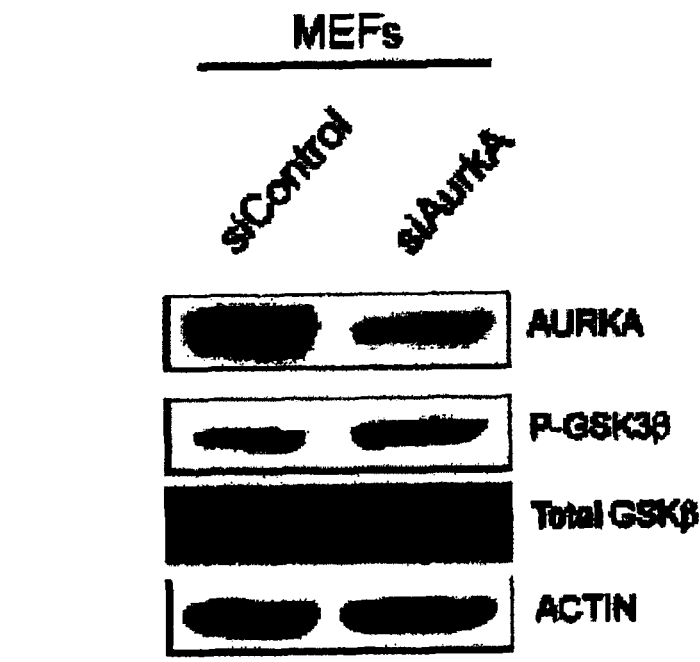
FIG. 21 is a western blot depicting knockdown of AurkA promoting GSK3β inactivation. MEFs were transfected with AurkA and control siRNAs at a final concentration of 50 nM for two days. Cells were then harvested for western blotting analysis of AurkA, total and phosphorylated GSK3β, and actin, as a loading control.

AurkA reportedly has a kinase-independent function. Whether potential inactivation of GSK3β by AurkA proteins requires AurkA kinase activity was therefore asked. To answer this question, AurkA was overexpressed in 4F-infected MEFs using two retroviral constructs: one encoding wild-type mouse AurkA and the other encoding a human AurkA kinase dead mutant D274A (Otto et al. 2009 Cancer Cell 15:67-78) (FIG. 17). AurkA is highly conserved between humans and mouse, the proteins having ~84% identity in amino acid sequence by amino acid alignment. If GSK3β inactivation seen following B6 treatment is AurkA kinase-independent, overexpression of either construct should decrease GSK3β phosphorylation. If that effect is kinase-dependent, overexpression of the kinase-dead mutant should have a dominant-negative effect, similar to effects seen following AurkA inhibition by small molecules. Indeed, a significant increase in levels of phospho-GSK3β was detected in both 4F-infected and untreated MEFs following expression of the kinase-dead mutant (FIG. 13E). Moreover, overexpression of wild-type AurkA promoted a decrease in phospho-GSK3β without altering total protein levels (FIG. 13E). Furthermore, AurkA knockdown by siRNAs in MEFs enhanced GSK3β phosphorylation (FIG. 21). Collectively, these findings suggest that inhibition of AurkA kinase activity promotes GSK3β inactivation.

Figure 13F:
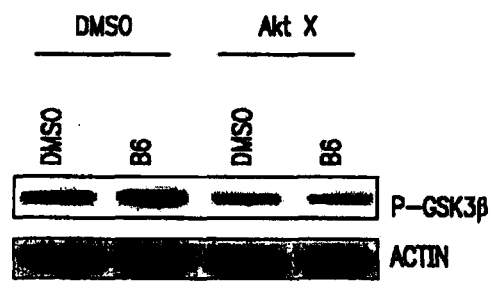
Figure 22:
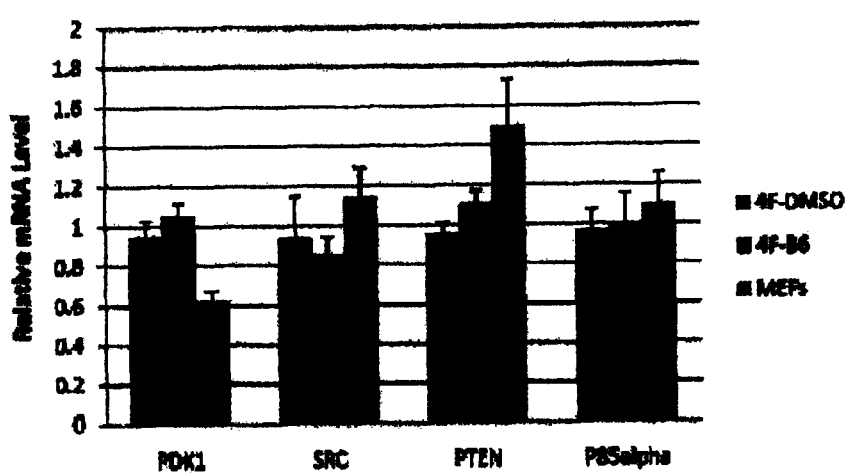
FIG. 22, is a graph plotting relative mRNA levels in MEFs. The graph shows B6 treatment does not alter expression of genes upstream of Akt. MEFs were first transduced with 4F for three days and then treated for another two days with DMSO or 1 μM B6. Total RNAs were harvested and analyzed for indicated factors, which reportedly function upstream of Akt.

Next, it was asked which kinase potentially functions in GSK3β phosphorylation following B6 treatment. Since Akt kinases are well-characterized mediators of GSK3β phosphorylation, it was asked whether Akt inhibitors abolished B6's effect on phospho-GSK3β induction. Indeed, treatment of 4F-infected MEFs by small molecule Akt inhibitors decreased the effect of B6 on GSK3β phosphorylation (FIG. 13F) and inhibited reprogramming (FIG. 13G), suggesting that increased GSK3β phosphorylation seen following AurkA inhibition is mediated by Akt. Also, expression levels of several genes reportedly upstream of Akt such as Pdk1, Src, Pten and p85α were tested but significant changes were not observed when MEFs were first transduced with 4F for three days and then treated with DMSO or B6 (FIG. 22), indicating that B6 treatment does not alter transcription of Akt regulators.

Figure 13G:
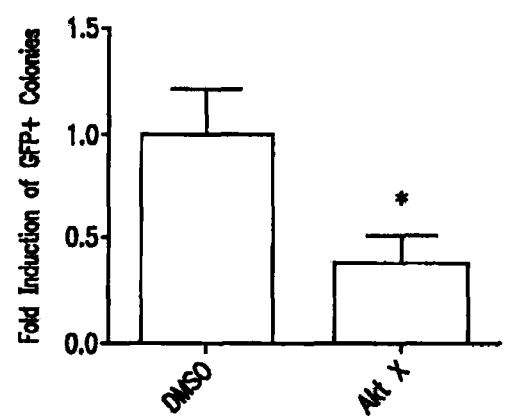
Figure 23A:
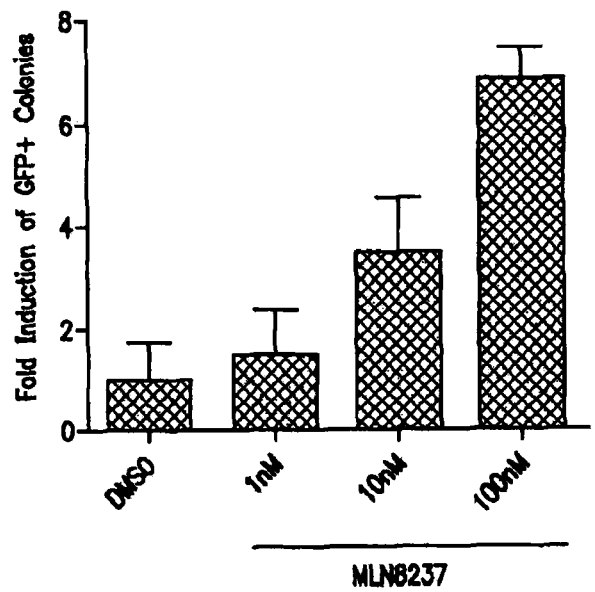
FIGS. 23A-23B are a series of graphical representations depicting dose-dependent enhancement of reprogramming by MLN8237.
Figure 23B:
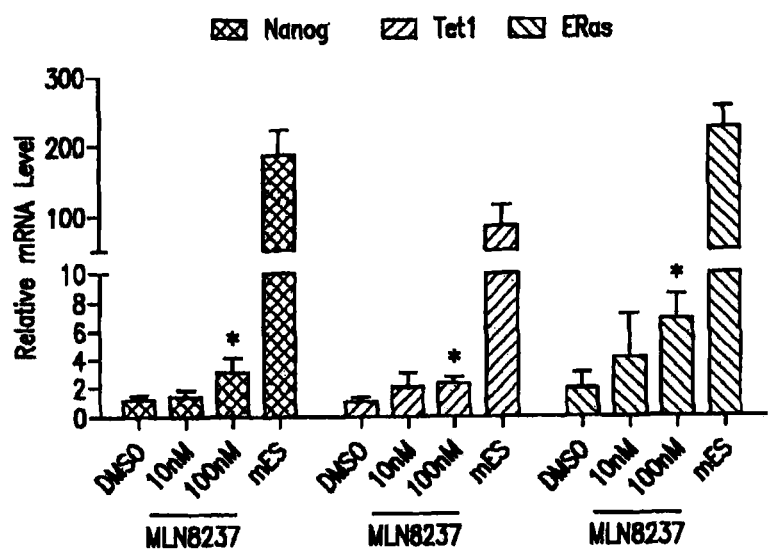

As a test of specificity, whether MLN8237 enhanced iPSC generation was also determined. Treatment of MEF cells with MLN9237 at the low concentration of 10 nM enhanced reprogramming approximately 4-fold, and the effect was dose-dependent (FIG. 13G, FIG. 23A). Gene expression analysis of MLN8237-treated samples also confirmed increases in mES-specific gene expression (FIG. 23B).

Figure 24A:
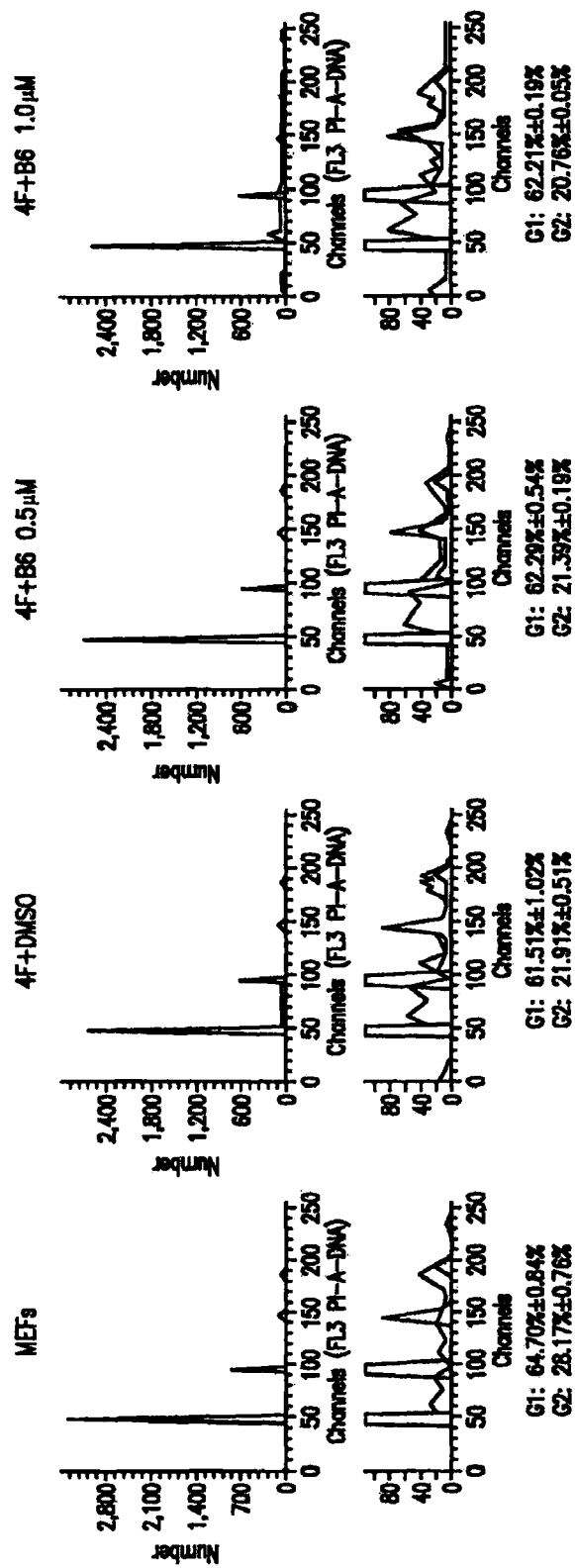
FIGS. 24A-24B are a series of graphical representations of flow cytometry results showing AurkA inhibitors do not alter the cell cycle at low concentrations.
Figure 24B:
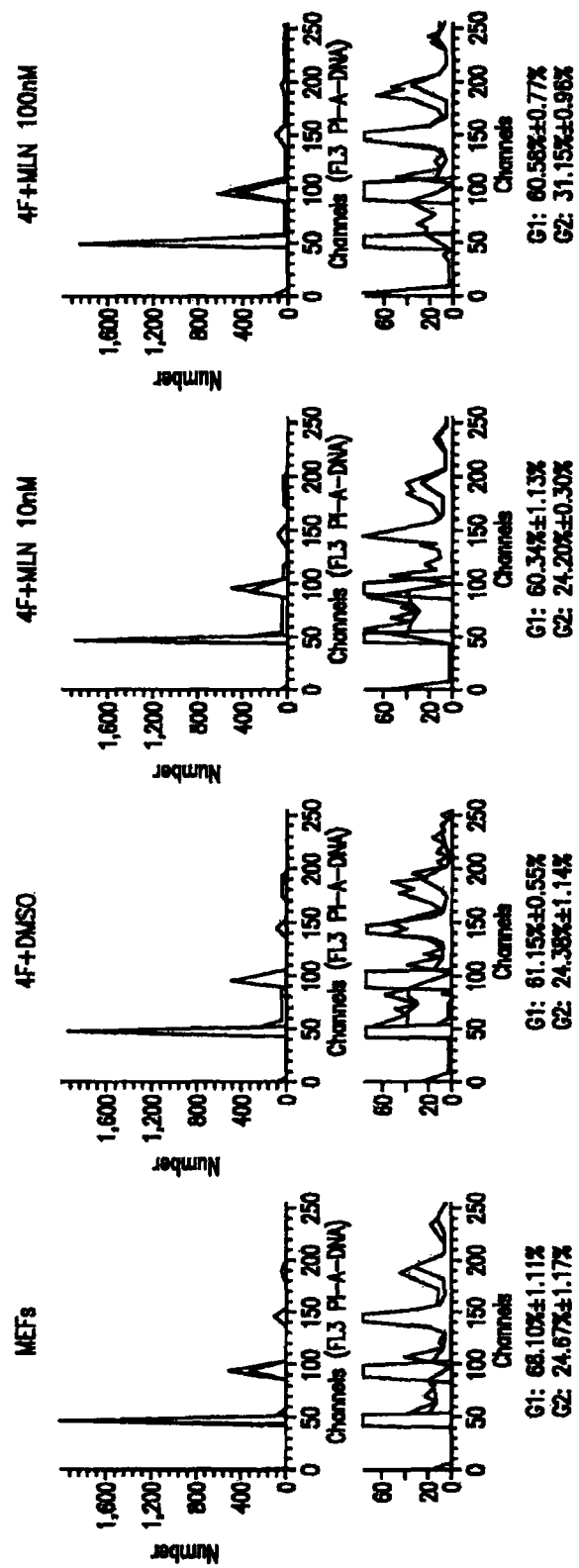

Since AurkA functions in control of spindle formation and the cell cycle, whether the cell cycle of 4F-infected MEFs was significantly altered by treatment with AurkA inhibitors was determined. Treatment with various concentrations of either B6 or MLN8237 promoted little change in cell cycle progression (FIG. 24). However, at a higher concentration of 100 nM, MLN8237 treatment increased the number of cells in G2. However, a significant increase in the number of GFP+ colonies accompanied by induction of an mES-specific gene expression profile was still detected at this concentration of MLN8237 (FIG. 23A-23B), and the size of resultant colonies resembled that of DMSO-treated cells (data not shown), indicating that iPSC formation was not affected by MLN8237 at this dose, in contrast to fibroblast cells which would have undergone G2-arrest under such dose.

Figure 25:
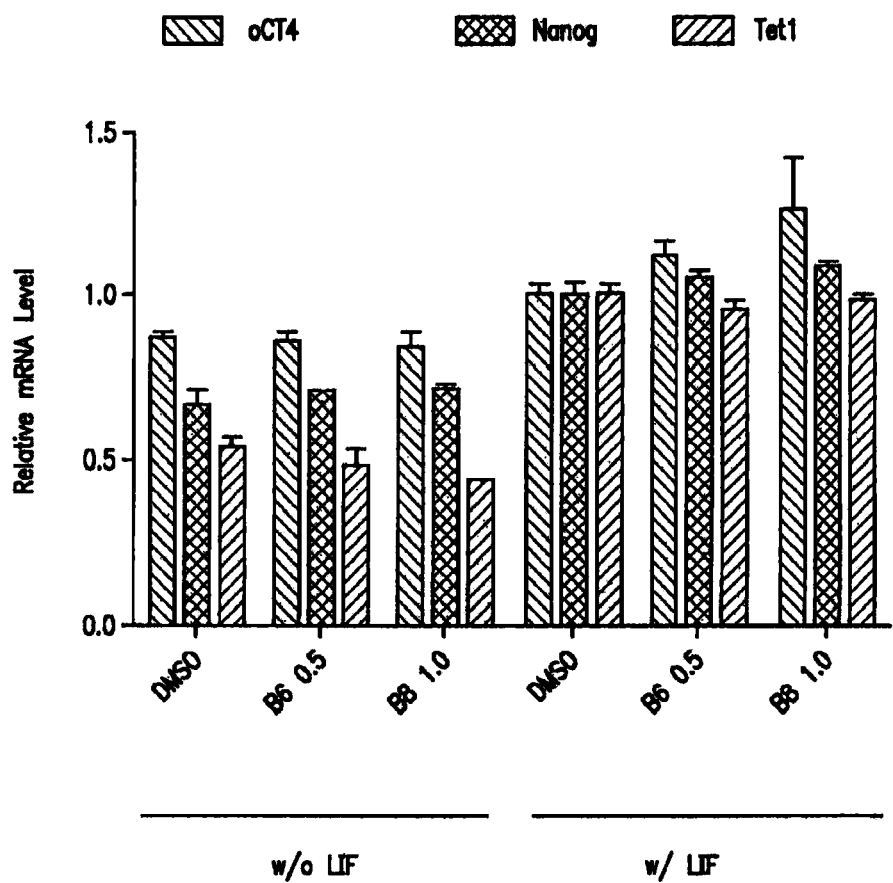
FIG. 25 is a histogram showing AurkA inhibitor treatment does not inhibit mES cell differentiation. Inhibitor B6 does not alter silencing of self-renewal genes following LIF withdrawal. mES cells were cultured both in LIF+ or LIF− medium for 4 days and harvested. Cells were harvested for RNA extraction and RT-qPCR of indicated mES self-renewal genes.

AurkA is known to be highly expressed in mES and iPS cells compared with MEFs, suggesting that it functions to maintain mES self-renewal or pluripotency. To determine whether inhibition of AurkA altered mES self-renewal or differentiation, mES cells were treated with B6 at both 0.5 µM and 1 µM and cultured cells in LIF+ and LIF− conditions for 4 days. LIF withdrawal in both B6-treated and DMSO control cells promoted mES cell differentiation, as indicated by loss of colonies, based on morphology and AP staining (data not shown). RT-qPCR of self-renewal markers confirmed that differentiation was occurring, as those markers were down-regulated in LIF-minus cells (FIG. 25). However, a significant effect on either mES self-renewal (in the presence of LIF) or differentiation (following LIF withdrawal) was not seen, other than a very small increase in Oct4 expression in mES cells, suggesting that B6 treatment has little effect on iPS cells once they have reached the fully reprogrammed state.

Although the invention has been described with reference to the above example, it will be understood that modifications and variations are encompassed within the spirit and scope of the invention. Accordingly, the invention is limited only by the following claims.

---

What is claimed is:

1. An in vitro method of generating an induced pluripotent stem (iPS) cell comprising: a) introducing into a human or mouse fibroblast one or more retroviral vectors encoding nuclear reprogramming factors OCT4, SOX2, KLF4 and c-MYC and b) introducing into the human or mouse fibroblast a nucleic acid that inhibits expression or activity of Aurora A kinase (AURKA) within the human or mouse fibroblast, and c) culturing the resulting human or mouse fibroblast in a cell media that supports growth of human embryonic stem (hES) cells or mouse embryonic stem (mES) cells, thereby generating an iPS cell.

2. The method of claim 1, wherein the nucleic acid is an siRNA, shRNA, miRNA, Locked Nucleic Acid (LNA), antisense oligonucleotide, a chemically modified oligonucleotide, or a combination thereof.

3. The method of claim 1, wherein after step (b), contacting the cell of (a) with an agent that enhances reprogramming of an induced pluripotent stem (iPS) cell.

4. The method of claim 3, wherein the agent is a small molecule, a peptide, a nucleic acid, a pluripotency transcription factor or a combination thereof.

5. The method of claim 3, wherein the agent is a microRNA, miRNA mimic, miRNA inhibitor, Locked Nucleic Acid (LNA), antisense oligonucleotide, a chemically modified oligonucleotide, or a combination thereof.

6. The method of claim 3, wherein the agent is a non-steroidal anti-inflammatory drug (NSAID).

7. The method of claim 3, wherein the agent is selected from the group consisting of nabumetone, 4-hydroxytamoxifen (OHTM), corynanthine, moclobemide, nickel sulfate hexahydrate (NiSCL), lectin, and a combination thereof.

8. The method of claim 3, wherein the agent is selected from the group consisting of nabumetone, 4-hydroxytamoxifen (OHTM), corynanthine, moclobemide, nickel sulfate hexahydrate (N1SO4), lectin, 2, 3, 7, 8-tetrachlorodibenzo-p-dioxin, inhibitor of TGF-β, Acitretin, Retinoicacid p-hydroxyanilide, Diacerein, Phorbol 12-myristate 13-acetate, Progesterone, Tolazamide, 15-deoxy-$\Delta^{12',14}$-prostaglandin $J_2$(−)-Norepinephrine, β-estradiol, and a combination thereof.

9. The method of claim 1, wherein the one or more retroviral vector is introduced into the human or mouse fibroblast cell prior to, simultaneously with or following the step (b).

* * * * *

UNITED STATES PATENT AND TRADEMARK OFFICE
CERTIFICATE OF CORRECTION

| | | |
|---|---|---|
| PATENT NO. | : 9,957,484 B2 | Page 1 of 1 |
| APPLICATION NO. | : 14/256668 | |
| DATED | : May 1, 2018 | |
| INVENTOR(S) | : Tariq M. Rana | |

It is certified that error appears in the above-identified patent and that said Letters Patent is hereby corrected as shown below:

In the Specification

In Column 1, at Line 15, please insert:
--STATEMENT AS TO FEDERALLY SPONSORED RESEARCH
This invention was made with government support under AI043198 awarded by the National Institutes of Health. The government has certain rights in the invention.--

Signed and Sealed this
Twenty-first Day of March, 2023

Katherine Kelly Vidal
*Director of the United States Patent and Trademark Office*